(12) United States Patent
Avihingsanon et al.

(10) Patent No.: US 6,900,015 B2
(45) Date of Patent: May 31, 2005

(54) MEASUREMENT OF PROTECTIVE GENES IN ALLOGRAFT REJECTION

(75) Inventors: Yingyos Avihingsanon, Boston, MA (US); Nali Ma, Wirchester, MA (US); Terry B. Strom, Brookline, MA (US); Miguel C. Soares, Boston, MA (US); Christiane Ferran, Brookline, MA (US); Manikkam Suthanthiran, Scarsdale, NY (US)

(73) Assignees: Beth Israel Deaconess Medical Center, Inc., Boston, MA (US); Cornell Research Foundation, Inc., Ithaca, NY (US)

(*) Notice: Subject to any disclaimer, the term of this patent is extended or adjusted under 35 U.S.C. 154(b) by 140 days.

(21) Appl. No.: 09/777,732

(22) Filed: Feb. 6, 2001

(65) Prior Publication Data

US 2002/0132235 A1 Sep. 19, 2002

Related U.S. Application Data
(60) Provisional application No. 60/240,735, filed on Oct. 16, 2000, provisional application No. 60/239,635, filed on Oct. 12, 2000, provisional application No. 60/238,718, filed on Oct. 6, 2000, and provisional application No. 60/199,327, filed on Apr. 24, 2000.

(51) Int. Cl.[7] .......................... C12Q 1/68; G01N 33/53; C12P 19/34
(52) U.S. Cl. ............................ 435/6; 435/7.1; 435/91.2
(58) Field of Search ........................... 435/6, 7.1, 91.2, 435/7

(56) References Cited

U.S. PATENT DOCUMENTS

| | | | |
|---|---|---|---|
| 5,213,961 A | 5/1993 | Bunn et al. | |
| 5,569,588 A | 10/1996 | Ashby et al. | |
| 6,187,534 B1 * | 2/2001 | Strom et al. ................ | 435/6 |

OTHER PUBLICATIONS

Abraham, et al. *Transfection of the human heme oxygenase gene into rabbit coronary microvessel endothelial cells: Protective effect against heme and hemoglobin toxicity.* Proc. Natl. Acad. Sci. USA 92:6798–6802 (Jul. 1995).
Agarwal, et al. *Induction of heme oxygenase in toxic renal injury: A protective role in cisplatin nephrotoxicity in the rat.* Kidney International 48:1298–1307 (1995).
Agarwal, et al. *Gas–generating systems in acute renal allograft rejection in the rat.* Transplantation 61(1):93–98 (1996).
Agarwal, et al. *Renal response to tissue injury: Lessons from heme oxygenase–1 gene ablation and expression.* J. Am. Soc. Nephrol. 11:965–973 (2000).
Agodoa et al. *Assessment of structure and function in progressive renal disease.* Kidney International 52(Supp.63):S144–S150 (1997).
Aizawa, et al. *Heme Oxygenase–1 is upregulated in the kidney of angiotensin II–Induced Hypertensive Rats.* Hypertension 35:800–806 (2000).
Almond, et al. *Risk Factors for Chronic Rejection in Renal Allograft Recipients.* Transplantation 5(4):752–757 (Apr. 1993).
Alpert, et al. *The Relationahip of Granzyme A and Perforin Expression to Cardiac Allograft Rejection and Dysfunction.* Transplantation 60(12):1478–1485 (Dec. 1995).
Amersi, et al. *Upregulation of heme oxygenase–1 protects genetically fat Zucker rat livers from ischemia/reperfusion injury.* J. Clin. Invest. 104:1631–1639 (1999).
Atkinson, et al. *Cytotoxic T Lympocyte–assisted Suicide.* J. Biological Chemistry 272(33):21261–21266 (1998).
Bach, et al. *Accomodation of vascularized xenografts: expression of "protective genes" by donor endothelial cells in host Th2 cytokine environments.* Nature Medicine 3(2):196–204 (Feb. 1997).
Bach, et al. *Protective genes expressed in endothelial cells: a regulatory response to injury.* Immunology Today, Oct. 1997.
Badrichani, et al. *Bcl–2 and Bcl–$X_L$ serve an anti–inflammatory function in endothelial cells through inhibition of NF–κB.* J. Clin. Invest. 103(4):543–553 (1999).
Beckingham, et al. *Analysis of factors associated with complications following renal transplant needle core biopsy.* British Journal of Urology 73:13–15 (1994).
Benfield, et al. *Safety of kidney biopsy in pediatric transplantation.* Transplantation 67(4):544–547 (Feb. 1999).
Berke. *Unlocking the secrets of CTL and NK cells.* Immunology Today 16(7):343–346 (1995).
Boise, et al. *bcl–x, a bcl–2–Related Gene That Functions as a Dominant Regulator of Apoptotic Cell Death.* Cell 74:597–608 (Aug. 1993).
Carraway, et al. *Expression of heme oxygenase–1 in the lung in chronic hypoxia.* Am J Physiol/Cell. Mol. Physiol. 278:L806–L812 (2000).
Clement, et al. *Perforin and Granzyme B Expression is Associated with Severe Acute Rejection.* Transplantation 57(3):322–326 (Feb. 1994).
Choi, et al. *Heme Oxygenase–1: Function, Regulation, and Implication of Novel Stress–inducible Protein in Oxidant–induced Lung Injury.* Amer. J. of Respiratory Cella nd Molecular Biology 15:9–19 (1996).
Colvin, et al. *Evaluation of Pathology Criteria for Acute Renal Allograft Rejection: Reproducibility, Sensitivity, and Clinical Correlation.* J. Am. Soc. Nephrol 8:1930–1941 (1997).

(Continued)

Primary Examiner—Kenneth R. Horlick
Assistant Examiner—Joyce Tung
(74) Attorney, Agent, or Firm—Fish & Richardson P.C.

(57) ABSTRACT

The invention relates to methods of evaluating transplant rejection in a host comprising determining a heightened magnitude of gene expression of genes in rejection-associated gene clusters. The disclosed gene clusters include genes that are substantially co-expressed with cytotoxic lymphocyte pro-apoptotic genes, cytoprotective genes and several other cytokine and immune cell genes.

17 Claims, 19 Drawing Sheets

OTHER PUBLICATIONS

Cooper, et al. *A20 Blocks Endothelial Cell Activation through a NF-κB–dependent Mechanism.* Journal of Biological Chemistry 271(30):18068–18073 (1996).

Cooper, et al. *A20 Expression Inhibits Endothelial Cell Activation.* Transplantation Proceedings, Barcelona, Aug. 1996.

DeBruyne, et al. *Gene Transfer of Immunomodulatory Peptides Correlates with Heme Oxygenase–1 Induction and Enhanced Allograft Survival.* Transplantation 69(1):120–128 (2000).

Dong, et al. *Heme Oxygenase–1 in Tissue Pathology.* American Journal of Pathology 156(5):1485–1488 (2000).

Ferran, et al. *A20 Inhibits NF-κB Activation in Endothelial Cells Without Sensitizing to Tumor Necrosis Factor–Mediated Apoptosis.* Blood 91(7):2249–2258 (1998).

Gaber, et al. *Correlation of histology to clinical rejection reversal: A Thymoglobulin Multicenter Trial report.* Kidney International 55:2415–2422 (1999).

Gulanikar, et al. *The incidence and inpact of early rejection episodes on graft outcome in recipients of first cadaver kidney transplants.* Transplantation 53(2):323–328 (1992).

Hancock, et al. *Antibody–induced transplant arterioslcerosis is prevented by graft expression of anti–oxidant and anti–apoptotic genes.* Nature Medicine 4(12): 1392–1396 (1998).

Hariharan, et al. *Improved graft survival after renal transplantation in the United States, 1988 to 1996.* The New England Journal of Medicine 342(9):605–612 (2000).

Henkart. *Lymphocyte–Mediated Cytotoxicity: Two Pathways and Multiple Effector Molecules.* Immunity 1:343–346 (1994).

Heusel, et al. *Cytotoxic Lymphocytes Require Granzyme B for the Rapid Induction of DNA Fragmentation and Apoptosis of Allogeneic Target Cells.* Cell 76:977–987 (1994).

Huraib, et al. *Percutaneous Needle Biopsy of the Transplanted Kidney: Technique and Complications.* American Journal of Kidney Diseases 14(1):13–17 (1989).

Kagi, et al. *Cytotoxicity mediated by T cells and natural killer cells is greatly impaired in perforin–deficient mice.* Nature 369:31–37 (1994).

Kagi, et al. *Molecular mechanims of lymphocyte–mediated cytotoxicity and their role immunological protection and pathogenesis in vivo.* Annu. Rev. Immunol. 14:207–232 (1996).

Krams, et al. *Expression of the cytotoxic T cell mediator granzyme B during liver allograft rejection.* Transplant Immunology 3:162–166 (1995).

Lee, et al. *Overexpression of heme oxygenase–1 in human pulmonary epithelial cells results in cell growth arrest and increased resistance to hyperoxia.* Proc. Natl. Acad. Sci. USA 93:10303–10398 (1996).

Legros–Maida, et al. *Granzyme B and perforin can be used as preductive markers of acute rejection in heart transplantation.* Eur. J. Immunol. 24:229–233 (1994).

Lin, et al. *Accomodated Xenografts Survive in the Presence of Anti–Donor Antibodies and Complement That Precipitate Rejection of Naive Xenografts.* Journal of Immunology 163:2850–2857 (1999).

Lindholm, et al. *The impact of actue rejection episodes on long–term graft function and outcome in 1347 primary renal transplants treated by 3 cyclosporine regimens.* Transplantation 56(2):307–315 (1993).

Lipman, et al. *Heightened Intraraft CTL Gene Expression in Acutely Rejecting Renal Allografts.* Journal of Immunology 152:5120–5127 (1994).

Littel, et al. *SAS® System for Mixed Models.* SAS Institute Inc. (1996).

Liu, et al. *Perforin: structure and function.* Immunology Today 16(4):194–201 (1995).

Maines. *The Heme Oxygenase System: A regulator of second messenger gases.* Annu. Rev. Pharmaco. Toxicol. 37:517–554 (1997).

Nath, et al. *Induction of Heme Oxygenase is a Rapid, Protective Response in Rhabdomyolysis in the Rat.* J. Clin. Invest. 90:267–270 (1992).

Nath, et al. *The Indispensability of Heme Oxygenase–1 in Protecting against Acute Heme Protein–Induced Toxicity in Vivo.* American Journal of Pathology 156(5):1527–1535 (2000).

Nicholson, et al. *A prospective randomized trial of three different sizes of core–cutting needle for renal transplant biopsy.* Kidney International 58:390–395 (2000).

Ohta, et al. *Tubular Injury as a Cardinal Pathologic Feature in Human Heme Oxygenase–1 Deficiency.* American Journal of Kidney Diseases 35(5):863–870 (2000).

Opipari, et al. *The A20 cDNA Induced by Tumor Necrosis Factor α Encodes a Novel Type of Zinc Finger Protein.* Journal of Biological Chemistry 265(25):14705–14708 (1990).

Opipari, et al. *The A20 Zinc Finger Protein Protects Cells from Tumor Necrosis Factor Cytotoxicity.* Journal of Biological Chemistry 267(18):12424–12427 (1992).

Otterbein, et al. *Carbon monoxide has anti–inflammatory effect involving the mitogen–activated protein kinase pathway.* Nature Medicine 6(4):422–428 (2000).

Racusen, et al. *The Banff 97 working classification of renal allograft pathology.* Kidney International 55:713–723 (1999).

Rush, et al. *Histological finding in early routing biopsies of stable renal allograft recipients.* Transplantation 57(2):208–211 (1994).

Rush, et al. *Beneficial Effects of Treatment of Early Subclinical Rejection: A Randomized Study.* J. Am. Soc. Nephrol. 9:2129–2134 (1998).

Sarma, et al. *Activation of the B–cell Surface Receptor CD40 Induces A20, a Novel Zinc Finger Protein That Inhibits Apoptosis.* Journal of Biological Chemistry 270–21:12343–12346 (1995).

Schulz, et al. *Acute rejection of vascular heart allografts by perforin–deficient mcie.* Eur. J. Immunol. 25:474–480 (1995).

Sharma, et al. *Molecular Executors of Cell Death–Differential Intrarenal Expression of Fas Ligand, Fas, Granzyme B, and Perforin during acute and/or chronic rejection of human renal allografts.* Transplantation 62(12):1860–1866 (1996).

Shoskes, et al. *Deleterious effects of delayed graft function in cadaveric renal transplant recipients independent of acute rejection.* Transplantation 66(12):1697–1701 (1998).

Smyth, *Dual mechanisms of lymphocyte–mediated cytotoxicity serve to control and deliver the immune response.* Bioessays 17(10):891–898 (1995).

Smyth, et al. *Granzymes: exogenous proteinases that induce target cell apoptosis.* Immunology Toda 16(4):202–206 (1995).

Soares, et al. *Expression of heme oxygenase–1 case determine cardiac xenograft survival.* Nature Medicine 4(9):1073–1077 (1998).

Sorof, et al. *Histopathological concordance of paired renal allograft biopsy cores.* Transplantation 60(11):1215–1219 (1995).

Strehlau, et al. *Quantitative detection of immune activation transcripts as a diagnostic tool in kidney transplantation.* Proc. Natl. Acad. Sci. USA 94:695–700 (1997).

Strom, et al. *Identity and cytotoxic capacity of cells infiltrating renal allografts.* New England Journal of Medicine 292(24):1257–1263 (1975).

Suthanthiran, et al. *Excellent outcome with a calcium channel blocker–supplemented immunosuppressive regimen in cadaveric renal transplantation.* Transplantation 55(5):1008–1013 (1993).

Suthanthiran, et al. *Renal Transplantation.* New England Journal of Medicine 331(6):365–376 (1994).

Tewari, et al. *Lymphoid expression and regulation of A20, and inhibitor of programmed cell death.* Journal of Immunology 154:1699–1706 (1995).

Vogt, et al. *Glomerular Inflammation Induces Resistance to Tubular Injury in the Rat.* J. Clin. Invest. 98:2139–2145 (1996).

Willis, et al. *Heme oxygenase: a novel target for the modulation of the inflammatory response.* Nature Medicine 2(1):87–90 (1996).

Yachie, et al. *Oxidative stress causes enhanced endothelial cell injury in human heme oxygenase–1 deficiency.* Journal of Clinical Investigation 103(1):129–135 (1999).

Yoshida, et al. *Human heme oxygenase cDNA and induction of its mRNA by hemin.* Eur. J. Biochem. 171:457–461 (1988).

Cassol, et al. *Primer–mediated Enzymatic Amplification of Cytomegalovirus (CMV) DNA.* J. Clin. Invest. 83:1109–1115 (Apr. 1989).

Eisen, et al. *Cluster analysis and display of genome–wide expression patterns.* Proc. Natl. Acad. Sci. USA 95:14863–14868 (1998).

Meyer–Konig, et al. *Human Cytomegalovirus Immediate Early and Late Transcripts in Peripheral Blood Leukocytes: Diagnostic Value in Renal Transplant Recipients.* Journal of Infection Diseases 171:705–709 (1995).

Lipman, et al. *Hightened Intragraft CTL Gene Expression in Acutely Rejecting Renal Allografts.* Journal of Immunology 152:1520 (1994).

Perou, et al. *Molecular portraits of human breast tumors.* Nature 406:747–752 (2000).

Ross, et al. *Systematic variation in gene expression patterns in human cancer cell lines.* Nature Genetics 24:227–235 (2000).

Rush, et al. *Sequential protocol biopsies in renal transplant patients.* Transplantation 59(4):511–514 (1995).

Rush, et al. *Histological findings in early routine biopsies of stable renal allograft recipients.* Transplantation 57(2):208–211 (1994).

Wright, et al. *The polymerase chain reaction: miracle or mirage? A critical review of its uses and limitations in diagnosis and research.* Journal of Pahtology 162:99–117 (1990).

\* cited by examiner

| GENE | SIZE cDNA AND CT (BP) | METHOD FOR CT | OLIGONUCLEOTIDE SIZE | DIRECTION | SEQUENCE 5' TO 3' | GENE ACC. NO. |
|---|---|---|---|---|---|---|
| GAPDH | 496 | ENZYME HPA II | 20 | SENSE | GGTGAAGGTCGGAGTCAACG | J04038 |
| CT | 442 | | 20 | ANTISENSE | CAAAGTTGTCATGGATGACC | |
| IL-2 | 149 | INSERT DNA | 20 | SENSE | CCTCTGGAGGAAGTGCTAAA | K02056 |
| CT | 178 | | 20 | ANTISENSE | ATGGTTGCTGTCTCATCAGC | |
| IL-4 | 227 | PRIMER DELETION | 21 | ANTISENSE | TTCTACAGCCACCATGAGAAG | M23442 |
| CT | 159 | | 22 | SENSE | CAGCTCGAACACTTTGAATAT | |
| IL-7 | 516 | 4-PRIMER | 25 | SENSE | TTTAGTATATCTTTGGACTTCCTC | J04156 |
| CT | 418 | | 21 | ANTISENSE | GTGTTCTTTAGTGCCCATCAA | |
| IL-8 | 271 | DOUBLE SENSE | 22 | SENSE | TCTCTTGGCAGCCTTCCT | M68932 |
| CT | 242 | | 25 | ANTISENSE | AATTCTCAGCCCTCTTCAAAAACTT | |
| IL-10 | 617 | ENZYME SSP1 | 18 | SENSE | GCCGTGGAGCAGGTGAAG | X78437 |
| CT | 518 | | 18 | ANTISENSE | AAGCCCAGAGACAAGATA | |
| IL-15 | 409 | ENZYME BSTBI | 20 | SENSE | CCGTGGCTTTGAGTAATGAG | X91233 |
| CT | 339 | | 19 | ANTISENSE | CAGATTCTGTTACATTCCC | |
| IL-17 | 471 | ENZYME ECO01091 | 17 | SENSE | GGAGGCCATAGTGAAGG | U32659 |
| CT | 416 | | 17 | ANTISENSE | GGGTCGGCTCTCCATAG | |
| PERFORIN | 369 | ENZYME AVA II | 17 | SENSE | CGGCTCACACTCACAGG | M31951 |
| CT | 267 | | 18 | ANTISENSE | CTGCCGTGGATGCCTATG | |
| GRANZYME B | 431 | ENZYME DDE I | 24 | SENSE | GGGGAAGCTCCATAAATGTCACCT | M28879 |
| CT | 358 | | 24 | ANTISENSE | TACACACAAGAGGGCCTCCAGAGT | |
| FAS-LIGAND | 321 | 4-PRIMER | 18 | SENSE | GCCTGTGTCTCCTTGTGA | U11821 |
| CT | 236 | | 18 | ANTISENSE | GCCACCCTTCTTATACTT | |
| TGF-β1 | 246 | INSERT DNA | 20 | SENSE | CTGCGGATCTCTGTGTCATT | X14885-91 |
| CT | 290 | | 20 | ANTISENSE | CTCAGAGTGTTGCTATGGTG | |
| IFN-γ | 510 | ENZYME ALU I | 22 | SENSE | CCAGAGCATCAAAAGAGTGTG | A02137 |
| CT | 422 | | 22 | ANTISENSE | CTAGTTGGCCCCTGAGATAAAG | |
| CTLA4 | 529 | 4-PRIMER | 20 | SENSE | GCAATGCACGTGGCCAGCC | M28879 |
| CT | 459 | | 22 | ANTISENSE | TTTCACATTCTGGCTCTGTTGG | |
| RANTES | 239 | DOUBLE SENSE | 20 | SENSE | CGGCACGCCTCGCTGTCATC | M21121 |
| CT | 204 | | 19 | ANTISENSE | TGTACTCCCGAACCCATTT | |

FIG. 1

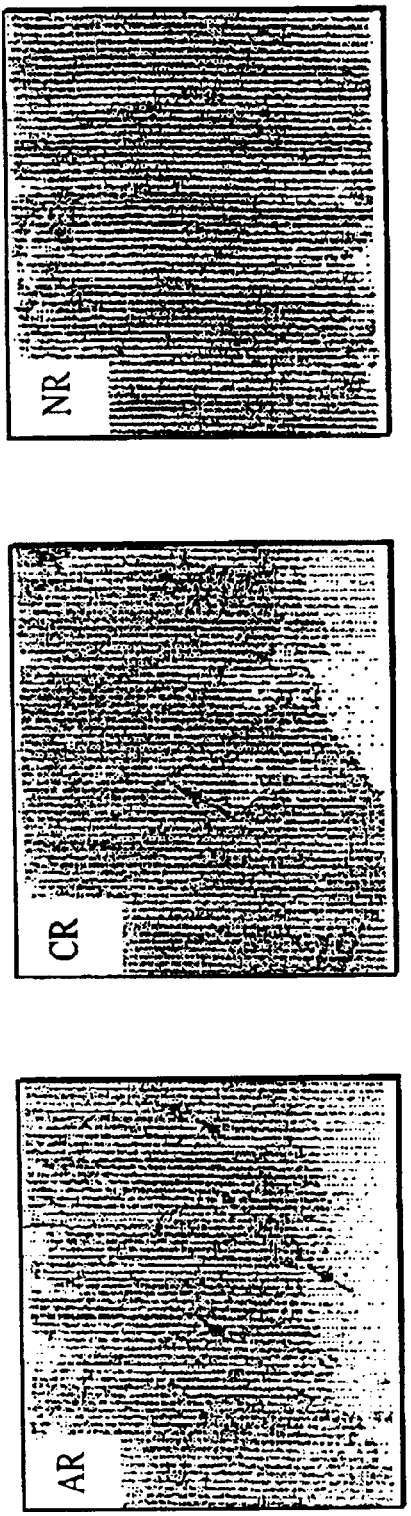

| HO-1 | AR ACUTE REJECTION |
|---|---|
| ENDOTHELIAL | + |
| TUBULAR | + |
| INFILTRATING | + |

| HO-1 | CR CHRONIC REJECTION |
|---|---|
| ENDOTHELIAL | − |
| TUBULAR | − |
| INFILTRATING | − |

| HO-1 | NR NONREJECTION |
|---|---|
| ENDOTHELIAL | − |
| TUBULAR | − |
| INFILTRATING | − |

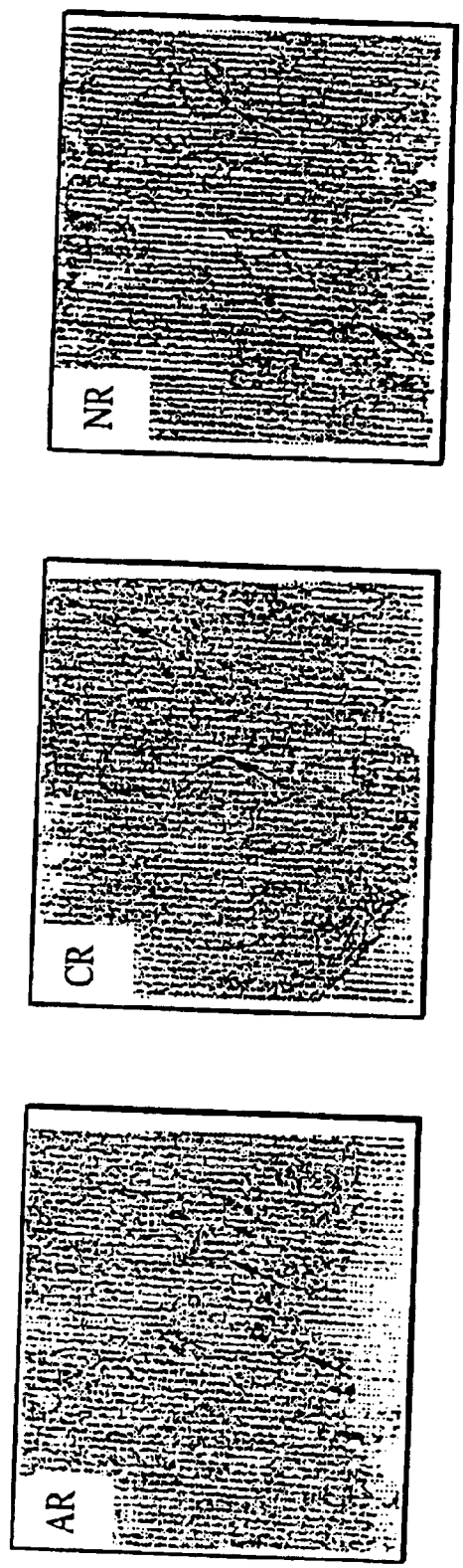

MEASUREMENT OF PROTECTIVE GENES IN ALLOGRAFT REJECTION

CLAIM OF PRIORITY

This application claims priority to U.S. Provisional Application 60/199,327, filed Apr. 24, 2000; 60/238,718, filed Oct. 6, 2000; 60/239,635, filed Oct. 12, 2000; and 60/240,735, filed Oct. 16, 2000. The contents of these applications are herein incorporated by reference.

BACKGROUND OF THE INVENTION

Acute rejection, despite clinical application of potent immunoregulatory drugs and biologic agents, remains a common and serious post-transplantation complication. It is also a risk factor for chronic rejection, a relentlessly progressive process. As the occurrence of acute rejection episodes is the most powerful predictive factor for the later development of chronic rejection in adults and children, many advocate strategies to detect and ablate acute rejection episodes as early as possible. However, current monitoring and diagnostic modalities may be ill-suited to the diagnosis of acute rejection at an early stage.

For example, acute renal allograft rejection is currently diagnosed following percutaneous needle core biopsy of the allograft. The invasive biopsy procedure, in most instances, is performed following an increase in serum creatinine. Whereas increased serum creatinine levels are currently the best surrogate markers of acute rejection, they lack sensitivity and specificity with respect to predicting rejection. The limitations associated with monitoring an immune disease (allograft rejection) with a physiologic surrogate marker such as serum creatinine have been brought to light most forcefully by the recent demonstrations that almost 30% of allograft biopsies performed in renal allograft recipients with stable renal function and an equivalent percentage of allografts successfully treated with anti-rejection drugs reveal authentic histologic features of acute rejection. These occult rejections, unmasked by protocol biopsies and unattended by clinical signs such as an increase in serum creatinine levels, appear biologically relevant since treatment has been shown to preserve renal allograft structure and function.

Procedures to diagnose allograft rejection generally depend upon detection of graft dysfunction and the presence of a mononuclear leukocytic infiltrate. However, the presence of a modest cellular infiltrate is often not conclusive and can be detected in non-rejecting grafts. It would be helpful to have a reliable tool for diagnosis and follow-up of acute allograft rejection. Repetitive samplings of the allograft, while ideal from a diagnostic perspective, are constrained by a number of practical considerations including the morbidity associated with the invasive procedure of needle core biopsies. Thus, a major objective in the transplantation field is to develop non-invasive biomarker(s) of allograft rejection. Examples of progress towards this important goal are the observations that flow immunocytometry of urinary cells and quantification of cytotoxic lymphocytic gene expression in peripheral blood leukocytes are informative regarding renal allograft status.

It would further be desirable to have methods and kits available for diagnosis of early allograft rejection. By the time rejection is well-established or is clinically diagnosable, it may be too late to salvage optimal allograft function.

Techniques for diagnosing rejection are desirable for all allografts, including but not limited to kidney, heart, lung, liver, pancreas, bone, bone marrow, bowel, nerve, stem cells, transplants derived from stem cells, tissue component and tissue composite.

The information yielded by classic biopsy analysis may not provide early indication of an impending rejection episode. It would be desirable to have methods and kits available that could supplement the data available from biopsies or that could provide earlier information than biopsies to guide therapies or to predict rejection. It would further be desirable to provide diagnostic tests that would discriminate between rejection and other tissue abnormalities in the transplanted host that may be related to infection or to drug reaction. For example, high-dose anti-rejection immunosuppressive treatment is an important contributor to post-transplant morbidity and mortality. Differentiating rejection from other pathophysiological events would permit appropriate therapies to be provided to the host, either to address the early rejection or to treat other conditions or to modify an existing therapeutic regimen.

Elegant studies of experimental and clinical allografts have yielded insights into immune mechanisms of rejection. Donor specific cytotoxic T lymphocytes (CTL) have been eluted from human allografts undergoing rejection. Molecular analyses of the effector mechanisms of cytotoxic cells have demonstrated the participation of perforin and granzyme B in the lytic machinery. mRNA encoding these cytotoxic attack molecules have been detected within renal, hepatic, pulmonary or cardiac grafts undergoing acute rejection.

Furthermore, it has been demonstrated that protective genes, such as A20, Bcl-$X_L$, and Heme oxygenase-1 (HO-1) are expressed during endothelial cell (EC) activation in order to counteract the pro-inflammatory genes and prevent EC apoptosis. In vivo data show that expression of protective genes in the transplant can promote graft survival. A20 is an anti-apoptotic gene in endothelial cells that inhibits TNF-mediated apoptosis. In addition to its anti-apoptotic role, it also inhibits NF-κB activation, helping to prevent the proinflammatory consequences of EC activation.

Heme oxygenase-1 (HO-1) is an inducible isoform of heme oxygenase which is the rate-limiting enzyme in the catabolism of heme to yield biliverdin, free iron and carbon monoxide. The biological effects of HO-1 products show important anti-oxidant, anti-inflammatory, and cytoprotective functions. Induction of HO-1 has also been demonstrated in acute rejection of renal allograft in mice. HO-1 expression is clearly associated with prolongation of xenograft survival as well as protection allograft blood vessels against arterioclerosis.

To date, virtually all studies of protective gene expression and regulation have been conducted in experimental studies and little is known about the expression of these genes in clinical transplantation.

It would be desirable to identify gene- or protein-based tests that would apply these mechanisms to the clinical diagnosis of rejection, especially in its early and/or preclinical state.

SUMMARY OF THE INVENTION

The present invention relates to methods and compositions for monitoring the status of and for treating a transplanted organ in a host. In certain aspects, the present invention relates to evaluating transplant rejection in a host by determining the magnitude of gene expression in a post-transplant biological sample obtained from the host and comparing the relative expression of the marker genes to a baseline level of expression of the immune activation marker, Upregulation of gene expression (i.e., increased or heightened gene expression) of two or more selected genes in the sample indicates rejection, and downregulation of gene expression is indicative of a non-rejection state. In one aspect, the invention relates to the detection of immune activation genes such as perforin (P), granzyme B (GB), and Fas ligand (FasL). Immune activation genes are also referred to herein as cytotoxic lymphocyte (CTL) effector molecules. In another aspect, the invention relates to the detection of cytoprotective genes such as heme oxygenase-1 and A20.

In other aspects, the invention relates to clusters of genes whose expression levels are indicative of transplant rejection. In one embodiment, the invention provides a method of evaluating acute transplant rejection in a host comprising detecting upregulation of the expression of at least two genes selected from one or more gene clusters in a post-transplantation fluid test sample wherein upregulated gene expression of at least two of said genes indicates acute transplant rejection. The invention provides several gene clusters including: the pro-apoptotic cluster, the cytoprotective cluster, the IL-7/17 cluster, the IL-8 cluster, the IL-10 cluster, the IL-15 cluster, and the T cell cluster.

The methods described herein are particularly useful for detecting acute transplant rejection and preferably early acute transplant rejection. Most typically, the host (i.e., the recipient of a transplant) is a mammal, such as a human. The transplanted organ can include any transplantable organ or tissue, for example kidney, heart, lung, liver, pancreas, bone, bone marrow, bowel, nerve, stem cells (or stem cell-derived cells), tissue component and tissue composite. In other embodiments, methods are provided for detecting chronic rejection and for classifying and treating delayed graft function.

In certain embodiments, the post-transplant biological sample (or test sample) from the host can be any biological sample comprising cells expressing the RNA (i.e. transcripts) of interest, or samples comprising RNA of interest or proteins and fragments thereof encoded by genes of interest. For example, the sample can be a tissue biopsy sample, or a peripheral blood sample containing mononuclear cells, or a urine sample containing urinary cells. Additionally, the sample can be urine sediment, lymphatic fluid, peritoneal fluid, pleural fluid, bronchoalveolar lavage fluid, pericardial fluid, gastrointestinal juice, bile, feces, tissue fluid or swelling fluid, joint fluid, cerebrospinal fluid, or any other named or unnamed fluid gathered from the anatomic area in proximity to the allograft or any fluid in fluid communication with the allograft. The tissue biopsy sample can be allograft tissue or xenograft tissue. In one embodiment of the present invention, the sample is obtained from a renal allograft. In another embodiment, the sample is obtained from a cardiac allograft or a composite heart-lung allograft.

In certain embodiments, the magnitude of expression of the indicator genes is determined by quantifying marker gene transcripts and comparing this quantity to the quantity of transcripts of a constitutively expressed gene. The term "magnitude of expression" means a "normalized, or standardized amount of gene expression". For example, the overall expression of all genes in cells varies (i.e., is not constant). To accurately assess whether the detection of increased mRNA transcript is significant, it is preferable to "normalize" gene expression to accurately compare levels of expression between samples. Normalization may be accomplished by determining the level of expression of the gene of interest (e.g., determining gene mRNA or cDNA transcribed from the gene mRNA) and the level of expression of a universally, or constitutively expressed gene (e.g., a gene that is present in all tissues and has a constant level of expression), and comparing the relative levels of expression between the target gene (gene of interest) and the constitutively expressed gene. In one embodiment, the constitutively expressed gene is glyceraldehyde-3-phosphate dehydrogenase (GAPDH). In a further embodiment, the constitutively expressed gene is cyclophilin B. Other constitutively expressed genes, such as actin, are known to those of skill in the art and can be suitable for use in the methods described herein. In exemplary methods described herein, quantification of gene transcripts was accomplished using competitive reverse transcription polymerase chain reaction (RT-PCR) and the magnitude of gene expression was determined by calculating the ratio of the quantity of gene expression of each marker gene to the quantity of gene expression of the constitutively expressed gene. That is, the magnitude of target gene expression is calculated as pg of target gene cDNA per pg of constitutively-expressed gene cDNA. In other embodiments, gene expression is measured by binding of cDNA or mRNA or fragments thereof to a nucleotide array, and preferably a microarray. In preferred embodiment the cDNA, mRNA or fragments are labeled for easier detection.

In one embodiment, the discriminatory level for heightened gene expression (e.g., the baseline magnitude of gene expression) of the immune activation marker gene is set to the mean±95% confidence interval of a group of values observed in nonrejecting transplants (e.g., control values). Heightened gene expression is determined as above a mean±95% confidence interval of these values.

In other embodiments, sequential samples can be obtained from the host and the quantification of immune activation gene markers determined as described herein, and the course of rejection can be followed over a period of time. In this case, for example, the baseline magnitude of gene expression of the immune activation marker genes is the magnitude of gene expression in a post-transplant sample taken very shortly after the transplant. For example, an initial sample or samples can be taken within the nonrejection period, for example, within one week of transplantation and the magnitude of expression of marker genes in these samples can be compared with the magnitude of expression of the genes in samples taken after one week. In one embodiment, the samples are taken on days 0, 3, 5, 7 and 10.

In another embodiment, the post-transplant test sample comprises a blood sample obtained from the host, the sample contains peripheral blood mononuclear cells (PBMCs) and is evaluated for the marker genes. Additionally, the PBMC sample is substantially simultaneously, or sequentially, evaluated for the presence or absence of one or more genes that are characteristic of (e.g., a marker for) an infectious agent (e.g., a virus). In certain embodiments, heightened expression of one, two or more genes of any of the gene clusters of Table 1, concomitant with the absence of the marker for the infectious agent indicates transplant rejection. In one embodiment, heightened gene expression of two of the three immune activation marker genes, P, GB and FasL, concomitant with the absence of the marker for the infectious agent indicates acute transplant rejection. In another embodiment, heightened expression of genes belonging to the various clusters, concomitant with the absence of the marker for the infectious agent indicates transplant rejection. For example, to evaluate acute transplant rejection of a renal allograft, the genes characteristic of the infectious agent cytomegalovirus (CMV) would be assessed. Importantly, this embodiment acts as a screening test, using easily obtained PBMCs, to differentially distinguish between acute rejection of the transplant or infection. In this case, further testing, such as with a transplant biopsy sample, will only be performed if the initial "screening" test using PBMCs is positive for rejection. Thus, transplant hosts are not submitted to invasive biopsy procedures unless it is justified (i.e., necessary to establish rejection).

In another embodiment, the post-transplant test sample comprises a fluid secreted or excreted by the functioning allograft, for example, bile from a liver transplant, gastrointestinal juice from a gastrointestinal transplant, or urine from a renal transplant. In another embodiment, the post-transplant test sample comprises exudative or transudative fluid emanating from the allograft, such as pleural, peritoneal or joint fluid, or exudative or transudative fluid retrieved from the allograft using techniques including aspiration or lavage, for example, bronchoalveolar lavage in lung transplants or joint aspiration in a composite tissue transplant.

In certain embodiments, the biological sample is prepared for evaluation by isolating RNA from the sample, using methods described herein, and deriving (obtaining) complementary DNA (cDNA) from the isolated RNA by reverse transcription techniques. However, other methods can be used to obtain RNA, and these methods are known to those of skill in the art.

In certain embodiments, the proteins encoded by any of the genes that are members of gene clusters described herein may be detected, and elevated protein levels may be used to diagnose graft rejection. In preferred embodiments, protein levels are detected in a post-transplant fluid sample, and in a particularly preferred embodiment, the fluid sample is peripheral blood or urine. Normalization of protein levels may be performed in much the same way as normalization of transcript levels. One or more constitutively or universally produced proteins may be detected and used for normalization.

The methods described herein are useful to assess the efficacy of anti-rejection therapy. Such methods involve comparing the pre-administration magnitude of the transcripts of the marker genes to the post-administration magnitude of the transcripts of the same genes, where a post-administration magnitude of the transcripts of the genes that is less than the pre-administration magnitude of the transcripts of the same genes indicates the efficacy of the anti-rejection therapy. Any candidates for prevention and/or treatment of transplant rejection, (such as drugs, antibodies, or other forms of rejection or prevention) can be screened by comparison of magnitude of marker expression before and after exposure to the candidate. In addition, valuable information can be gathered in this manner to aid in the determination of future clinical management of the host upon whose biological material the assessment is being performed. The assessment can be performed using a biological sample from the host, using the methods described herein for determining the magnitude of gene expression of the marker genes. Analysis can further comprise detection of an infectious agent.

Yet another object of the invention is to provide methods for treating a transplantation-related condition in a host, such as a rejection, for example a treatable rejection state. Such methods may comprise determining the magnitude of gene expression of genes found in a post-transplantation sample wherein the magnitude of expression indicates the likelihood of a treatable rejection state. A therapy is selected based on the likelihood of a treatable rejection state, wherein said therapy will comprise adding to the host's baseline therapeutic regimen a therapeutically effective dose of an anti-rejection agent if a treatable rejection state is likely, and said therapy will comprise not adding to the host's baseline therapeutic regimen the therapeutically effective dose of the anti-rejection agent if a treatable rejection state is unlikely. In certain embodiments, the method involves determining the magnitude of two or more genes selected from one or more gene clusters, said one or more gene clusters being selected from the group consisting of: the pro-apoptotic cluster, the cytoprotective cluster, the IL-7/17 cluster, the IL-8 cluster, the IL-10 cluster, the IL-15 cluster, and the T cell cluster. These methods, involving determining the magnitude of two or more genes selected from one or more gene clusters, said one or more gene clusters being selected from the group consisting of: the pro-apoptotic cluster, the cytoprotective cluster, the IL-7/17 cluster, the IL-8 cluster, the IL-10 cluster, the IL-15 cluster, and the T cell cluster are also applicable to the treatment of other transplant related conditions not involving rejection, as will be appreciated by those of skill in the art The present invention also relates to kits for evaluating transplant rejection. For instance, the kits can include such components as means to aid in RNA isolation, cDNA derivation, RT-PCR, quantification of gene expression, and detection of an infectious agent. In one embodiment, a kit for detecting the presence of transplant rejection in a blood sample comprises means for determining the magnitude of expression of perforin, granzyme B, Fas ligand, and GAPDH in the sample and means for determining the presence of infectious agent transcripts in the sample. For example, the kit can comprise oligonucleotide primers comprising SEQ ID NOS: 1, 2, 17, 18, 19, 20, 21 and 22. Other kits of the invention may comprise means for determining the magnitude of expression of one or more cytoprotective genes, such as heme oxygenase 1 or A20. For example, the kit can comprise oligonucleotide primers selected from the group consisting of SEQ ID NOS: 33–41. The kit may also contain other primers which can be designed using methods well-known to those of skill in the art.

Thus, as a result of the work described herein, methods are now available to accurately quantitate marker gene expression in biopsy tissue, urine, peripheral blood mononuclear cells and other body fluids, and to correlate the magnitude of expression of these genes with rejection of allografts. Surprisingly, the evaluation of the expression of marker genes in a post-transplant sample, along with the evaluation of expression of an infectious agent gene, also accurately detects allograft rejection.

BRIEF DESCRIPTION OF THE DRAWINGS

FIG. 1 is a chart that depicts the size and sequences of oligonucleotide primers SEQ ID NOs 1–30 respectively and competitive templates (CTs) used for the quantification of 15 genes. Deletions and insertions are indicated by black and white portions of bars, respectively.

DETAILED DESCRIPTION OF INVENTION

General

Figure 2A:
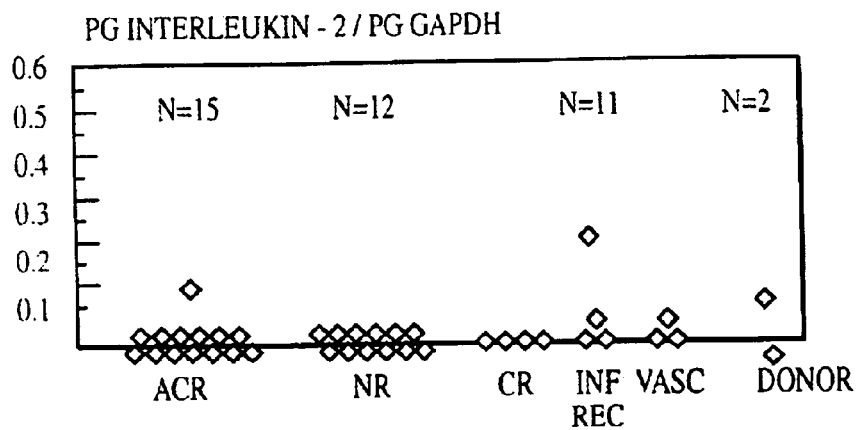
FIGS. 2A–F are graphs that depict the quantitative analysis of IL-2, IL-7, IL-15, perforin (P), granzyme B (GB), and Fas Ligand (FasL) gene expression in 38 transplant core biopsies taken to aid in the differential diagnosis of graft dysfunction. Biopsies were also obtained from two donor kidneys prior to reperfusion. Lines indicate sequential biopsies taken during the course of rejection before and after treatment (ACR, acute cellular rejection; NR, nonrejecting kidneys with acute tubular necrosis or cyclosporine cytotoxicity; CR, chronic rejection; INF REC, infectious complications and recurrence of primary disease; and VASC, vascular complications).
Figure 2B:
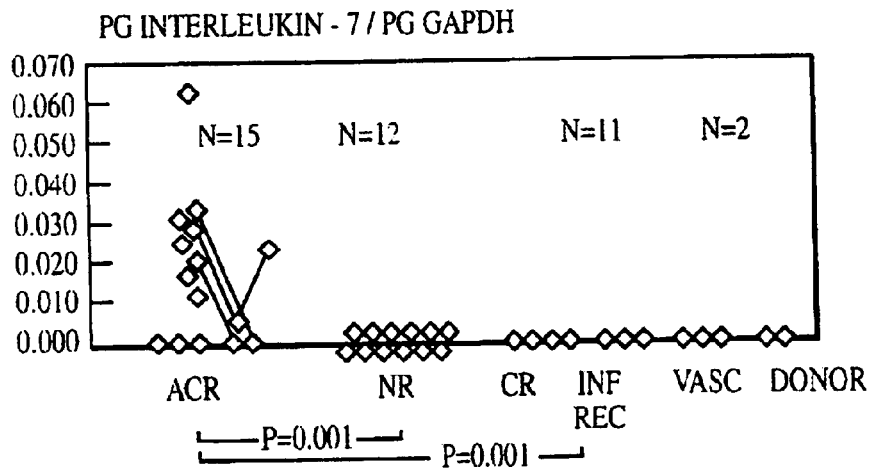
Figure 2C:
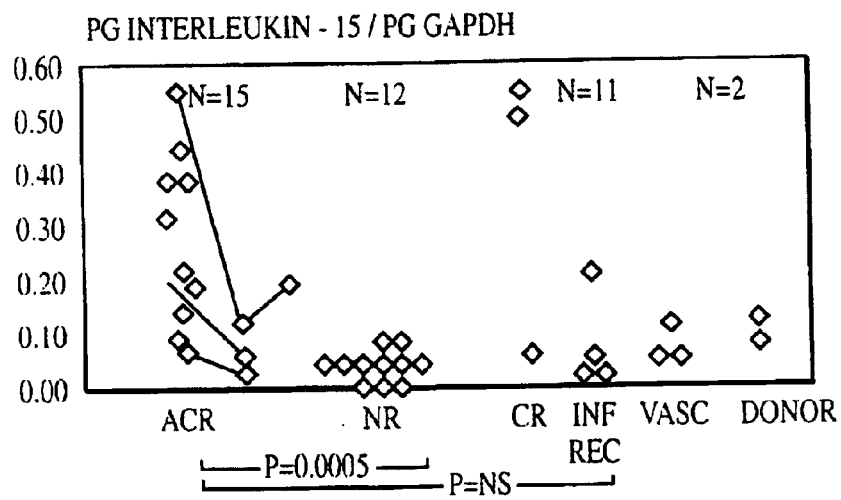
Figure 2D:
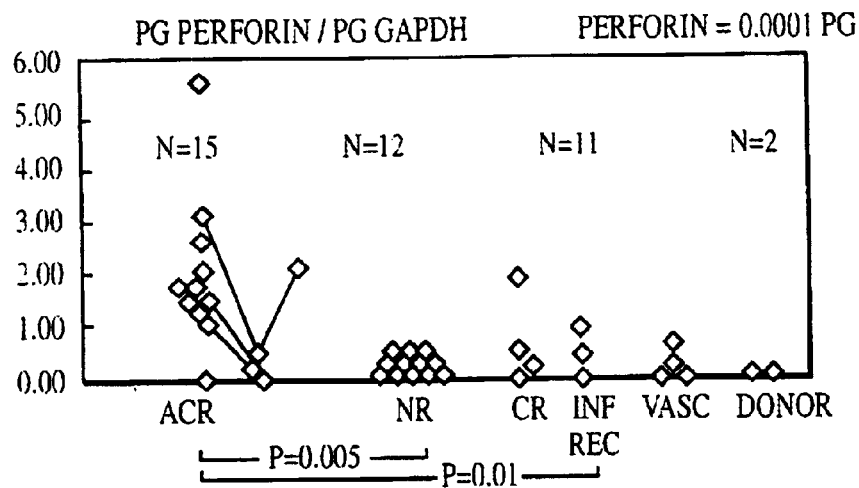
Figure 2E:
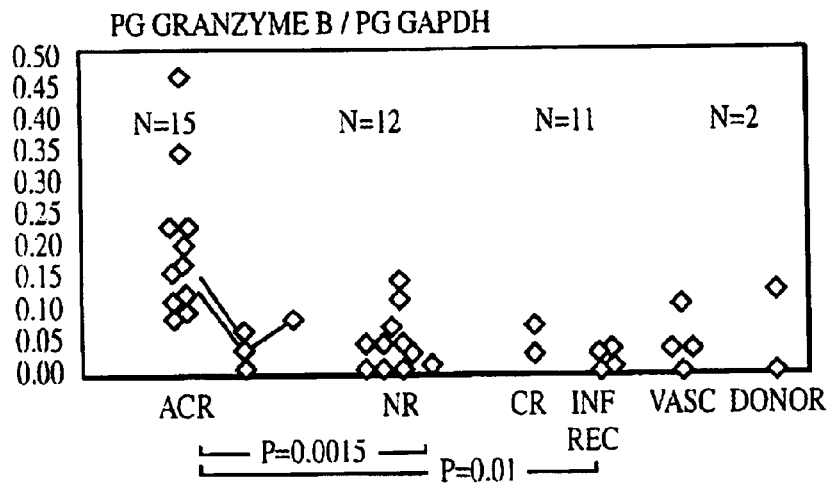
Figure 2F:
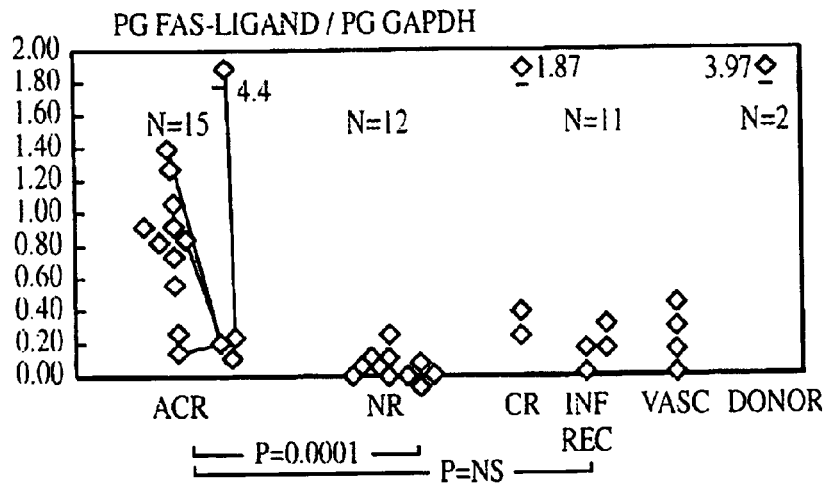

The single most common cause for early graft failure, especially within one month post-transplantation, is immunologic rejection of the allograft. The unfavorable impact of the rejection is magnified by the fact that: (a) the use of high-dose anti-rejection therapy, superimposed upon maintenance immunosuppression, is primarily responsible for the morbidity and mortality associated with transplantation, (b) the immunization against "public" HLA-specificities resulting from a rejected graft renders this patient population difficult to retransplant and (c) the return of the immunized recipient with a failed graft to the pool of patients awaiting transplantation enhances the perennial problem of organ shortage.

Antigen-triggered T-cell activation and the subsequent infiltration of activated CD4+ and CD8+ T-cell clones, macrophages, and natural killer (NK) cells into the graft are key events of acute allograft rejection. However a biopsy result indicating T-cell invasion into a transplant is not sufficient for a confident diagnosis. For example, although a T-cell-rich interstitial nephritis is a hallmark of acute renal allograft rejection, clinical rejection episodes responsive to treatment often show only a modest cellular infiltrate and similar infiltrates are observed in surveillance biopsies obtained in well-functioning renal allografts (Rush et al., *Transplantation* 57: 208–211 (1994)); (Rush et al., *Transplantation* 59: 511–514 (1994)).

The differentiation of the diagnosis of rejection from other etiologies for graft dysfunction and institution of effective therapy is further complicated because: (a) the percutaneous core needle biopsy of grafts, the best of available current tools to diagnose rejection is performed usually after the "fact", i.e., graft dysfunction and graft damage (irreversible in some instances) are already present, (b) the morphological analysis of the graft provides modest clues with respect to the potential for reversal of a given rejection episode, and minimal clues regarding the likelihood of recurrence ("rebound"), and (c) the mechanistic basis of the rejection phenomenon, a prerequisite for the design of therapeutic strategies, is poorly defined by current diagnostic indices, including morphologic features of rejection.

The diagnosis of, for example, renal allograft rejection is made usually by the development of graft dysfunction (e.g., an increase in the concentration of serum creatinine) and morphologic evidence of graft injury in areas of the graft also manifesting mononuclear cell infiltration. Two caveats apply, however, to the use of abnormal renal function as an indicator of the rejection process: first, deterioration in renal function is not always available as a clinical clue to diagnose rejection since many of the cadaveric renal grafts suffer from acute (reversible) renal failure in the immediate post-transplantation period due to injury from harvesting and ex-vivo preservation procedures. Second, even when immediately unimpaired renal function is present, graft dysfunction might develop due to a non-immunologic cause, such as immunosuppressive therapy itself.

For example, cyclosporine (CsA) nephrotoxicity, a complication that is not readily identified solely on the basis of plasma/blood concentrations of CsA, is a common complication. The clinical importance of distinguishing rejection from CsA nephrotoxicity cannot be overemphasized since the therapeutic strategies are diametrically opposite: escalation of immunosuppressants for rejection, and reduction of CsA dosage for nephrotoxicity.

The invention is based, in part, on the observation that increased or decreased expression of many different genes and/or the encoded proteins is associated with certain graft rejection states. As a result of the data described herein, methods are now available for the rapid and reliable diagnosis of acute and chronic rejection, even in cases where allograft biopsies show only mild cellular infiltrates. Described herein for the first time, analysis of cytoprotective genes transcripts, or transcripts substantially co-expressed therewith, accurately detect transplant rejection.

In addition, the invention is partly based on the observation that genes are expressed as gene clusters—groups of genes, often functionally related, that have substantially related expression profiles under certain circumstances. Accordingly, the invention provides clusters of genes, the expression of the members of which is correlated with graft rejection. The invention further provides classic molecular methods and large scale methods for measuring expression of suitable marker genes.

Definitions

An "anti-rejection agent" is any substance administered to a subject for the purpose of preventing or ameliorating a rejection state. In preferred embodiments, an anti-rejection agent excludes antibiotics, antivirals, antifungals and steroids. A "pharmacological agent" is used herein to refer to any substance administered to a patient for the purpose of preventing or ameliorating an unhealthy state but excluding anti-rejection agents.

"Baseline therapeutic regimen" is understood to include those anti-rejection agents being administered at a baseline time, subsequent to which a rejection state may be suspected. The baseline therapeutic regimen may be modified by the temporary or long-term addition of other anti-rejection agents, or by a temporary or long-term increase or decrease in the dose of one or all of the baseline anti-rejection agents.

As used herein, the term "biopsy" refers to a specimen obtained by removing tissue from living patients for diagnostic examination. The term includes aspiration biopsies, brush biopsies, chorionic villus biopsies, endoscopic biopsies, excision biopsies, needle biopsies (specimens obtained by removal by aspiration through an appropriate needle or trocar that pierces the skin, or the external surface of an organ, and into the underlying tissue to be examined), open biopsies, punch biopsies (trephine), shave biopsies, sponge biopsies, and wedge biopsies. In one embodiment, a fine needle aspiration biopsy is used. In another embodiment, a minicore needle biopsy is used. A conventional percutaneous core needle biopsy can also be used.

A "cytoprotective gene" is a gene that directly or indirectly inhibits cell death and particularly apoptotic cell death. Cytoprotective genes may be expressed in graft cells or in host cells, such as CTLs.

A "CTL effector gene" is a gene that functions in the cytotoxic activities of a CTL. For example, a CTL effector gene may be involved in causing apoptosis of target cells, either directly, as in the case of proteins such as granzyme B and perforin, or indirectly, such as by promoting expression, activation, packaging or secretion of direct effectors.

A "fluid test sample" as used herein in reference to samples obtained from a subject is intended to include essentially any fluid that can be obtained from a subject. Preferably the fluid test sample contains cells, proteins, nucleic acids or other cellular matter. A fluid test sample may also be the liquid phase of a body fluid from which sedimentary materials have been substantially removed. Exemplary fluid test samples include blood samples containing peripheral blood mononuclear cells (PBMCs), urine samples containing urinary cells, urine "supernatant" that is substantially free of cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft. A fluid test sample may also be obtained from essentially any body fluid including: blood (including peripheral blood), lymphatic fluid, sweat, peritoneal fluid, pleural fluid, bronchoalveolar lavage fluid, pericardial fluid, gastrointestinal juice, bile, urine, feces, tissue fluid or swelling fluid, joint fluid, cerebrospinal fluid, or any other named or unnamed fluid gathered from the anatomic area in proximity to the allograft or gathered from a fluid conduit in fluid communication with the allograft. A "post-transplantation fluid test sample" refers to a sample obtained from a subject after the transplantation has been performed.

As used herein the term "gene cluster" or "cluster" refers to a group of genes related by expression pattern. In other words, a cluster of genes is a group of genes with similar regulation across different conditions, such as graft non-rejection verus graft rejection. The expression profile for each gene in a cluster should be correlated with the expression profile of at least one other gene in that cluster. Correlation may be evaluated using a variety of statistical methods. Many statistical analyses produce a correlation coefficient to describe the relatedness between two gene expression patterns. Patterns may be considered correlated if the correlation coefficient is greater than or equal to 0.8. In preferred embodiments, the correlation coefficient should be greater than 0.85, 0.9 or 0.95. Other statistical methods produce a measure of mutual information to describe the relatedness between two gene expression patterns. Patterns may be considered correlated if the normalized mutual information value is greater than or equal to 0.7. In preferred embodiments, the normalized mutual information value should be greater than 0.8, 0.9 or 0.95. Often, but not always, members of a gene cluster have similar biological functions in addition to similar gene expression patterns.

A "Pro-apoptotic gene cluster" or "pro-apoptotic cluster" is the cluster of genes exemplified by FasL, granzyme B and perforin. Members of this gene cluster have expression patterns in rejection versus non-rejection transplant samples that are substantially related to the expression patterns for FasL, granzyme B or perforin. Members of this gene cluster are not necessarily functionally related to FasL, granzyme B or perforin.

A "Cytoprotective gene cluster" or "cytoprotective cluster" is the cluster of genes exemplified by A20 and HO1.

Members of this gene cluster have expression patterns in rejection versus non-rejection transplant samples that are substantially related to the expression patterns for A20 and HO1. Members of this gene cluster are not necessarily functionally related to A20 and HO1.

An "IL-7/17 gene cluster" or "IL-7/17 cluster" or "maturation cytokine cluster" is the cluster of genes exemplified by IL-7 and IL-17. Members of this gene cluster have expression patterns in transplant samples that are substantially related to the expression patterns for IL-7 and IL-17. Members of this gene cluster are not necessarily functionally related to IL-7 or IL-17.

An "IL-8 gene cluster" or "IL-8 cluster" or "extravasation cytokine cluster" is the cluster of genes exemplified by IL-8. Members of this gene cluster have expression patterns in transplant samples that are substantially related to the expression patterns for IL-8. Members of this gene cluster are not necessarily functionally related to IL-8.

An "IL-10 gene cluster" or "IL-10 cluster" or "inhibitory cytokine cluster" is the cluster of genes exemplified by IL-10. Members of this gene cluster have expression patterns in transplant samples that are substantially related to the expression patterns for IL-10. Members of this gene cluster are not necessarily functionally related to IL-15.

An "IL-15 gene cluster" or "IL-15 cluster" or "activating cytokine cluster" is the cluster of genes exemplified by IL-15. Members of this gene cluster have expression patterns in transplant samples that are substantially related to the expression patterns for IL-15. Members of this gene cluster are not necessarily functionally related to IL-15.

A "T cell gene cluster" or "T cell cluster" is the cluster of genes exemplified by CTLA-4 and RANTES. Members of this gene cluster have expression patterns in transplant samples that are substantially related to the expression patterns for CTLA-4 and RANTES. Members of this gene cluster are not necessarily functionally related to CTLA-4 or RANTES.

As used herein, an "infectious agent" refers to any agent which plays a role in infection in a graft patient. Infectious agents include bacteria such as *Escherichia coli, Klebsiella,* Enterobacteriaceae, *Pseudomonas,* and *Enterococcus*; Fungi, such as *Candida albicans, Histoplasma capsulatum,* and *Cryptococcus;* viruses such as Hepatitis B and C viruses, human immunodeficiency virus, and herpes-group viruses, which include herpes simplex virus type 1, herpes simplex virus type 2, varicella-zoster virus (VZV), cytomegalovirus (CMV), Epstein-Barr virus (EBV), Human Herpesvirus 6, Human Herpesvirus 7, Kaposi's Sarcoma-associated virus (human herpesvirus 8), and Papovaviruses; and parasites, including, but not limited to, *Plasmodium falciparum, Toxoplasma gondii,* strongyloides, stercoralis, and *Trypanosoma cruzi.*

"Pre-administration magnitude" is used herein in reference to the magnitude of gene expression prior to administration or alteration of a therapeutic regimen. "Post-administration magnitude" is used in reference to the magnitude of gene expression after the initiation of a changed in therapeutic regimen.

A "probe set" as used herein refers to a group of nucleic acids that may be used to detect two or more genes. Detection may be, for example, through amplification as in PCR and RT-PCR, or through hybridization, as on a microarray, or through selective destruction and protection, as in assays based on the selective enzymatic degradation of single or double stranded nucleic acids. Probes in a probe set may be labeled with one or more fluorescent, radioactive or other detectable moieties (including enzymes). Probes may be any size so long as the probe is sufficiently large to selectively detect the desired gene. A probe set may be in solution, as would be typical for multiplex PCR, or a probe set may be adhered to a solid surface, as in an array or microarray. It is well known that compounds such as PNAs may be used instead of nucleic acids to hybridize to genes. In addition, probes may contain rare or unnatural nucleic acids such as inosine.

As understood herein, the term "tissue component" refers to any cellular component or composite cellular component of a larger functioning organ, such as Islets of Langerhans cells that may be transplanted, or stem cells or central nervous system cells. As understood herein, "tissue composite" refers to any structure made up of more than one tissue or cell type that may be transplanted, such as an extremity, for example a hand or an arm, or such as a joint. Engineered tissue composites, such as engineered body parts or engineered organs, may be included within the term tissue composite if they are made up of more than one tissue or cell type.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). An organ, or graft, transplanted between two genetically different individuals of the same species is called an "allograft". A graft transplanted between individuals of different species is called a "xenograft".

As used herein, "transplant rejection" is defined as functional and structural deterioration of the organ due to an active immune response expressed by the recipient, and independent of non-immunologic causes of organ dysfunction.

A "treatable rejection state" is understood to be a particular type of transplant rejection that is susceptible to amelioration by selection of appropriate therapeutic intervention, for example by administering a therapeutic agent with known anti-rejection effects. A treatable rejection state may include features of acute or chronic rejection or be a rejection at any time point in the progression from the introduction of the graft to eventual tolerance or rejection.

The "urinary system" as used herein refers to any tissue involved in the production, storage or excretion of urine. This term is also intended to encompass any assemblage of cells that is in fluid contact with urine, whether or not those cells play a role in the production, storage or excretion of urine. This term encompasses, for example, the kidneys, bladder, ureter, bladder cancers etc. A "urinary system graft" is used to mean exogenous cells that are introduced into the urinary system of a host.

Gene Clusters:

In part, the invention relates to the discovery of gene clusters that are diagnostic of acute transplant rejection and gene clusters that are diagnostic of other transplant-related conditions (see Table 1). Advances in highly parallel, automated DNA hybridization techniques combined with the growing wealth of human gene sequence information have made it feasible to simultaneously analyze expression levels for thousands of genes (see, e.g., Schena et al., 1995, Science 270:467–470; Lockhort et al., 1996, Nature Biotechnology 14:1675–1680; Blanchard et al., 1996, Nature Biotechnology 14:1649; Ashby et al., U.S. Pat. No. 5,569, 588, issued Oct. 29, 1996; Perou et al., 2000, Nature 406:747–752; ). Methods such as the gene-by-gene quantitative RT-PCR described in the Examples are highly accurate but relatively labor intensive. While it is possible to analyze the expression of thousands of genes using quantitative PCR, the effort and expense would be enormous. Instead, as an example of large scale analysis, an entire population of mRNAs may be converted to cDNA and hybridized to an ordered array of probes that represent anywhere from ten to ten thousand or more genes. The relative amount of cDNA that hybridizes to each of these probes is a measure of the expression level of the corresponding gene. The data may then be statistically analyzed to reveal informative patterns of gene expression.

The advent of large scale gene expression analysis has revealed that groups of genes are often expressed together in a coordinated manner. For example, whole genome expression analysis in the yeast Saccharomyces cerevisiae showed coordinate regulation of metabolic genes during a change in growth conditions known as the diauxic shift (DiRisi et al., 1997, Science 278:680–686; Eisen et al., 1998, PNAS 95:14863–14868). The diauxic shift occurs when yeast cells fermenting glucose to ethanol exhaust the glucose in the media and begin to metabolize the ethanol. In the presence of glucose, genes of the glycolytic pathway are expressed and carry out the fermentation of glucose to ethanol. When the glucose is exhausted, yeast cells must metabolize the ethanol, a process that depends heavily on the Krebs cycle and respiration.

Accordingly, the expression of glycolysis genes decreases, and the expression of Krebs cycle and respiratory genes increases in a coordinate manner. Similar coordinate gene regulation has been found in various cancer cells. Genes encoding proteins involved in cell cycle progression and DNA synthesis are often coordinately overexpressed in cancerous cells (Ross et al., 2000, Nature Genet. 24:227–235; Perou et al., 1999, PNAS 96:9212–9217; Perou et al., 2000, Nature 406:747–752).

The coordinate regulation of genes is logical from a functional point of view. Most cellular processes require multiple genes, for example: glycolysis, the Krebs cycle, and cell cycle progression are all multi-gene processes. Coordinate expression of functionally related genes is therefore essential to permit cells to perform various cellular activities. Such groupings of genes can be called "gene clusters" (Eisen et al., 1998, PNAS 95:14863–68).

Clustering of gene expression is not only a functional necessity, but also a natural consequence of the mechanisms of transcriptional control. Gene expression is regulated primarily by transcriptional regulators that bind to cis-acting DNA sequences, also called regulatory elements. The pattern of expression for a particular gene is the result of the sum of the activities of the various transcriptional regulators that act on that gene. Therefore, genes that have a similar set of regulatory elements will also have a similar expression pattern and will tend to cluster together. Of course, it is also possible, and quite common, for genes that have different regulatory elements to be expressed coordinately under certain circumstances.

In one exemplary embodiment, transplant rejection state may be diagnosed by detecting upregulation or downregulation of two, and preferably three, four or more genes of the "pro-apoptotic gene cluster". The "pro-apoptotic gene cluster" comprises genes that are coordinately regulated with perforin, granzyme B and/or FasL in transplant rejection samples. These three genes are coordinately regulated in transplant rejection and define a cluster of genes whose upregulation is now known to be diagnostic for acute graft rejection. In preferred embodiments, genes to be detected are members of gene cluster A and are expressed in CTLs.

In particularly preferred embodiments, the genes have pro-apoptotic functions. Rejection occurs in part because infiltrating immune cells, such as CTLs, induce apoptosis in the cells of the graft tissue, leading to necrosis and dysfunction in the graft. FasL, perforin and granzyme B are all causative agents in CTL-induced apoptosis of graft cells. It is intriguing to note that pro-apoptotic genes in particular are well-correlated with transplant rejection, while other lymphocyte-expressed genes such as IFN-γ are poorly correlated. While not wishing to be limited to a particular mechanism, it is suggested that pro-apoptotic genes generally will tend to be good markers for acute graft rejection because CTL-induced apoptosis is a critical event of acute graft rejection. In a further embodiment, the invention provides a CTL effector gene cluster comprising genes that are expressed in CTLs and function to promote apoptosis in target cells, either directly or indirectly. In preferred embodiments, detection of increased expression of two, three, four or more members of the CTL effector gene cluster is indicative of acute graft rejection.

Perforin, stored and secreted from the granules of cytotoxic effector cells, forms pores in the target cell membrane, and causes cell death. Granzyme B; expressed primarily by activated cytotoxic cells, is a serine peptidase, and is an integral member of the lytic machinery of cytotoxic cells. In the granule exocytosis model of cytotoxicity, perforin creates holes in the target cell membrane and facilitates the entry of granzyme B into the target cells. Granzymne B then induces DNA fragmentation and cell death via activation of proapoptotic caspase 3.

Experimental and clinical investigations have implicated perforin and granzyme B in allograft rejection. Mice, rendered perforin-deficient by homologous recombination, have impaired cytotoxic effector cells and are inefficient in rejecting cardiac allografts. Granzyme B-deficient mice express reduced cytolytic activity. Clinical studies suggest that acute rejection is characterized by heightened expression of cytotoxic genes within the allograft.

TABLE 1

Exemplary gene clusters

| Cluster Name | Exemplary Gene(s) |
| --- | --- |
| Pro-apoptotic cluster | Granzyme B, Perforin, FasL |
| Cytoprotective cluster | A20, HO1 |
| IL-7/17 cluster | IL-7, IL-17 |
| IL-8 cluster | IL-8 |
| IL-10 cluster | IL-10 |
| IL-15 cluster | IL-15 |
| T cell cluster | RANTES, CTLA-4 |

In a further embodiment, the invention provides cytoprotective genes that are indicative of rejection. In one exemplary embodiment, transplant rejection may be diagnosed by detecting upregulation of one, two, and preferably three, four or more "cytoprotective genes". In a particularly preferred embodiment, the cytoprotective genes to be detected do not include Bcl-$X_L$. In another embodiment, the invention provides a "cytoprotective gene cluster", comprising genes that are coordinately regulated with heme oxygenase 1 (HO1) or A20 in acute transplant rejection samples. These two genes define a cluster of genes the upregulation of which, in view of this specification, is now known to be diagnostic for graft rejection, preferably acute graft rejection. In preferred embodiments, genes to be detected are members of the cytoprotective cluster and function to inhibit or dampen apoptosis of graft tissue.

The invention further provides an "A20 chronic rejection gene cluster". A20 gene expression is significantly increased in chronic rejection relative to nonrejection. The A20 chronic rejection gene cluster comprises the A20 gene and other genes that are coordinately regulated with A20 in chronic rejection states. Detection of a member of the A20 chronic rejection cluster, and particularly in the absence of strong expression of HO-1, is diagnostic for chronic graft rejection.

A20 is a zinc finger protein originally identified as a TNF-inducible gene in human umbilical vascular endothelial cells (HUVEC) with the ability to protect cells from TNF-induced apoptosis. A20 is also expressed in a variety of cell types in response to a number of stimuli, particularly TNF-α and IL-1 which are up-regulated in graft rejection. A20 functions to protect vascular endothelial cell injury by at least two mechanisms. In addition to its anti-apoptotic role, A20 can block activation of NF-κB signaling pathway by acting upstream of IκB degradation. Therefore, A20 can prevent activation of a variety of pro-inflammatory cytokines. Moreover, expression of A20 and HO-1 is associated with long-term survival of cardiac xenograft. The expression of these genes can prevent the development of graft arteriosclerosis.

HO is a rate-limiting enzyme of heme catabolism that has 2 isoforms: HO-1, an inducible isoform, and HO-2, a constitutive isoform. HO-1 has anti-inflammatory, antioxidant and cytoprotective functions. The enzyme catalyzes the conversion of heme into biliverdin, and carbon monoxide as well as induction of ferritin synthesis. In addition, HO-1 might modulate immune effector function through heme-degradated end products. Carbon monoxide, similar to nitric oxide, acts as a potent vasodilator and inhibitor of platelet aggregation as well as causing cell cycle arrest. Biliverdin is converted, by biliverdin reductase, to bilirubin. Both biliverdin and bilirubin have potent antioxidant and anti-complement effects. Bilirubin also has been shown to inhibit intracellular enzyme, such as protein kinase C, cAMP-dependent protein kinase, and NADPH oxidase. Inhibition of such enzymes may be responsible for the inhibition of cytolytic machinery of effector cells. Bilirubin is known to inhibit cell proliferation, IL-2 production, antibody dependent and independnet cell-mediated cytotoxicity. Ferritin can sequester free iron and prevent free iron from participating in subsequent oxidative injury.

It is surprising that high expression levels of one or more cytoprotective genes are diagnostic for graft rejection. In general, and as might be predicted, researchers have found that artificial overexpression of cytoprotective genes promotes graft survival. However, data disclosed herein demonstrate that in actual clinical situations, and in the absence of molecular manipulations of gene expression, high levels of cytoprotective gene transcripts are actually associated with an increased risk of rejection. While not wishing to be bound to a particular mechanism, we believe that the pro-apoptotic onslaught from the immune system causes the graft cells experiencing rejection to express cytoprotective factors that inhibit apoptosis, such as A20 and heme oxygenase 1 (HO1). In a sense, the expression levels of cytoprotective genes may be a measure of the intensity of the pro-apoptotic onslaught, and therefore it is anticipated that high expression levels of cytoprotective genes in general are associated with graft rejection.

The up-regulation of A20 and HO-1 genes during graft rejection may represent the tissue response to immune-mediated injury. Due to its anti-inflammatory and anti-apoptotic roles, these genes might play a role, at least in part, to limit the extent of tissue injury from allograft rejection. It also of interest to note that expression of A20 and HO-1 can be detected in the interstitial infiltrating cells. This suggests that these genes may actually promote the survival of pro-inflammatory cells as well. Because A20 and HO-1 are expressed in both the graft tissue and the infiltrating cells, it is expected that expression of these genes can be measured in biopsies as well as fluid samples.

In another embodiment, the invention provides an "IL-7/17 gene cluster". In one exemplary embodiment, transplant rejection may be diagnosed by detecting increased expression of two, and preferably three, four or more genes of the IL-7/17 gene cluster. The IL-7/17 cluster comprises genes that are coordinately regulated with IL-17 or IL-7 in transplant rejection samples. These two genes are coordinately regulated in transplant rejection and define a cluster of genes that are highly specific and sensitive indicators for acute graft rejection. IL-7 and IL-17 both play a role in promoting maturation or production of B and T cells. In preferred embodiments, transcripts to be detected are members of the IL-7/17 gene cluster and additionally function to promote the maturation and/or production of B cells and/or T cells.

In yet an additional embodiment, the invention provides an "IL-8 gene cluster". In one exemplary embodiment, transplant rejection may be diagnosed by detecting increased expression of one, two, and preferably three, four or more genes of the IL-8 gene cluster. The IL-8 gene cluster comprises genes that are coordinately regulated with IL-8 in transplant rejection samples. IL-8 shows increased expression in graft rejection and defines a cluster of genes that are highly sensitive indicators for graft rejection, preferably acute graft rejection. IL-8 stimulates and facilitates the extravasation of immune cells, promoting infiltration of immune cells into the affected organ. In preferred embodiments, gene expression products to be detected are members of the IL-8 gene cluster and function to promote the extravasation of immune cells and increase penetration of immune cells into the graft tissue.

In a further embodiment, the invention provides an "IL-10 gene cluster". In one exemplary embodiment, transplant rejection may be diagnosed by detecting increased expression of one, two, and preferably three, four or more genes of the IL-10 gene cluster. The IL-10 gene cluster comprises genes that are coordinately regulated with IL-10 in transplant rejection samples. IL-10 shows increased expression in graft rejection and defines a cluster of genes that are indicators for acute graft rejection. IL-10 may have many functions within the immune system. Certain data indicate that IL-10 functions to decrease the production of activating cytokines and ultimately decrease the immune activity of CTLs and natural killer cells. In preferred embodiments, gene expression products to be detected are members of the IL-10 gene cluster and have biological activities that are substantially similar to those of IL-10.

In a different embodiment, the invention provides an "IL-15 gene cluster". In one exemplary embodiment, transplant rejection may be diagnosed by detecting increased expression of one, two, and preferably three, four or more genes of the IL-15 gene cluster. The IL-15 gene cluster comprises genes that are coordinately regulated with IL-15 in transplant rejection samples. IL-15 promotes the killing activity of immune cells such as CTLs and natural killer cells. IL-15 expression is significantly increased in acute graft rejection. In preferred embodiments, transcripts to be detected are members of the IL-15 gene cluster and have biological activities that are substantially similar to those of IL-10.

In yet another embodiment, the invention provides a "T cell gene cluster". In one exemplary embodiment, transplant rejection may be diagnosed by detecting increased expression of one, two, and preferably three, four or more genes of the T cell cluster. The T cell cluster comprises genes that are coordinately regulated with RANTES or CTLA-4 in transplant rejection samples. RANTES and CTLA-4 expression is significantly increased in graft rejection, and particularly acute graft rejection. In preferred embodiments, transcripts to be detected are members of the T cell cluster and have biological activities that are substantially similar to those of RANTES or CTLA-4.

In certain embodiments of the inventive methods, members of multiple gene clusters may be detected. Detection of members of certain gene clusters may increase the sensitivity and/or specificity of the methods. For example, it is notable that increased expression of a member of the IL-8 cluster (including, for example, IL-8) is 100% sensitive for rejection, but only 67% specific. Increased expression of members of the IL-7/17 cluster (eg. IL-7) is highly specific. In one exemplary embodiment, expression of at least one gene from the IL-8 cluster and one from the IL-7/17 cluster may be detected to identify graft rejection conditions. In preferred embodiments, at least two genes of each cluster are detected. It is contemplated that mixtures of genes representing any two, three or more clusters may be detected. Furthermore, the genes to be detected may be selected to represent a variety of different biological processes, thereby providing a profile of the different rejection-related processes occurring in a patient.

It is anticipated that the analysis of more than one gene cluster will be useful not only for diagnosing transplant rejection but also for determining appropriate medical interventions. For example, acute rejection is a general description for a disorder that has many variations and many different optimal treatment strategies. In one embodiment, the invention provides a method for simultaneously identifying graft rejection and determining an appropriate treatment. In general, the invention provides methods comprising measuring representatives of different, informative gene clusters, that indicate an appropriate treatment protocol.

Detecting Gene Expression

In certain aspects the magnitude of expression is determined for one or more genes in sample obtained from a subject. The sample can be essentially any sample of graft material, eg. a tissue biopsy sample, or a fluid sample such as a blood sample, preferably containing peripheral blood mononuclear cells (PBMCs), a urine sample, preferably containing urinary cells, a sample of bronchoalveolar lavage fluid, a sample of bile, pleural fluid or peritoneal fluid, or any other fluid secreted or excreted by a normally or abnormally functioning allograft, or any other fluid resulting from exudation or transudation through an allograft or in anatomic proximity to an allograft, or any fluid in fluid communication with the allograft.

In view of this specification, many different methods are known in the art for measuring gene expression. Classical methods include quantitative RT-PCR, Northern blots and ribonuclease protection assays. Certain examples described herein use competitive reverse transcription (RT)-PCR to measure the magnitude of expression of marker genes. Such methods may be used to examine expression of individual genes as well as entire gene clusters. However, as the number of genes to be examined increases, the time and expense may become cumbersome.

Large scale detection methods allow faster, less expensive analysis of the expression levels of many genes simultaneously. Such methods typically involve an ordered array of probes affixed to a solid substrate. Each probe is capable of hybridizing to a different set of nucleic acids. In one method, probes are generated by amplifying or synthesizing a substantial portion of the coding regions of various genes of interest. These genes are then spotted onto a solid support. mRNA samples are obtained, converted to cDNA, amplified and labeled (usually with a fluorescence label). The labeled cDNAs are then applied to the array, and cDNAs hybridize to their respective probes in a manner that is linearly related to their concentration. Detection of the label allows measurement of the amount of each cDNA adhered to the array.

Many methods for performing such DNA array experiments are well known in the art. Exemplary methods are described below but are not intended to be limiting.

Arrays are often divided into microarrays and macroarrays, where microarrays have a much higher density of individual probe species per area. Microarrays may have as many as 1000 or more different probes in a 1 $cm^2$ area. There is no concrete cut-off to demarcate the difference between micro- and macroarrays, and both types of arrays are contemplated for use with the invention. However, because of their small size, microarrays provide great advantages in speed, automation and cost-effectiveness.

Microarrays are known in the art and consist of a surface to which probes that correspond in sequence to gene products (e.g., cDNAs, mRNAs, oligonucleotides) are bound at known positions. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least 100 genes and more preferably, 500, 1000, 4000 or more. In certain embodiments, the most preferred arrays will have about 98–100% of the genes of a particular organism represented. In other embodiments, the invention provides customized microarrays that have binding sites corresponding to fewer, specifically selected genes. Microarrays with fewer binding sites are cheaper, smaller and easier to produce. In particular, the invention provides microarrays customized for the determination of graft status. In preferred embodiments customized microarrays comprise binding sites for fewer than 4000, fewer than 1000, fewer than 200 or fewer than 50 genes, and comprise binding sites for at least 2, preferably at least 3, 4, 5 or more genes of any of the clusters of Table 1. Preferably, the microarray has binding sites for genes relevant to testing and confirming a biological network model of interest. Several exemplary human microarrays are publicly available. The Affymetrix GeneChip HUM 6.8K is an oligonucleotide array composed of 7,070 genes. A microarray with 8,150 human cDNAs was developed and published by Research Genetics (Bittner et al., 2000, Nature 406:443–546).

The probes to be affixed to the arrays are typically polynucleotides. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or CDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Random oligo-dT priming may also be used to obtain cDNAs corresponding to as yet unknown genes, known as ESTs. Certain arrays use many small oligonucleotides corresponding to overlapping portions of genes. Such oligonucleotides may be chemically synthesized by a variety of well known methods. Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, Nature 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, Genomics 29:207–209). In yet another embodiment, the polynucleotide of the binding sites is RNA.

The nucleic acids or analogues are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Science 270:467–470. This method is especially useful for preparing microarrays of cDNA. (See also DeRisi et al., 1996, Nature Genetics 14:457–460; Shalon et al., 1996, Genome Res. 6:639–645; and Schena et al., 1995, Proc. Natl. Acad. Sci. USA 93:10539–11286). Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Science 251:767–773; Pease et al., 1994, Proc. Natl. Acad. Sci. USA 91:5022–5026; Lockhart et al., 1996, Nature Biotech 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, 11: 687–90). When these methods are used, oligonucleotides of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, Nuc. Acids Res. 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

The nucleic acids to be contacted with the microarray may be prepared in a variety of ways. Methods for preparing total and poly(A)+ RNA are well known and are described generally in Sambrook et al., supra. Labeled cDNA is prepared from mRNA by oligo dT-primed or random-primed reverse transcription, both of which are well known in the art (see e.g., Klug and Berger, 1987, Methods Enzymol. 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Nature Biotech. 14:1675). The cDNAs or RNAs can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescent labels are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Academic Press San Diego, Calif.).

In another embodiment, a label other than a fluorescent label is used. For example, a radioactive label, or a pair of radioactive labels with distinct emission spectra, can be used (see Zhao et al., 1995, Gene 156:207; Pietu et al., 1996, Genome Res. 6:492). However, use of radioisotopes is a less-preferred embodiment.

Nucleic acid hybridization and wash conditions are chosen so that the population of labeled nucleic acids will specifically hybridize to appropriate, complementary nucleic acids affixed to the matrix. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches).

Optimal hybridization conditions will depend on the length (e.g., oligomer versus polynucleotide greater than 200 bases) and type (e.g., RNA, DNA, PNA) of labeled nucleic acids and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array can be, preferably, detected by scanning confocal laser microscopy. When two fluorophores are used, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, Genome Research 6:639–645). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6:639–645 and in other references cited herein. Alternatively, the fiber-optic bundle described by Ferguson et al., 1996, Nature Biotech. 14:1681–1684, may be used to monitor mRNA abundance levels at a large number of sites simultaneously. Fluorescent microarray scanners are commercially available from Affymetrix, Packard BioChip Technologies, BioRobotics and many other suppliers.

Signals are recorded, quantitated and analyzed using a variety of computer software. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores is preferably calculated. The ratio is independent of the absolute expression level of the cognate gene, but is useful for genes whose expression is significantly modulated by drug administration, gene deletion, or any other tested event.

According to the method of the invention, the relative abundance of an mRNA in two samples is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In one embodiment, transcript arrays reflecting the transcriptional state of a cell of interest are made by hybridizing a mixture of two differently labeled sets of cDNAs to the microarray. One cell is a cell of interest while the other is used as a standardizing control. The relative hybridization of each cell's cDNA to the microarray then reflects the relative expression of each gene in the two cells. For example, to assess gene expression in a variety of breast cancers, Perou et al. (2000, supra) hybridized fluorescently-labeled cDNA from each tumor to a microarray in conjunction with a standard mix of cDNAs obtained from a set of breast cancer cell lines. In this way, gene expression in each tumor sample was compared against the same standard, permitting easy comparisons between tumor samples.

In preferred embodiments, expression levels in different samples and conditions may be compared using a variety of statistical methods. A variety of statistical methods are available to assess the degree of relatedness in expression patterns of different genes. The statistical methods may be broken into two related portions: metrics for determining the relatedness of the expression pattern of one or more gene, and clustering methods, for organizing and classifying expression data based on a suitable metric (Sherlock, 2000, Curr. Opin. Immunol. 12:201–205; Butte et al., 2000, Pacific Symposium on Biocomputing, Hawaii, World Scientific, p.418–29).

In one embodiment, Pearson correlation may be used as a metric. In brief, for a given gene, each data point of gene expression level defines a vector describing the deviation of the gene expression from the overall mean of gene expression level for that gene across all conditions. Each gene's expression pattern can then be viewed as a series of positive and negative vectors. A Pearson correlation coefficient can then be calculated by comparing the vectors of each gene to each other. An example of such a method is described in Eisen et al. (1998, supra). Pearson correlation coefficients account for the direction of the vectors, but not the magnitudes.

In another embodiment, Euclidean distance measurements may be used as a metric. In these methods, vectors are calculated for each gene in each condition and compared on the basis of the absolute distance in multidimensional space between the points described by the vectors forthegene.

In a further embodiment, the relatedness of gene expression patterns may be determined by entropic calculations (Butte et al. 2000, supra). Entropy is calculated for each gene's expression pattern. The calculated entropy for two genes is then compared to determine the mutual information. Mutual information is calculated by subtracting the entropy of the joint gene expression patterns from the entropy for calculated for each gene individually. The more different two gene expression patterns are, the higher the joint entropy will be and the lower the calculated mutual information. Therefore, high mutual information indicates a non-random relatedness between the two expression patterns.

The different metrics for relatedness may be used in various ways to identify clusters of genes. In one embodiment, comprehensive pairwise comparisons of entropic measurements will identify clusters of genes with particularly high mutual information. In preferred embodiments, expression patterns for two genes are correlated if the normalized mutual information score is greater than or equal to 0.7, and preferably greater than 0.8, greater than 0.9 or greater than 0.95. In alternative embodiments, a statistical significance for mutual information may be obtained by randomly permuting the expression measurements 30 times and determining the highest mutual information measurement obtained from such random associations. All clusters with a mutual information higher than can be obtained randomly after 30 permutations are statistically significant. In a further embodiment, expression patterns for two genes are correlated if the correlation coefficient is greater than or equal to 0.8, and preferably greater than 0.85, 0.9 or, most preferably greater than 0.95.

In another embodiment, agglomerative clustering methods may be used to identify gene clusters. In one embodiment, Pearson correlation coefficients or Euclidean metrics are determined for each gene and then used as a basis for forming a dendrogram. In one example, genes were scanned for pairs of genes with the closest correlation coefficient. These genes are then placed on two branches of a dendrogram connected by a node, with the distance between the depth of the branches proportional to the degree of correlation. This process continues, progressively adding branches to the tree. Ultimately a tree is formed in which genes connected by short branches represent clusters, while genes connected by longer branches represent genes that are not clustered together. The points in multidimensional space by Euclidean metrics may also be used to generate dendrograms.

In yet another embodiment, divisive clustering methods may be used. For example, vectors are assigned to each gene's expression pattern, and two random vectors are generated. Each gene is then assigned to one of the two random vectors on the basis of probability of matching that vector. The random vectors are iteratively recalculated to generate two centroids that split the genes into two groups. This split forms the major branch at the bottom of a dendrogram. Each group is then further split in the same manner, ultimately yielding a fully branched dendrogram.

In a further embodiment, self-organizing maps (SOM) may be used to generate clusters. In general, the gene expression patterns are plotted in n-dimensional space, using a metric such as the Euclidean metrics described above. A grid of centroids is then placed onto the n-dimensional space and the centroids are allowed to migrate towards clusters of points, representing clusters of gene expression. Finally the centroids represent a gene expression pattern that is a sort of average of a gene cluster. In certain embodiments, SOM may be used to generate centroids, and the genes clustered at each centroid may be further represented by a dendrogram. An exemplary method is described in Tamayo et al., 1999, PNAS 96:2907–12. Once centroids are formed, correlation must be evaluated by one of the methods described supra.

In another aspect, the invention provides probe sets. Preferred probe sets are designed to detect expression of one or more genes and provide information about the status of a graft. Preferred probe sets of the invention comprise probes that are useful for the detection of at least two genes belonging to any of the gene clusters of Table 1. Particularly preferred probe sets will comprise probes useful for the detection of at least one, two, three, four or at least five genes belonging to any of the gene clusters of Table 1. Probe sets of the invention comprise probes useful for the detection of no more than 10,000 gene transcripts, and preferred probe sets will comprise probes useful for the detection of fewer than 4000, fewer than 1000, fewer than 200, and most preferably fewer than 50 gene transcripts. Probe sets of the invention are particularly useful because they are smaller and cheaper than probe sets that are intended to detect as many genes as possible in a particular genome. The probe sets of the invention are targeted at the detection of gene transcripts that are informative about transplant status. Probe sets of the invention may also comprise a large or small number of probes that detect gene transcripts that are not informative about transplant status. Such probes are useful as controls and for normalization. Probe sets may be a dry mixture or a mixture in solution. In preferred embodiments, probe sets of the invention are affixed to a solid substrate to form an array of probes. It is anticipated that probe sets may also be useful for multiplex PCR. The probes of probe sets may be nucleic acids (eg. DNA, RNA, chemically modified forms of DNA and RNA), or PNA, or any other polymeric compound capable of specifically interacting with the desired nucleic acid sequences.

Proteins

It is further anticipated that increased levels of certain proteins may also provide diagnostic information about transplants. In certain embodiments, one or more proteins encoded by genes of any of the gene clusters of Table 1 may be detected, and elevated or decreased protein levels may be used to diagnose graft rejection. In a preferred embodiment, protein levels are detected in a post-transplant fluid sample, and in a particularly preferred embodiment, the fluid sample is peripheral blood or urine. In another preferred embodiment, protein levels are detected in a graft biopsy.

In view of this specification, methods for detecting proteins are well known in the art. Examples of such methods include Western blotting, enzyme-linked immunosorbent assays (ELISAs), one- and two-dimensional electrophoresis, mass spectroscopy and detection of enzymatic activity. Suitable antibodies may include polyclonal, monoclonal, fragments (such as Fab fragments), single chain antibodies and other forms of specific binding molecules.

Kits

In certain aspects, kits are provided. Commercially available kits for use in these methods are, in view of this specification, known to those of skill in the art. In general, kits will comprise a detection reagent that is suitable for detecting the presence of a polypeptide or nucleic acid of interest. For example, in one embodiment described herein, PBMCs are isolated from whole blood and RNA is extracted using a commercially available QIAGEN™ technique. In another exemplary embodiment, RNA is obtained from urine samples, and in yet another exemplary embodiment, RNA is obtained from a graft biopsy. It is contemplated that kits may be designed for isolating and/or detecting mRNA in essentially any sample, and a wide variety of reagents and methods are, in view of this specification, known in the art.

For example, QIAGEN manufactures a number of commercially available kits for RNA isolation, including RNEASY® Total RNA System (involving binding total RNA to a silica-gel-based membrane and spinning the RNA); OLIGOTEX™ mRNA kits (utilizing spherical latex particles); and QIAGEN total RNA kit for In Vitro Transcripts and RNA clean-up. The basic QIAGEN technique involves four steps, as set forth in Example 2, below. The QIAGEN technique can be modified to enhance the RNA isolation, by methods well-known to those of skill in the art.

The complementary DNA was coamplified with a gene-specific competitor and the quantification comprised generating a standard curve of serial dilutions of the gene-specific competitor with a constant amount of control reverse transcribed complementary DNA, thereby enabling quantification of the transcript of the gene of interest. As described herein, the gene-specific competitor is generated from phytohemagglutinin-simulated blast cells or nephrectomy tissue.

For example, the cDNA of perforin can be amplified with a pair of oligonucleotide primers comprising the nucleotides of SEQ. ID. NOS.:17 and 18 of Table 1. Likewise, the transcript of glyceraldehyde-3-phosphate dehydrogenase can be amplified with oligonucleotide primers comprising the nucleotide sequence of SEQ. ID. NOS. 1 and 2. A20, for example, can be amplified and quantified using primers selected from SEQ ID NOS: 33, 34 and 35. HO-1, for example, can be amplified with primers selected from SEQ ID NOS: 39, 40 and 41. Although these primers are specifically described herein, other suitable primers can be designed using techniques well-known to those of skill in the art. See, for example, Current Protocols in Molecular Biology, Volume 2, Ausubel et al., eds., John Wiley & Sons, Inc. (1997) at pp. 15.0.1-1-15.8.8.

In other embodiments, kits of the invention may comprise probe sets and probe sets may be affixed to a solid surface to form a customized array. In certain embodiments, kits of the invention may comprise any of the following components: materials for obtaining a sample, enzymes, buffers and primers for amplifying certain genes, materials for labeling nucleic acids, microarrays, a microarray reader, competitor nucleic acids, control nucleic acids, antibodies for detecting proteins among many other possible components.

In further embodiments, kits of the invention may comprise a urine collection system. Urine collection systems may comprise essentially any material useful for obtaining and/or holding a urine sample. Urine collection systems may include, for example, tubing, a beaker, a flask, a test tube or a container with a lid (eg. a plastic container with a snap-on or screw top lid). In certain embodiments, kits of the invention may also comprise a urine presentation system. A urine presentation system may comprise essentially any material that is useful for presenting the urine to be contacted with the appropriate detection or purification reagents. A urine presentation system may comprise, for example, a sample well, which may be part of a multi-well plate, a petri dish, a filter (eg. paper, nylon, nitrocellulose, PVDF, cellulose, phosphocellulose, or other fibrous surface), a microchannel (which may be part of a microchannel array or a microfluidics device), a small tube such as a thin-walled PCR tube or a 1.5 ml plastic tube, a microarray to which urine or material obtained from urine may be applied, a capillary tube or a flat or curved surface with detection reagent adhered thereto, or a flat or curved surface with material that adheres to proteins or nucleic acids present in the urine sample. Kits of the invention may also comprise a sample preparation system. A sample preparation system comprises, generally, any materials or substances that are useful in preparing the urine sample to be contacted with the detection reagents. For example, a sample preparation system may comprise materials for separating urine sediments from the fluids, such as centrifuge tube, a microcentrifuge, a filter (optionally fitted to a tube designed to permit a pressure gradient to be established across the filter), buffers, precipitating agents for precipitating either wanted or unwanted materials, chelators, cell lysis reagents etc. It is anticipated that collection, presentation and preparation systems may be combined in various ways. For example, a filter may be used to separate urine sediments from the fluids, and the filter may be coated with antibodies suitable for specifically detecting the desired proteins. One of skill in the art would, in view of this specification, readily understand many combinations of components that a kit of the invention may comprise.

Detection of Infectious Agents

In certain aspects, the information obtained by detecting the magnitude of expression of human genes can be complimented by detecting the expression of genes from possible infectious agents.

In one embodiment, the infectious agent analyzed is cytomegalovirus (CMV). CMV is a common and dangerous infection in transplant recipients. It generally appears on or after the end of the first post-transplant month. 50% of all renal transplant recipients presenting with fever 1 to 4 months after transplantation have evidence of CMV disease. *Harrison's Principles of Internal Medicine,* 14th. ed. Fauci, A. S. et al., McGraw-Hill (1988). CMV itself accounts for the fever in more than ⅔ of cases and thus is the predominant pathogen during this period. CMV infection may also present as arthralgias or myalgias. This infection can result in primary disease (in the case of a seronegative recipient who receives a kidney from a seropositive donor) or can present as either reactivation disease or superinfection during this interval. CMV also causes glomerulopathy and is associated with an increased incidence of other opportunistic infections (e.g., fungal infection). Because of the frequency and severity of CMV disease, considerable effort has been made to attempt to prevent and treat it in renal transplant recipients. CMV retinitis can also appear as a late infection (more than 6 months after transplantation). Furthermore, active CMV infection is sometimes associated, and confused, with transplant rejection episodes.

As described in Example 2, false positive PBMC results indicating acute transplant rejection were obtained from two patients with CMV infection. Therefore, additionally detecting the presence or absence of one or more genes characteristic of CMV can effectively discriminate between acute rejection and CMV infection. For example, in addition to quantifying cDNA encoding perforin, granzyrne B and Fas ligand, determining the presence or absence of cDNA encoding a gene characteristic of CMV (or other infectious agent) can be simultaneously, or subsequently determined by RT-PCR. The genetic properties of cytomegalovirus have been characterized in great detail, and are well known to those of skill in the art. (See, for example, *Virology,* $2^{nd}$ Ed., Fields, B. N. E., Raven Press, Ltd., N.Y. (1990)), at pages 1595–2010. Primer sequences for CMV are known and available to those of skill in the art. See Meyer König, U. et al. *J. Infectious Diseases, Vol.* 171:705–709 (1995) the contents of which are incorporated by reference in their entirety; Wright, P. A. and D. Wynford-Thomas, *J. Pathol., Vol.* 162:99 (1990); Cassol, S. A. et al, *J. Clin. Invest., Vol.* 83:1109–1115 (1989). For example, primer sequences TCC ACG CTG TTT TGA CCT CCA TAG (CMV-sense) (SEQ ID NO:31) and GAC ATC TTT CTC GGG GTT CTC GTT (CMV anti-sense) (SEQ ID NO:32) can be used. Competitive templates can be devised to accurately quantify CMV and other infectious agents transcripts using the methods described herein for the immune activation marker genes. See Clinical Laboratory Medicine, McClatchey, K. D., ed., William & Wilkins, Baltimore, Md. (1994) at 165–174.

Other transplants, including lung, heart, liver and bone marrow, can be tested in a similar matter. For example, embodiment, detection of hepatitis virus transcripts can effectively discriminate between liver transplant rejection and hepatitis infection. One of skill in the art can design primers for detection of hepatitis virus use in this embodiment. See *Virology,* supra, at pages 1981–2236.

The present invention will now be illustrated by the following examples, which are not intended to be limiting in any way.

EXAMPLE 1

Analysis of Biopsy Samples

Biopsies:

Sixty kidney transplant biopsies were investigated for gene expression of chemokines (IL-8, RANTES (regulated upon activation, normal T-cell expressed and secreted), T-cell growth factors and other cytokines (IL-2, IL-4, IL-7, IL-10, IL-15, and IL-17), cell surface immunoregulatory proteins (CTLA4), cytotoxic effector molecules (P, GB, FasL), IFN-γ, transforming growth factor (TGF)-1, and the housekeeping protein glyceraldehyde-3-phosphate dehydrogenase (GAPDH). Thirty-eight biopsies were obtained from 34 patients (25 adults and 9 children) to clarify the cause of graft dysfunction, 20 for early post-transplant surveillance and 2 from living related donor kidneys prior to reperfusion. Small portions of biopsy cores (1/10–1/2) were immediately snap frozen in liquid nitrogen at the bedside and stored at 70° C. The majority of tissue was used for histopathological analysis. Biopsies obtained to evaluate the cause of graft dysfunction were classified according to the Banff criteria (Solez et al., Kidney Int. 44: 411–422 (1993)) as rejection (pretreatment n=12, post-treatment n=3), nonrejection (acute tubular necrosis, cyclosporine nephrotoxicity n=12), chronic rejection (n=3), recurrence of primary disease (n=4), or other complications (n=4). In 4 of 12 rejecting samples and 4 of 12 acute tubular necrosis samples a mild cellular infiltrate was observed (borderline cases) and the diagnosis of rejection was confirmed by a beneficial clinical response to corticosteroids or OKT3 treatment.

RNA Isolation:

Procedures for isolation of tissue RNA and reverse transcription into cDNA were performed as described in detail (Lipman et al., J. Immunol. 152: 5120–5127 (1994)). In brief, total RNA was isolated by tissue homogenization in guanidine isothiocyanate/2-mercaptoethanol and ultracentrifuigation in CsCl. One microgram of RNA was reverse transcribed by Moloney murine leukemia virus transcriptase and diluted to a final volume of 40 μl.

Quantification of Gene Expression by Competitive Template RT-PCR

Expression of specific gene transcripts identified within biopsy tissue was quantified by competitive RT-PCR as described in Lipman, M., et al., J. Immunol., 152:5120–5127 (1994), the contents of which is incorporated herein in its entirety by reference. Competitive RT-PCT is also described in Bunn et al. (U.S. Pat. No. 5,213,961, incorporated herein by reference in its entirety). The cDNA derived from biopsy samples was coamplified with a known amount of a mutated target gene CDNA fragment—the gene-specific competitor. Sense and antisense oligonucleotides proportionately amplified both competitor and reverse-transcribed cDNA sequences in accordance with their relative initial abundance in the PCR. (Sequences are listed in FIG. 1 and Table 2 as SEQ ID NOS: 1–30).

TABLE 2

Sequences of oligonucleotide primers and competitive templates (CTs) used for the quantitation of 15 genes evaluated.

| GENE | DIRECTION | SEQUENCE 5' TO 3' | SEQ. ID. NO. | GENE ACC |
|---|---|---|---|---|
| GAPDH | sense | GGTGAAGGTCGGAGTCAACG | SEQ. ID. NO:1 | J04038 |
|  | antisense | CAAAGTTGTCATGGATGACC | SEQ. ID. NO:2 |  |
| IL-2 | sense | CCTCTGGAGGAAGTGCTAAA | SEQ. ID. NO:3 | K02056 |
|  | antisense | ATGGTTGCTGTCTCATCAGC | SEQ. ID. NO:4 |  |
| IL-4 | sense | TTCTACAGCCACCATGAGAAG | SEQ. ID. NO:5 | M23442 |
|  | antisense | CAGCTCGAACACTTTGAATAT | SEQ. ID. NO:6 |  |
| IL-7 | sense | TTTAGGTATATCTTTGGACTTCCTC | SEQ. ID. NO:7 | J04156 |
|  | antisense | GTGTTCTTTAGTGCCCATCAA | SEQ. ID. NO:8 |  |
| IL-8 | sense | TCTCTTGGCAGCCTTCCT | SEQ. ID. NO:9 | M68932 |
|  | antisense | AATTCTCAGCCTCTTCAAAAACTT | SEQ. ID. NO:10 |  |
| IL-10 | sense | GCCGTGGAGCAGGTGAAG | SEQ. ID. NO:11 | X78437 |
|  | antisense | AAGCCCAGAGACAAGATA | SEQ. ID. NO:12 |  |
| IL-15 | sense | CCGTGGCTTTGAGTAATGAG | SEQ. ID. NO:13 | X91233 |
|  | antisense | CAGATTCTGTTACATTCCC | SEQ. ID. NO:14 |  |
| IL-17 | sense | GGAGGCCATAGTGAAGG | SEQ. ID. NO:15 | U32659 |
|  | antisense | GGGTCGGCTCTCCATAG | SEQ. ID. NO:16 |  |
| perforin | sense | CGGCTCACACTCACAGG | SEQ. ID. NO:17 | M31951 |
|  | antisense | CTGCCGTGGATGCCTATG | SEQ. ID. NO:18 |  |
| granzyme B | sense | GGGGAAGCTCCATAAATGTCACCT | SEQ. ID. NO:19 | M28879 |
|  | antisense | TACACACAAGAGGGCCTCCAGAGT | SEQ. ID. NO:20 |  |
| Fas-L | sense | GCCTGTGTCTCCTTGTGA | SEQ. ID. NO:21 | U11821 |
|  | antisense | GCCACCCTTCTTATACTT | SEQ. ID. NO:22 |  |
| TGF-β1 | sense | CTGCGGATCTCTGTGTCATT | SEQ. ID. NO:23 | X14885-91 |
|  | antisense | CTCAGAGTGTTGCTATGGTG | SEQ. ID. NO:24 |  |
| IFN-γ | sense | CCAGAGCATCCAAAAGAGTGTG | SEQ. ID. NO:25 | A02137 |
|  | antisense | CTAGTTGGCCCCTGAGATAAAG | SEQ. ID. NO:26 |  |
| CTLA4 | sense | GCAATGCACGTGGCCCAGCC | SEQ. ID. NO:27 | M28879 |
|  | antisense | TTTCACATTCTGGCTCTGTTGG | SEQ. ID. NO:28 |  |
| RANTES | sense | CGGCACGCCTCGCTGTCATC | SEQ. ID. NO:29 | M21121 |
|  | antisense | TGTACTCCCGAACCCATTT | SEQ. ID. NO:30 |  |

The PCR products were separated by agarose gel electrophoresis, stained with ethidium bromide, photographed in UV light with Polaroid type 55 positive/negative film, and scanned by laser densitometry (LKB Ultrascan). The ratio of densities (competitive template (CT)/reverse-transcribed cDNA) reflects the initial amounts of cDNA added (pg of competitive template per pg of reverse-transcribed cDNA). Standard curves were generated by serial dilutions of the gene-specific competitors with a constant amount of control reverse transcribed cDNA, thereby enabling quantification of the wild-type gene transcript.

Contaminating genomic DNA was easily identified by size differences, as all oligonucleotide probes were targeted to separate exons of the gene of interest. The conditions used for all competitive PCRs were identical: 94° C. for 30 sec, 55° C. for 20 sec, 72° C. for 20 sec, 10-min extension at 72° C. after 35 cycles (Perkin-Elmer Cetus 480). Competitors from phytohemagglutinin-stimulated blasts or nephrectomy tissue were generated by four different techniques (FIG. 1): (i)excision of a 50- to 100-bp fragment in the center of the target gene cDNA by using appropriate restriction enzymes (GAPDH, IFN-γ, IL-10, IL-15, IL-17, P, and GB); (ii) amplification of external parts of the cDNA by two separate PCRs and religation of these fragments (CTLA4, IL-7, FasL); (iii) insertion of a short DNA fragment into the target sequence (IL-2, IL-4, TGF-1, or primer deletion (IL-4)); and (iv) one-step generation of a shortened DNA sequence by use of a specifically designed double-sense primer. Competitors were cloned in a TA vector (Invitrogen, San Diego), transfected into DH5a cells (Promega), purified, and quantitated by UV spectrometry.

Amplification of the universally expressed GAPDH gene served to confirm successful RNA isolation and reverse transcription. The magnitude of target gene expression was calculated as pg of target gene cDNA per pg of GAPDH cDNA.

Statistical analysis was performed using a Newman-Keuls test for normally distributed data or a Kruskal-Wallis test.

Results

The small amount of tissue available for this study (1/10 to ½ of a biopsy core) proved to be sufficient for a thorough analysis of gene expression. The RNA yield ranged from 1 to 20 μg, depending on the size of the biopsy fragment, allowing 40–800 PCRs per sample. A quantitative analysis of gene expression was necessary, because low levels of transcripts are detectable in many biopsies, while heightened expression of select genes occurred only during rejection (FIGS. 2A–F, Table 3).

TABLE 3

Quantitative analysis of intragraft gene expression for 15 immune activation genes.

| Gene | Rejection | Nonrejection | P* | Sensitivity % | Specificity % |
|---|---|---|---|---|---|
| IL-2 | 0.0 | 0.0 | NS | 8 | NA |
| IL-4 | 0.0 | 0.0 | NS | 0 | 0 |
| TGF-β1 | 112 ± 87 | 98 ± 78 | NS | 45 | 55 |
| CTLA-4 | 577 ± 396 | 228 ± 214 | <0.057 | 60 | 70 |
| RANTES | 284 ± 147 | 132 ± 104 | <0.064 | 91 | 71 |
| IFN-γ | 214 ± 194 | 151 ± 130 | 0.007 | 75 | 67 |
| IL-17 | 24 ± 12 | 0.0 | <0.001 | 83 | 75 |
| IL-7 | 38 ± 40 | 0.0 | <0.001 | 83 | 100 |
| IL-8 | 112 ± 82 | 67 ± | <0.0005 | 100 | 67 |
| IL-10 | 451 ± 340 | 24 ± 30 | <0.0005 | 83 | 89 |
| IL-15 | 236 ± 162 | 85 ± 37 | <0.0005 | 83 | 92 |

TABLE 3-continued

Quantitative analysis of intragraft gene expression for 15 immune activation genes.

| Gene | Rejection | Nonrejection | P* | Sensitivity % | Specificity % |
|---|---|---|---|---|---|
| GB | 174 ± 94 | 46 ± 51 | <0.0015 | 91 | 86 |
| P | 1705 ± 1021 | 338 ± 410 | <0.0001 | 83 | 92 |
| FasL | 779 ± 360 | 120 ± 101 | <0.0001 | 83 | 92 |

Values are given as mean ± SD pg of target gene cDNA per pg of GAPDH cDNA. The intensity of intragraft expression of individual CTL genes was compared with histologic (Banff) criteria for establishing the diagnosis of graft rejection through an analysis of 40 transplant biopsies and, in borderline cases, clinical response to antirejection treatment. NA, not applicable.
*Statistical analysis was performed with a Newman-Keuls test for normally distributed data and a Kruskal-Wallis test for others. NS, not significant.

Heightened gene expression during acute rejection was detected for IL-7, IL-8, RANTES, IL-10, IL-15, IL-17, CTLA4, and all three CTL effector molecules, e.g., GB, P, and FasL (FIGS. 2A–F). GB and IL-10 expression (P<0.0015 and P<0.0005) proved to be significant and specific markers of acute, but not chronic, rejection, while IL-15 (P<0.0015), FasL, and P (P<0.0001 and P<0.0001) transcription was augmented during acute allograft rejection and in some of the chronic rejection samples analyzed. The magnitude of expression of individual CTL-specific genes was not linked, and no evidence was found that the granula-dependent (GB, P) or the receptor-mediated (FasL) pathways were alternatively activated. IL-7 and IL-17 transcripts were solely, but not reliably, observed in rejecting samples, while an increase of IL-8 and RANTES mRNA was found in both rejection and graft dysfunction related to other causes. The highest level of any target gene expression measured was 4.4 times higher than the amount of GAPDH gene expression in this sample (FasL in an acute rejection episode). IL-2 and IL-4 gene expression did not accompany rejection episodes.

The accuracy of this PCR-based molecular approach to verify rejection can be considerably enhanced by a simultaneous analysis of CTL gene expression (Table 3). If a discriminatory level for heightened gene expression is set to the mean±95% confidence interval of values observed in nonrejecting kidneys (maximum 0.07 pg/pg of GAPDH for B, 0.4 pg/pg of GAPDH for FasL, and 0.8 pg/pg of GAPDH for P), the combined analysis of all three CTL effector molecules identifies acute cellular rejection, including borderline cases with a sensitivity of 100% and a specificity of 100% in our series (P<0.0001).

TABLE 4

Combined analysis of CTL gene expression

| Gene | Rejection | Non-rejection | P* | Sensitivity % | Specificity % |
|---|---|---|---|---|---|
| P + GB, one or both up-regulated | 11/12 | 5/28 | 0.00015* | 91 | 82 |
| FasL + GB, one or both up-regulated | 12/12 | 4/28 | <0.0001 | 100 | 85 |
| FasL + GB + P, any two up-regulated | 12/12 | 0/28 | <0.0001* | 100 | 100 |

Expression of an individual gene was deemed positive for values above the mean ±95% confidence interval of nonrejecting kidneys (maximum 0.07 pg/pg of GAPDH for GB and 0.4 pg/pg of GAPDH for FasL and 0.8 pg/pg of GADPH for P).
*Statistical analysis was performed with a $X^2$ test.

The magnitude of gene expression indicative for those genes associated with rejection, i.e., GB, P, and FasL, apparently declines after initiation of effective antirejection therapy (OKT3 or steroid pulses) as exemplified in the few sequential biopsy specimens analyzed (FIG. 2).

Post-transplant surveillance biopsies showed similar levels of IL-7, IL-10, IL-17, and GB transcripts as compared with nonrejecting kidneys, while early (day 4 and 11) post-transplant specimens revealed that IL-15, CTLA4, P, and FasL mRNA levels were 2- to 5-fold higher and showed a tendency to decline within the first week. In a limited sampling, early post-transplant gene expression was not predictive for the later development of rejection episodes.

EXAMPLE 2

Analysis of PBMCS

In a study of 16 renal allograft recipients, PBMCs were isolated from whole blood and RNA extracted by a modified QIAGEN™ method. (QIAGEN Rneasy Blood Mini Kits, Cat. No. 74303, 74304 or 74305). The QIAGEN technique involves four steps: 1) a sample is combined with a suitable buffer for isolating RNA in the sample from the remaining components, e.g., 1 part whole blood, is mixed with 5 parts lysing buffer, wherein the blood cells are lysed and RNA released; 2) RNA in the sample is specifically bound to particles or a membrane; 3) the particles or membrane are washed to remove non-RNA components; and 4) the isolated RNA is eluted from the particles/membrane.

To increase the efficiency of RNA isolation from PBMCs, the second step of the QIAGEN protocol was modified as described in Example 3.

Gene expression was analyzed by reverse transcription-assisted semi-quantitative PCR in PMBC and in snap frozen transplant core biopsies and was compared to the histopathological results (AR=12 and non rejecting NR=4). Coordinate gene expression in PBMCs and the AR grafts was noted in $^{11}/_{12}$ (92%) for P, $^{10}/_{12}$ (83%) for GB and $^{9}/_{12}$ (75%) for FasL. Biopsy pathology could be accurately predicted by upregulation of at least 2 of the 3 genes in PBMCs in all cases. In the NR samples, false positive gene expression in PBMCs was noted in $^{2}/_{4}$ (50%) for P, $^{2}/_{4}$ (50%) for GB and $^{1}/_{4}$ (25%) for FasL when compared with intragraft gene expression. The false positive PBMC results were obtained from 2 patients with CMV infection. Biopsy histopathology in the NR specimens was accurately predicted by non-expression of 2 of the 3 genes in PBMCs in the 2 patients without CMV infection. These results indicate that the evaluation of CTL gene expression in PBMCs with evaluation of markers for CMV can be used to assess the need for allograft biopsy and evaluate acute transplant rejection.

EXAMPLE 3

Method for Processing Blood for PCR Analysis

Blood Collection
Supplies:
2 ml EDTA vacuum tubes (purple top): cat #369651 Vacutainer; Flask with ice.
Procedure:
Label EDTA tubes with Patient ID, date and time.
Draw 2 ml blood into EDTA tube and carefully mix by inversion; transport on ice to the lab to be processed.*
* For optimal results, blood samples should be processed within a few hours.
White Blood Cell Isolation
Supplies:
3 cc syringes
15 ml Sterile Conical tubes (Falcon)-Sterile polypropylene tubes (20–200–1000 ul)
RPMI Medium 1640: cat #11875-085 Gibco BRL
EL Buffer: cat #79217 Qiagen
Flask with liquid nitrogen: cat #2123 Lab-Line.
Ethanol (96–100%)-70% ethanol in water
14.5 M-Mercaptoethanol (-ME)
Lab centrifuge with rotor for 15 ml tubes -4C Microcentrifuge with rotor for 2 ml tubes
Instrumentation:
Lab centrifuge with rotor for 15 ml tubes at 4C.
Procedure:
1. Using a 3 cc syringe transfer 1–1.5 ml blood into 15 cc tube.
2. Mix the sample with 7.5 EL Buffer(1 ml/5 ml EL Buffer)
3. Incubate for 10–15 minutes on ice. Mix by vortexing briefly 2 times during incubation.
   If the cloudy suspension does not become translucent, prolong incubation on ice to 20 minutes.
4. Centrifuge at 400× g for 10 minutes at 4C, check for pellet and discard all supernatant.
   If pellet is red, incubate for an additional 5–10 minutes on ice after addition of EL Buffer at step 5.
5. Add 2 ml EL Buffer to the cell pellet. Resuspend cell using a pipet to carefully remove red cells. Add RPMI culture medium enough to fill 10 cc tube, place on ice.
6. Centrifuge again as in step 4, discard supernatant and make sure the pellet is completely clear of blood. If not, repeat step 5.
7. Place the tube with the pellet into the canister with liquid nitrogen to snap freeze.** Store at −70 Celsius.
8. Add 600 ul Buffer RLT (add 2ME) to pelleted while cells. Vortex or pipet to mix. No while cell pellet should be visible after this step.
9. Transfer lysis solution to Qiashedder column and spin 2 min 14–18.000 rpm.
10. Discard column and add equal amount of 70% ethanol to lysis solution and mix by pipetting.
11. Apply 500 ul to RNeasy column and spin 15 seconds with 10.000 rpm, discard flow-through and repeat with any remaining fluid.
12. Discard flow-through and pipet 700 ul Wash Buffer RW1 into spin column, centrifuge for 15 seconds 10.000 rpm and discard flow-through.
13. Place spin column in new 2 ml collection tube, pipet 500 ul of Wash Buffer RPE into column and centrifuge as above. Discard flow-through.
14. Pipet 500 ml of wash Buffer RPE into column and centrifuge for 2 minutes full speed to dry column; discard flow-through.
15. Transfer spin column to 1.7 ml Eppendorf tube and elute RNA with 30 ul of DEPC-treated or pure water. Spin for 1 minute 10.000 rpm. Repeat this step with 30 ul of water for further elution into the same collection tube.
16. Measure RNA by UV spectrometry and store at −70 C. If little or no RNA is eluted, again add 30 ul DEPC water to the spin column at room temperature for 10 min, then repeat step 15.

** This is a crucial step. RNA remains in snap frozen specimen stored at −70 C. However, it will rapidly degrade if the pellet defrosts or if snap freezing or storing is delayed.

EXAMPLE 4

Method for Diagnosing Rejection Using Urine Samples

Methods
Collection of Urine Samples and Renal Biopsy Specimens.
A total of 151 urine specimens (110 in the first month, 24, 1–6 months, and 17, 6 months after transplantation) were collected from 89 renal allograft recipients. Forty-four biopsy specimens were from 39 patients who underwent needle core biopsy to identify the basis for graft dysfunction; urine was collected prior to the biopsies. The remaining 107 samples were from patients deemed clinically stable and their plasma creatinine had improved or remained within 0.2 mg of the original value for 7 days prior to and after urine collection. Immunosuppression consisted of a cyclosporine- or tacrolimus-based regimen with antilymphocyte antibodies (OKT3 mAbs or ATG) used for steroid resistant acute rejection.

RNA Isolation. Urine was centrifuged at 10,000 g for 30 minutes at 4° C. RNA was extracted from the pellet utilizing the Rneasy® minikit, Qiagen Inc, Chatsworth, Calif. One microgram ($\mu$g) of RNA was reverse-transcribed to cDNA using Moloney murine leukemia virus transcriptase.

Figure 3:
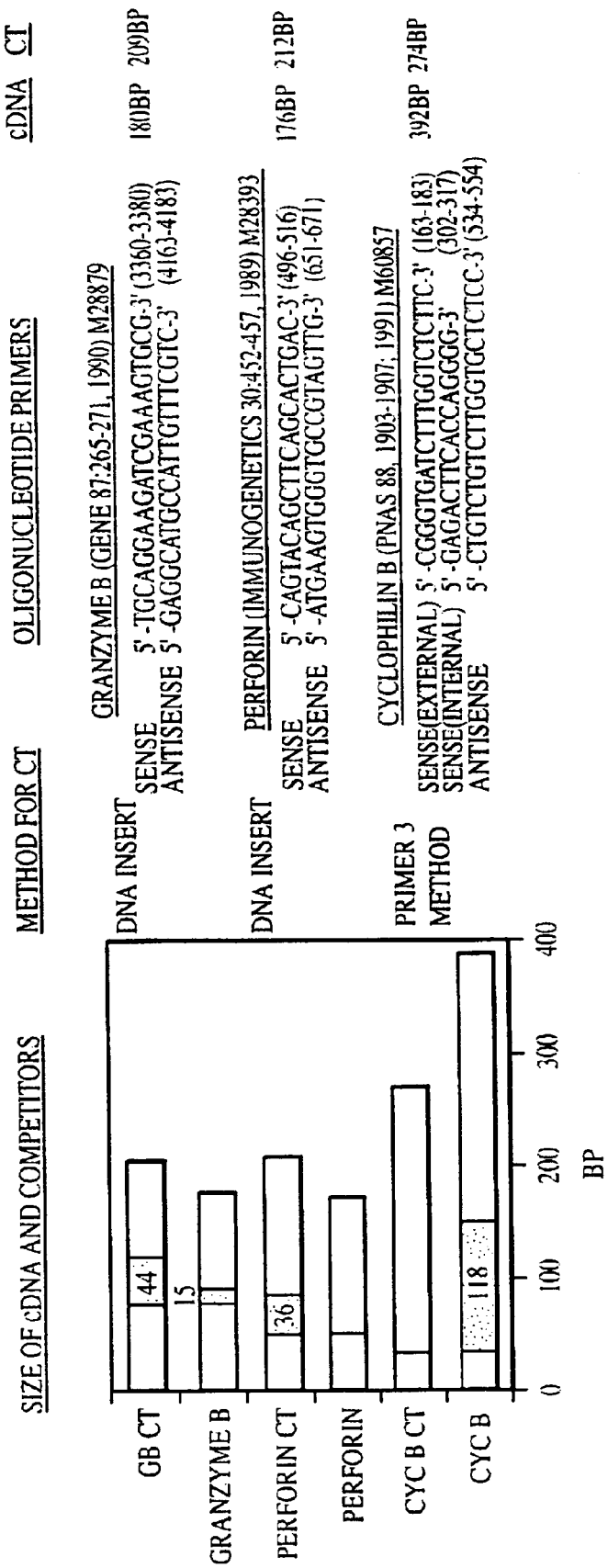
FIG. 3 depicts the design and construction of competitor DNA constructs. Granzyme B competitor DNA construct (GB CT) and perforin competitor DNA CT were constructed by digestion of the 180 bp granzyme B wild type PCR product with MseI, and by digestion of the 176 bp perform wild type PCR product with NlaIII, and ligation of the respective subfragments with a 44 bp (granzyme B) or 36 bp (perforin) DNA insert with appropriate cohesive ends at the 5' and 3' ends. The 274 bp cyclophilin B competitor (Cyc B CT) was amplified using a modified sense primer that contains at its 5' end the external sense primer and at its 3' end, a 16 bp sub-fragment internal sense primer SEQ ID NOs 42–48 respectively corresponding to sequences (302–317) within the wild-type PCR product.

Construction of Gene Specific DNA Competitors and Quantitative PCR. Our design and construction of gene specific DNA competitor constructs are illustrated in FIG. 3. cDNA was co-amplified with different concentrations of granzyme B, perforin, or cyclophilin B DNA competitors. The PCR products were resolved by electrophoresis, visualized by ethidium bromide staining, and photographed and scanned by laser densitometry. The concentrations of wild-type gene transcripts were quantified by measuring the ratio of cDNA band vs. specific competitor band. Transcript levels were expressed in femtograms (fg) specific mRNA per $\mu$g of RNA.

Statistical Analysis. SAS (Statistical Analysis Software) was used for data analysis. Prior to comparison of mRNA steady-state levels among the various diagnostic categories, distributions of transcript levels were examined for non-normality. mRNA levels of perforin, granzyme B and cyclophilin B exhibited significant deviation from a normal distribution (p=0.000 1), which was reduced by use of a log transformation. The logged mRNA steady state levels were used as the dependent variable in a one-way mixed-level ANOVA to compare levels across the different diagnostic groups. Mixed-level models were used to handle the non-independence due to multiple urine specimens from some patients. Dunnett's test was used to compare acute rejection mRNA levels against levels found in the other, chronic allograft nephropathy (CAN), stable, or delayed graft function (DGF) group. Receiver operator characteristic curve analysis of mRNA levels was used to determine cutpoints (thresholds) that yield the highest combined sensitivity and specificity for distinguishing patients with acute rejection from those without acute rejection. Area under the curve (AUC) was calculated and Fisher's exact test was used to calculate p-values for the odds ratios (OR) when cutpoints were used to define categorical variables.

Results

Histological Classification of Renal Allograft Biopsies. The Banff 97 classification was used to categorize the biopsies as acute rejection (n=24), CAN (n=5) or other (n=5). Of the 24 acute rejection biopsies, two were graded as borderline, six as type IA (focal moderate tubulitis), eight as type IB (severe tubulitis), five as type IIA (mild to moderate intimal arteritis), two as type IIB (severe intimal arteritis), and one as type III (transmural arteritis). The clinical diagnosis, as assessed by response to anti-rejection therapy with steroids or anti-lymphocyte antibodies (22/24) or by histological analysis of nephrectomy specimens (2/24) was consistent with biopsy classification as acute rejection. Two of the acute rejection biopsies showed features of CAN (one showed severe interstitial fibrosis and tubular atrophy and tubular loss [grade III CAN]; the other showed moderate [grade III changes). Among the 5 biopsies classified as CAN, 3 showed grade II CAN and 2 showed grade I changes. Among the 15 biopsies classified as other, 7 were diagnosed as toxic tubulopathy (TT), 4 as non-specific changes, 3 as acute tubular necrosis (ATN), and one as renal vein thrombosis (RVT).

Twenty of 24 acute rejection biopsies, all 15 classified as other, and one from the CAN group, were obtained within 6 months of transplantation.

mRNA Levels in Urinary Cells. mRNA levels of perforin and granzyme B, but not those of constitutively expressed cyclophilin B, were higher in urinary cells from patients with acute rejection compared to those without acute rejection. The mean±SEM of perforin mRNA levels (log transformed values) in the acute rejection group (n=24) was 1.43±0.26 fg and was −0.61±0.20 fg in the group (n=127) without acute rejection (t=6.26, p<0.0001). The mean±SEM of granzyme B mRNA levels was 1.24±0.24 fg in the acute rejection group and was −0.88±0.19 fg in patients without acute rejection (t=6.82, p<0.0001). The mean±SEM of cyclophilin B mRNA levels was 2.26±0.34 fg in the acute rejection group and was 2.47±0.12 fg in the group without acute rejection (t=0.60, P=0.55).

Figure 4A:
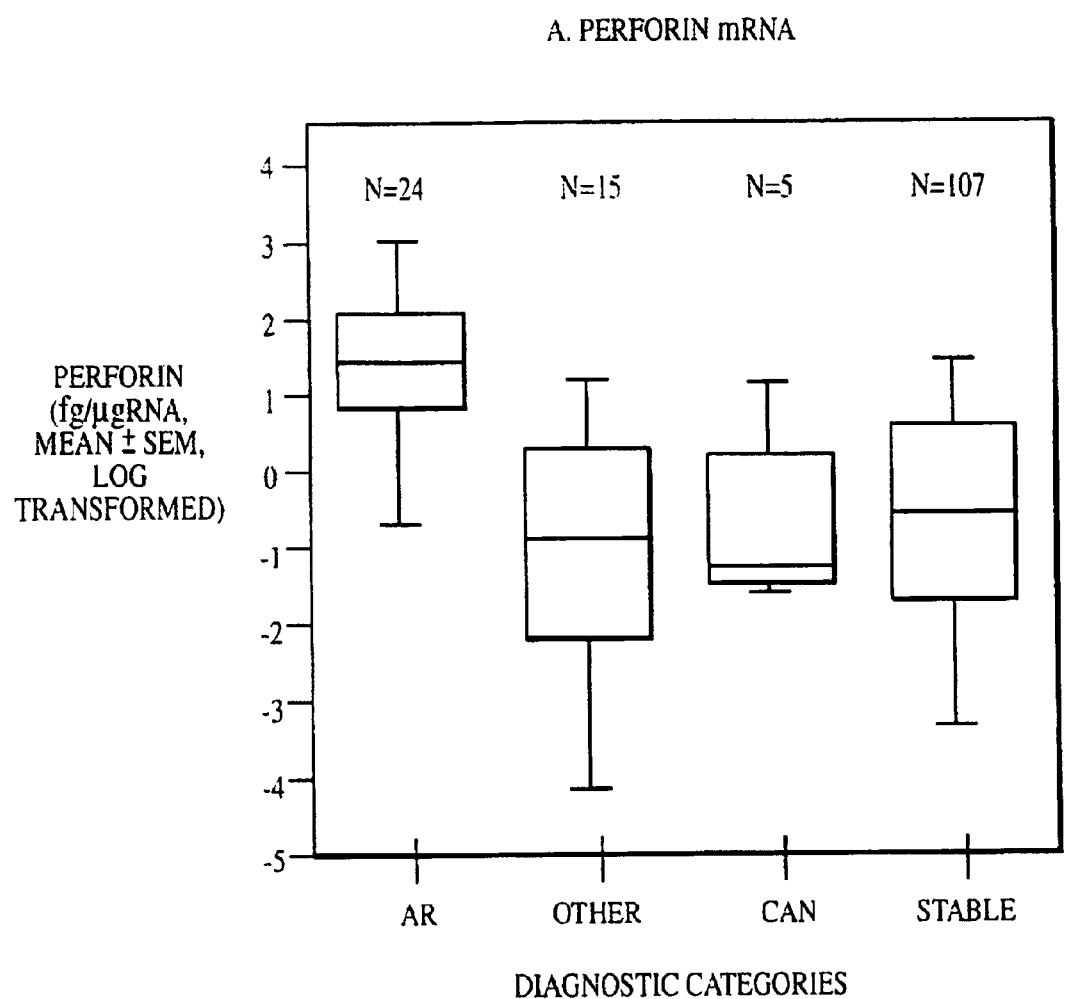
FIG. 4 illustrates levels of mRNA levels in urinary cells. Box and whisker plots show the $10^{th}$, $25^{th}$, $50^{th}$, (median), $75^{th}$, $90^{th}$ percentile mRNA values for perforin mRNA (A), granzyme B mRNA (B), and cyclophilin B mRNA (C) in samples classified as acute rejection (AR), Other (acute tubular necrosis, toxic tubulopathy or non-specific changes), chronic allograft nephropathy (CAN) or the stable group. mRNA levels of perforin and granzyme B, but not those of cyclophilin B were higher in the acute rejection group compared to all other diagnostic categories (p=0.0001, one-way mixed-level ANOVA) (N=number of urine samples quantified for mRNA levels).
Figure 4B:
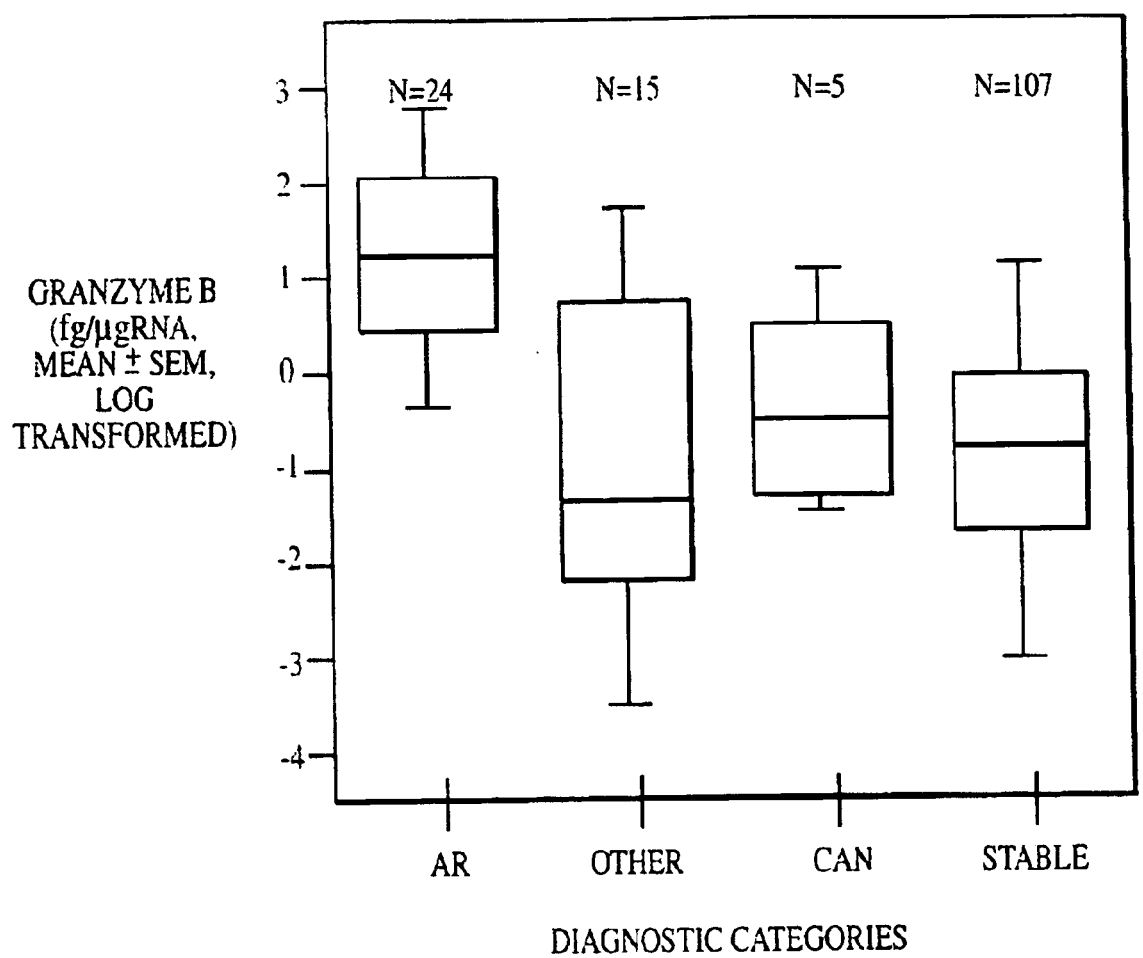
Figure 4C:
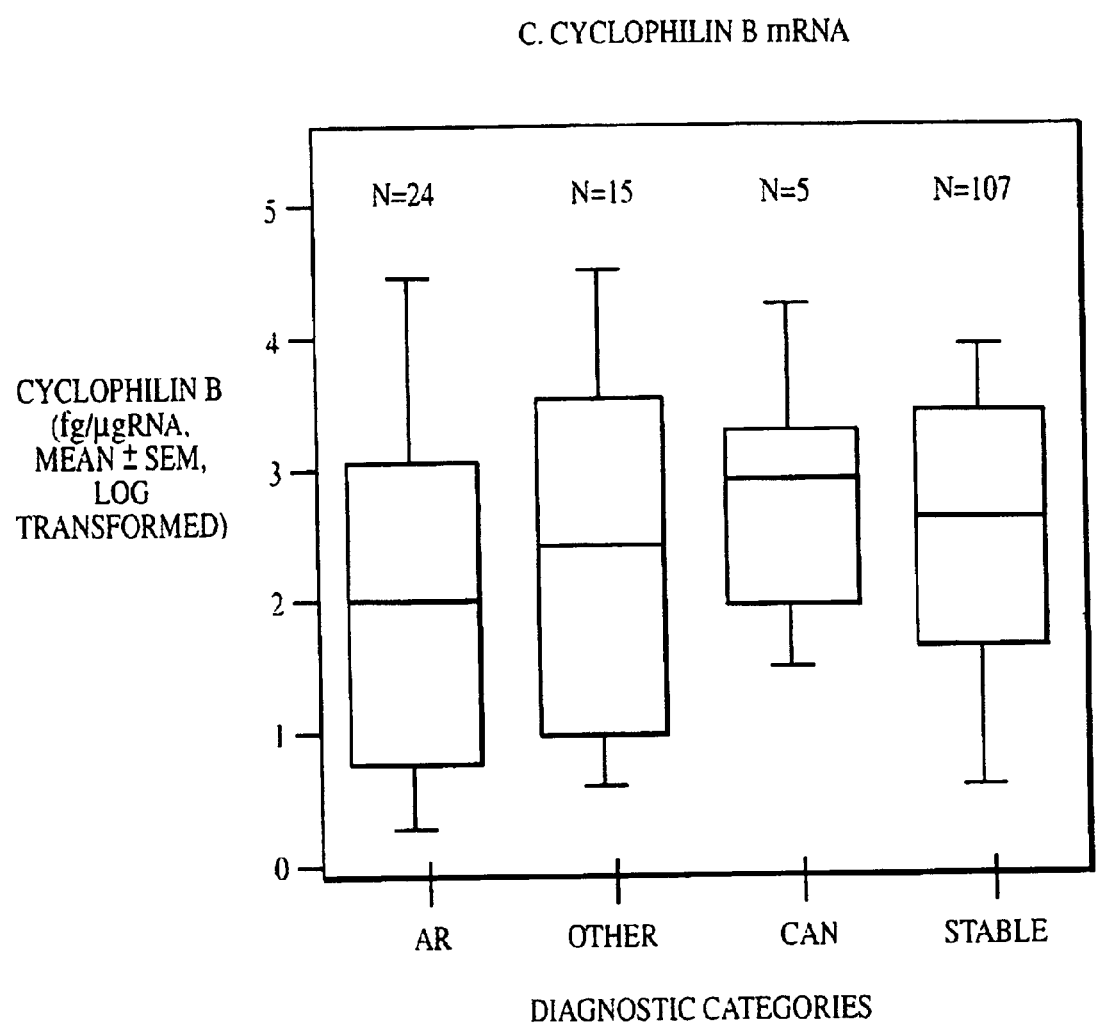

The group without acute rejection included samples from the stable group (n=107), the other group (n=15) and the CAN group (n=5). Table 1 compares mRNA levels of perforin, granzyme B and cyclophilin B across the four diagnostic categories: acute rejection, other, CAN, or stable. In FIG. 4, box and whisker plots illustrate the $10^{th}$, $25^{th}$, $50^{th}$ (median), $75^{th}$ and $90^{th}$ percentile mRNA values for the four diagnoses.

Perforin mRNA levels were highest in the urinary cells obtained from patients with histologically validated acute rejection (Table 1, FIG. 4). Comparison of the mean perforin transcript levels across the four diagnostic categories demonstrated that the null hypothesis of equal group means should be rejected (F=13.39, p<0.0001, ANOVA, Table 1). Dunnett's test that controls for type I experiment-wise error rate revealed that perforin mRNA levels in urinary cells obtained during acute rejection were significantly higher than those in stable (p<0.00005), other (p=0.0004) and CAN (p=0.03).

Granzyme B mRNA levels were highest in the urinary cells from patients with acute rejection (Table 1, FIG. 4). Comparison of the mean granzyme B transcript levels across the four diagnostic categories demonstrated that the null hypothesis of equal group means should be rejected (F=15.57, p<0.0001, ANOVA, Table 1). Dunnett's test revealed that granzyme B mRNA levels in urinary cells obtained during acute rejection were significantly higher than those in stable (p<0.00005), and other (p=0.001), but not in CAN (p=0.12).

Cyclophilin B mRNA levels did not vary significantly among the four diagnostic categories (p=0.90, Table 1, FIG. 4). Consistent with this, none of the pair-wise comparisons of the acute rejection group with the other, chronic allograft nephropathy or stable groups were significant.

Sixteen of 24 acute rejection biopsies were obtained within 3 months of transplantation, mRNA levels of perforin or granzyme B in acute rejection biopsies obtained within or after 3 months were similar (perforin: 1.43±0.30 fg vs. 1.55±49 fg; granzyme B: 1.09±0.30 fg vs. 1.63±0.30 fg).

Figure 5A:
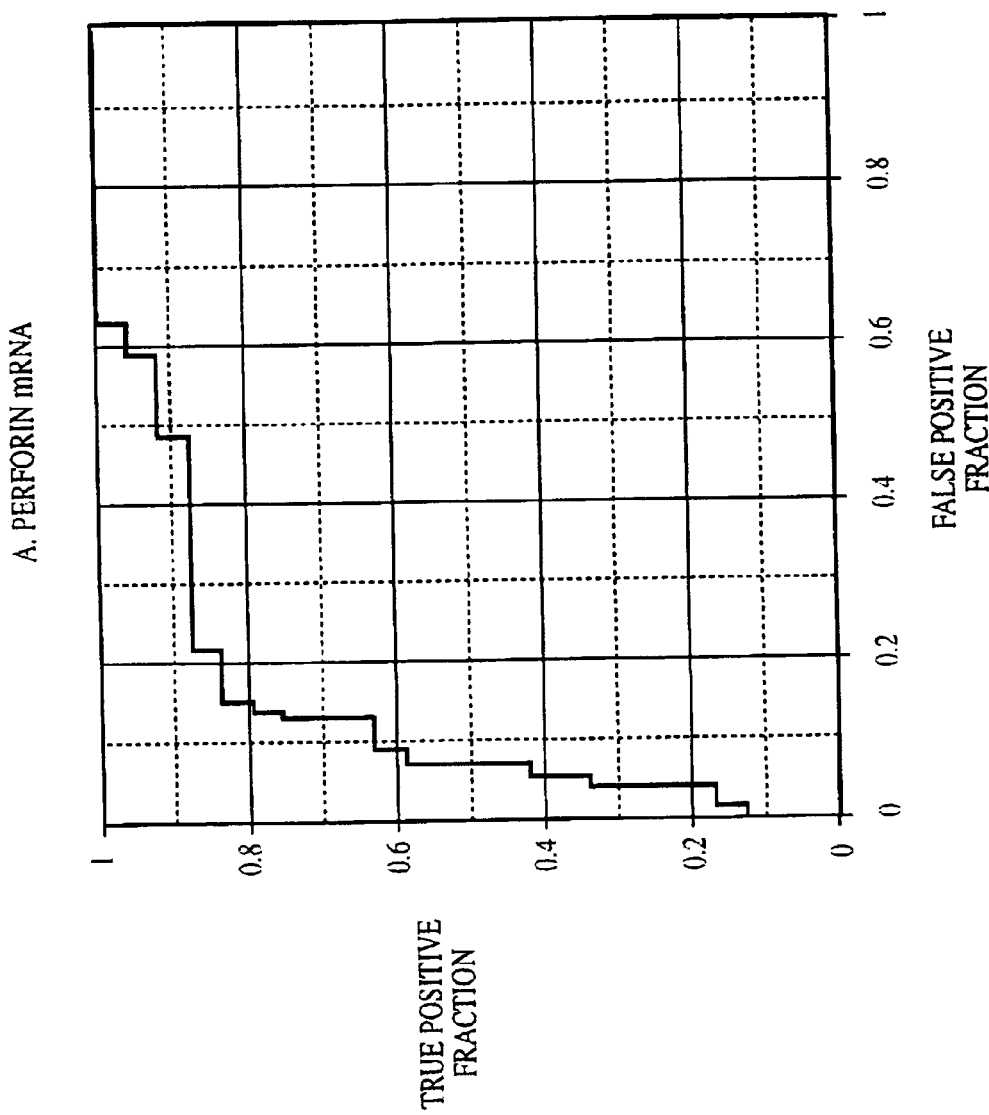
FIGS. 5A–C are graphs showing receiver operator curve analysis of mRNA levels. True positive fraction (sensitivity) and false positive fraction (1-specificity) computed using actual mRNA levels of perforin (A), granzyme B (B), and cyclophilin B (C) as biomarkers of acute rejection are illustrated. The calculated AUC was 0.863 for perforin mRNA levels, and 0.575 for cyclophilin B mRNA levels (0.5=chance performance and 1.0=perfect performance).
Figure 5B:
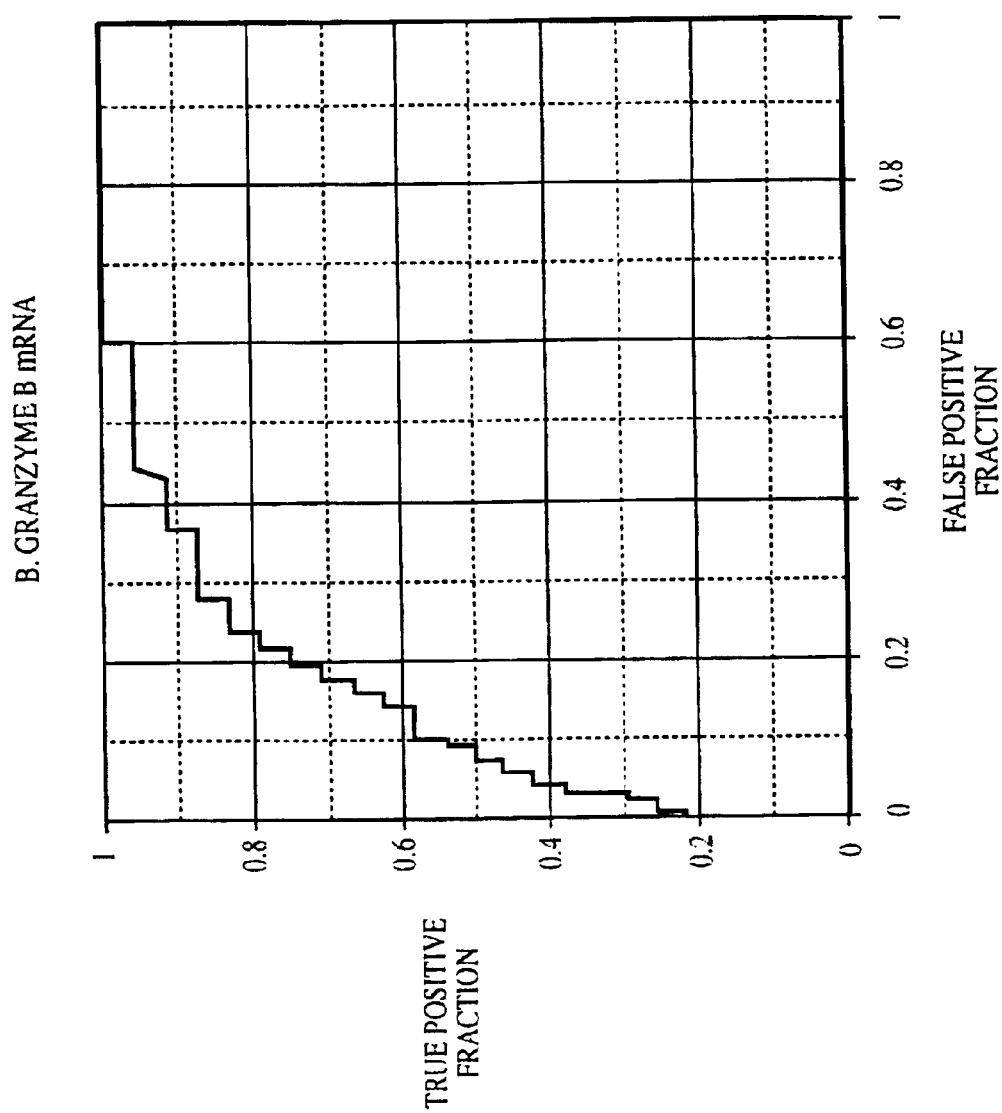

Receiver Operator Characteristic (ROC Curve Analysis of mRNA Levels). The ROC curves (FIG. 5) display the true positive fractions (sensitivity) and false positive fractions (specificity) for various cutpoints for mRNA levels of perforin (panel A), granzyme B (panel B), and cyclophilin (panel C). The best rule-in (specificity) and rule-out (sensitivity) decision thresholds for perforin were between 2.35 and 2.51 (non-transformed values) and at this threshold, sensitivity for predicting acute rejection was 83% and specificity was 84% (FIG. 5A, AUC=0.863, OR=27, 95% CI=8.3 to 87, p=0.00001). The best specificity and sensitivity values for granzymne B were observed for cutpoints between 1.41 and 1.51 and at this threshold, sensitivity was 79% and specificity was 78% (FIG. 5B, AUC=0.861, OR=13, 95% Cl=4.6 to 39, p=0.00001).

Figure 5C:
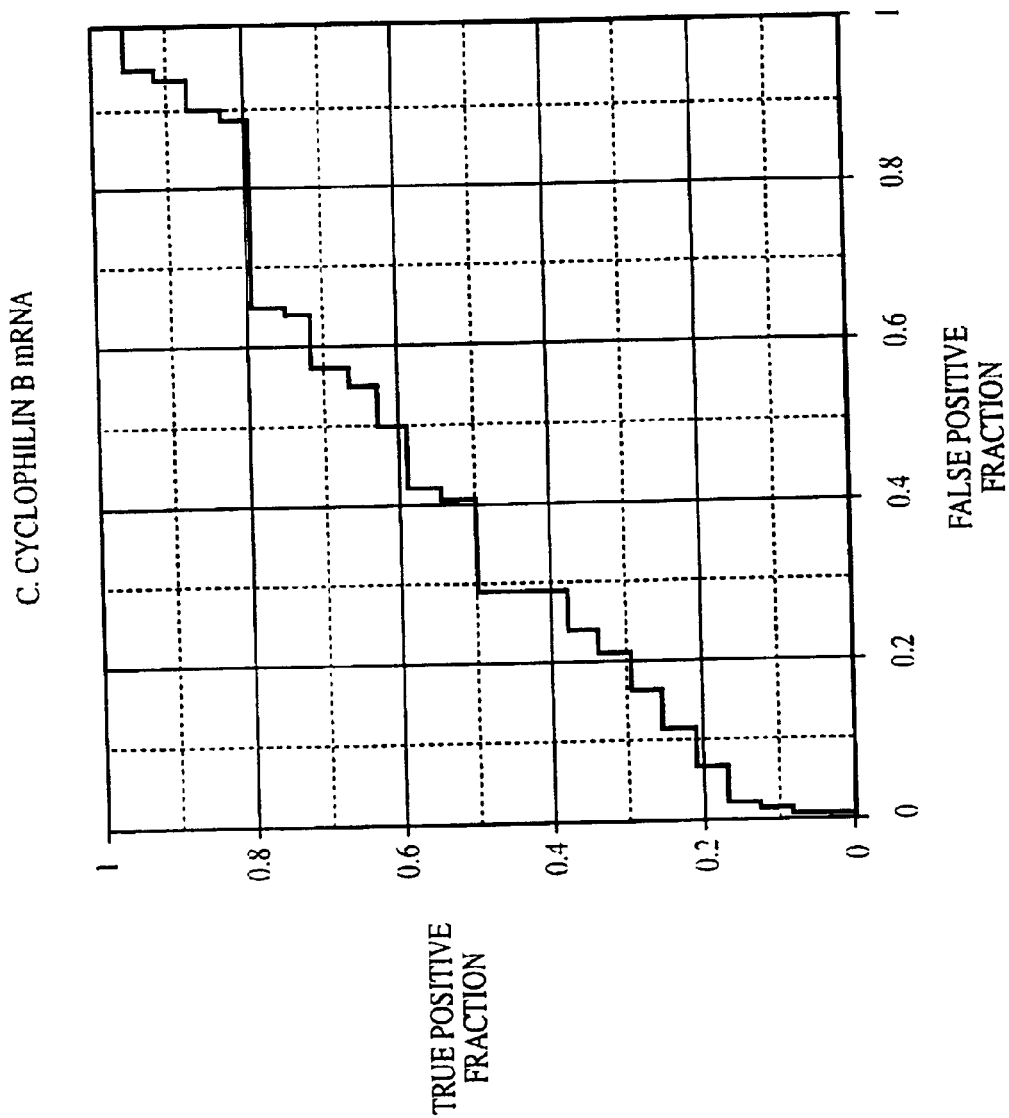

FIG. 5C shows the ROC curve (AUC=0.575) for cyclophilin B mRNA with respect to presence or absence of acute rejection. The analysis showed that cyclophilin B mRNA levels do not discriminate acute rejection from other renal diagnoses.

ROC curve analysis, shown in FIG. 5, included all 151 urine specimens evaluated for transcript levels. Forty-four samples were from patients who had undergone renal allograft biopsy, and 107 were from patients classified as stable on the basis of clinical criteria. Whereas the presence or absence of acute rejection is known with a high degree of certainty in patients who had undergone allograft biopsy, the possibility exists that some patients classified as stable on a clinical basis might harbor histologic changes of acute rejection. In order to eliminate this variable, we repeated the ROC analysis using only the patients who had undergone allograft biopsy. This evaluation demonstrated that mRNA levels of perforin (AUC—0.892, 83% sensitivity and 85% specificity for a cutpoint of 2.43, OR=28, 95% CI=5.5 to 145, p—0.0000 1) and granzyme B (AUC—0.823, 79% sensitivity and 65% specificity for a cutpoint of 1.46, OR=7.1, 95% CI=1.8 to 27, p=0.005) but not those of cyclophilin B (AUC=0.573) are of diagnostic value (Table 2).

Renal Graft Recipients with DGF. Ten of eleven biopsies in patients with delayed graft function (DGF) (the clinical diagnosis of DGF was based on patients requiring dialysis in the first post-transplantation week) showed ATN, TT, or non-specific changes, and one showed ATN as well as acute rejection. mRNA levels of perforin or granzyme B were significantly lower in the urine samples (n=19) from patients with DGF due to non-immunological causes compared to samples (n=24) from patients with acute rejection (−0.65±0.48 fg vs. 1.43±0.26 fg, p<0.0007, for perforin and −0.48±0.43 fg vs.1.24±0.24 fg, p<0.002, for granzyme B). mRNA levels of perforin or granzyme B in the only patient with the clinical diagnosis of DGF and histologic diagnosis of acute rejection were 1.05 fg and 1.25 fg, respectively, and were similar to those in the acute rejection group.

Cyclophilin B mRNA levels did not distinguish DGF due to non-immune causes from acute rejection (2.59±0.30 fg vs. 2.26±0.34 fg, p=0.46).

Figure 6A:
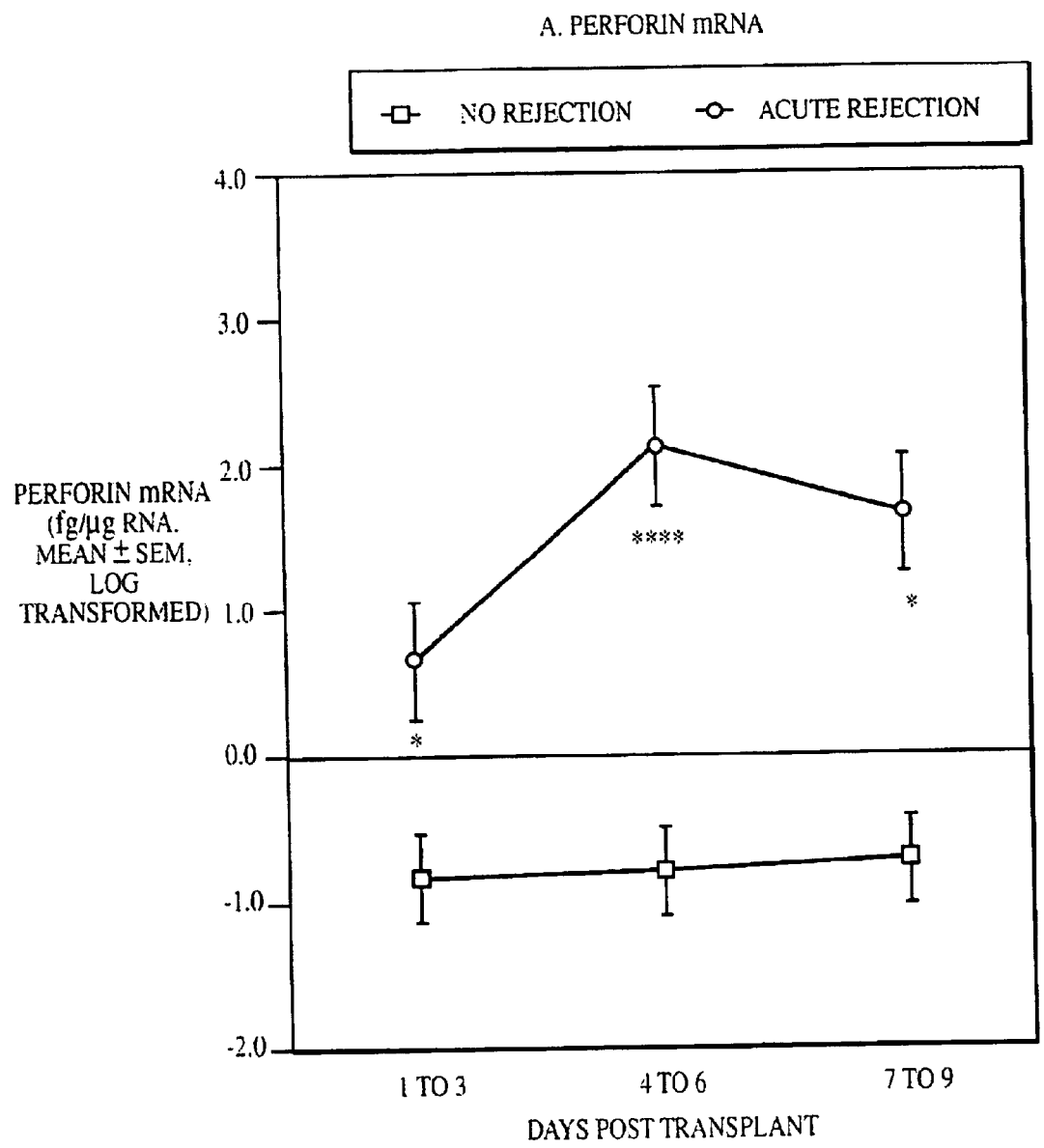
FIGS. 6A–C illustrates mRNA levels in sequential urine samples. mRNA encoding perforin (A), granzyme B (B) or cyclophilin B (C) were quantified in urine samples obtained in the first 10 days of transplantation. mRNA levels of perforin or granzyme but not those of cyclophilin B were lower in patients (n=29) who did not develop acute rejection within the first 10 days of transplantation (indicated by filled boxes) (43 samples from post-transplant days 1, 2 or 3; 26 samples from days 4, 5, or 6; 14 samples from days 7, 8 or 9) as compared to patients (n=8) who develop acute rejection within the first 10 days of transplantation (indicated by filled circles) (6 samples from days 1, 2 or 3; 5 samples from days 4, 5 or 6; 6 samples from days 7, 8 or 9).
Figure 6B:
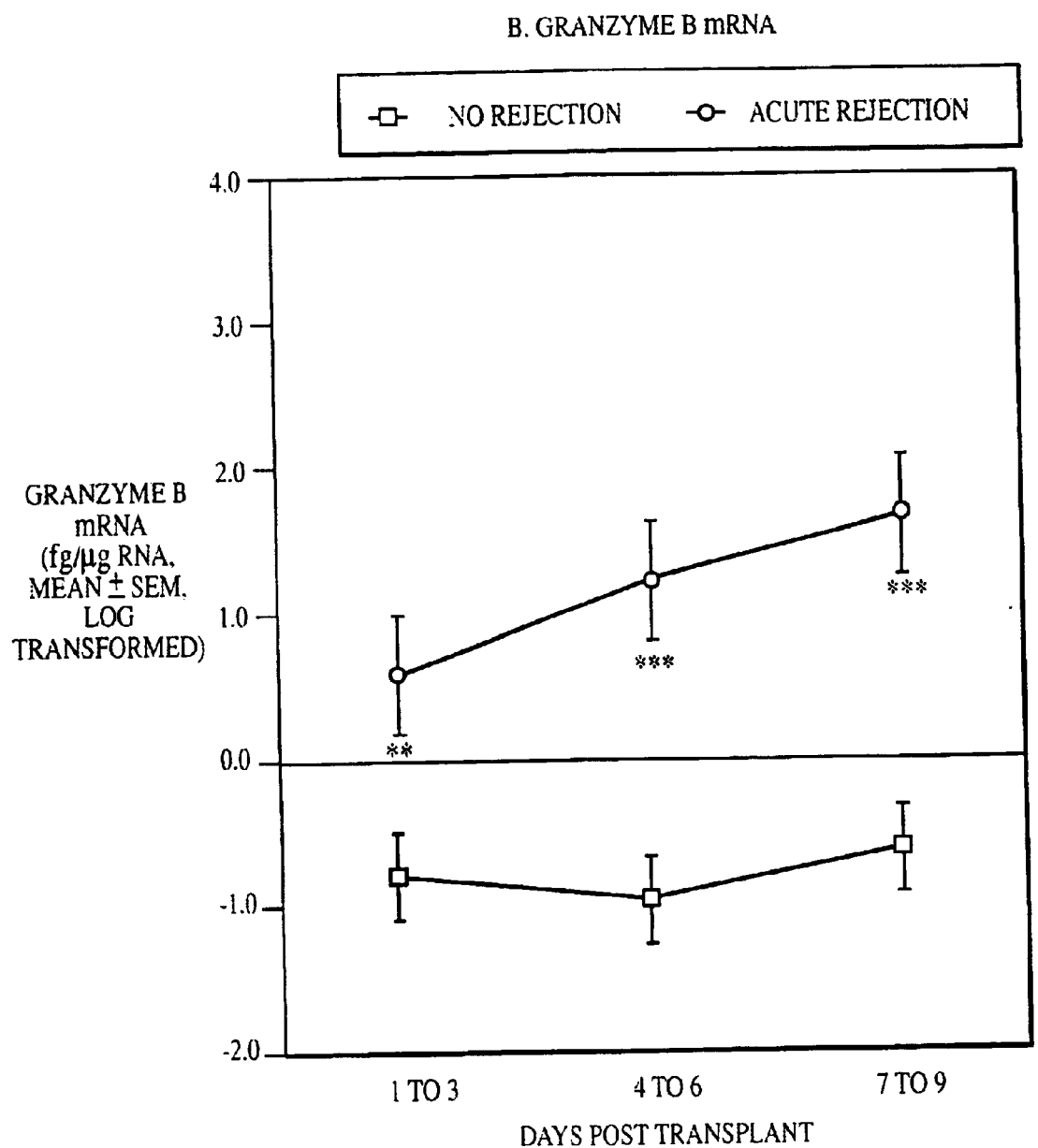
Figure 6C:
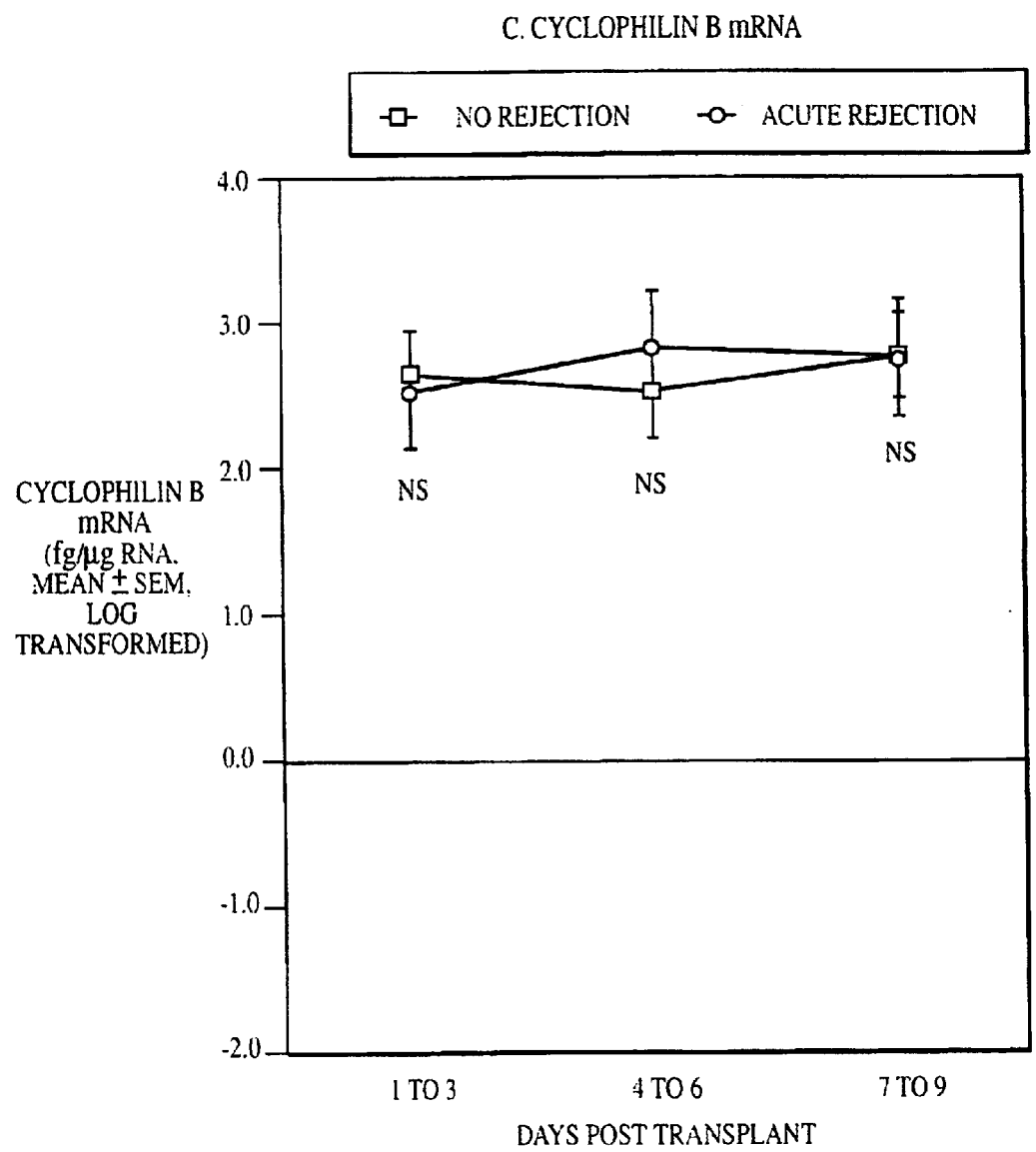

Serial Studies in the Early Post-Transplantation Period.
Sequential urine samples were obtained within the first 10 days of transplantation from 37 patients. FIG. 6 compares the levels of mRNA encoding perforin, granzyme B or cyclophilin B in patients (n=29) who did not develop acute rejection within 10 days of transplantation with patients (n=8) who developed acute rejection within the first 10 days. mRNA levels of perforin (FIG. 6A) and granzyme B (FIG. 6B) but not those of cyclophilin B (FIG. 6C) were significantly lower in patients who did not develop acute rejection compared to the patients who did.

TABLE 5

Quantification of mRNA encoding perforin, granzyme B or cyclophilin B in urinary cells.

| mRNA[a] | Renal Diagnosis[b] | | | | p[c] |
|---|---|---|---|---|---|
| | AR (n = 24) | Other (n = 15) | CAN (n = 5) | Stable (n = 107) | |
| Perforin | 1.43 ± 0.26 | −0.79 ± 0.48 | −0.68 ± 0.75 | −0.58 ± 0.21 | 0.0001 |
| Granzyme B | 1.24 ± 0.24 | −0.70 ± 0.46 | −0.33 ± 0.72 | −0.93 ± 0.20 | 0.0001 |
| Cyclophilin B | 2.26 ± 0.34 | 2.42 ± 0.33 | 2.74 ± 0.56 | 2.46 ± 0.12 | 0.90 |

[a]mRNA were quantified using gene specific competitor template (FIG. 3) in competitive quantitative PCR and are expressed as fg mRNA/µg of total RNA. Arithmetic mean ± SEM of mRNA levels (log transformed) are shown.
[b]Renal diagnoses of acute rejection (AR); acute tubular necrosis and/or toxic tubulopathy, non-specific changes (other); or chronic allograft nephropathy (CAN) were made by histological classification of renal allograft biopsies. Diagnosis of "Stable" was made on the basis of clinical criteria.
[c]p values were calculated using log-transformed mRNA levels as the dependent variable in one-way ANOVA (F-test)

TABLE 6

Urinary mRNA levels and acute rejection.

| mRNA Levels[a] | | Acute Rejection[b] | | p[c] |
|---|---|---|---|---|
| | | Present (n = 24) | Absent (n = 20) | |
| Perforin | >2.43 | 20 | 3 | |
| | <2.43 | 4 | 17 | 0.00001 |
| Granzyme B | >1.46 | 19 | 7 | |
| | <1.46 | 5 | 13 | 0.005 |

[a]ROC analysis was used to select the best rule-in and rule-out decision thresholds (cut points of actual mRNA levels measured in fg/µg).
[b]The presence or absence of acute rejection was established by renal allograft biopsy.
[c]p-value derived using Fisher's exact test.

Discussion

Our findings demonstrate that acute renal allograft rejection, a significant and treatable risk factor for allograft failure, can be diagnosed accurately and non-invasively by quantification of cytotoxic genes perforin and granzyme B in urinary cells.

Recipients with DGF have inferior graft survival rates, and are at higher risk for acute rejection, compared to patients with immediate graft function. DGF can result from non-immunologic causes, immunologic causes, or a combination of both. Serum creatinine values are uninformative, and biopsy is mandatory to establish the cause of DGF. Our data that patients with DGF due to non-immunologic causes can be distinguished from patients with acute rejection gain additional significance.

Our studies using gene specific competitor DNA constructs in quantitative PCR demonstrate that acute rejection of renal allografts can be diagnosed accurately and non-invasively by quantification of perforin mRNA and granzyme B mRNA in urinary cells. In addition to functioning as surrogates for allograft biopsies, mRNA phenotyping of urinary cells can lead to the molecular classification of rejection and identification of suitable therapeutic targets.

EXAMPLE 5

Method for Diagnosing Cardiac Allograft Rejection

A series of 29 samples of endomyocardial biopsies (EMBs) obtained from 11 adult cardiac transplant recipients within the first six months post-transplantation was evaluated for the presence of mRNA for perforin, granzyme B and FasL, using the quantitative competitive RT-PCR method. Twelve biopsies with at least grade 1B, according to the ISHLT criteria, were considered with R. Zero grade EMBs that were followed within 15 days by a EMB with R were considered as pre-rejection (pre-R) biopsies (n=6); otherwise, the 0 grade biopsies were considered without R (n=11). All three molecules were up-regulated in the EMBs with R compared to the EMBs without R (medians: granzyme B, 0.53 vs. 0.09; perforin, 0.31 vs. 0; FasL, 0.57 vs. 0.36; $p<0.05$ in all these comparisons). Expression of granzyme and FasL mRNA was higher in pre-R EMBs than in EMBs without R (medians: 0.4 vs. 0.09, for granzyme B, $p<0.04$; 0.61 vs. 0.36, for FasL, $p<0.06$). All the EMBs in the pre-R group and 92% of the EMBs with R presented up-regulation of any two molecules, in contrast to 36% of EMBs without R ($p<0.04$).

Results

These data indicate that heightened intragraft expression of cytotoxic molecules (perforin, granzyme B, FasL) is associated not only with ongoing, but also with impending rejection. Therefore, the cytotoxic lymphocyte genes analysis within EMB represent a valuable tool in the monitoring of cardiac allograft rejection, specially considering that it could have predictive value for the occurrence of acute rejection. Furthermore, monitoring of body fluids such as blood, pleural fluid or peri-cardial fluid (understood to be fluid that is sequestered around the heart whether or not it is contained within a pericardial sac) may permit sampling of peripheral lymphocytes to permit the same diagnostic conclusions to be drawn.

EXAMPLE 6

Method for Diagnosing Rejection of a Lung Allograft

In a patient status post lung transplantation, fluids may be collected from chest tube drainage or from bronchoalveolar lavage to assess for the presence of mRNA for perforin, granzyme B and FasL, using the quantitative competitive RT-PCR method. In using chest tube drainage fluid, an aliquot of pleural fluid could be extracted from the patient's chest tube using sterile technique. In using bronchoalveolar lavage fluid, bronchoalveolar lavage could be performed using standard techniques, with a fluid sample being extracted from the bronchial passages of the allograft. After being obtained, the fluid sample would be centrifuged to obtain a pellet and a supernatant. The latter would be removed, and the pellet would then be subjected to RNA extraction techniques as previously described. Design and construction of gene specific DNA competitor templates may be carried out using techniques well-known in the art.

In one study, a cohort of lung transplantation patients could be evaluated for incipient or established acute rejection. In the study patients, a set of fluid samples (for example, chest tube fluid, aspirated pleural fluid or bronchoalveolar lavage fluid) could be extracted at intervals following transplantation, accompanied by a set of lung biopsy samples obtained using conventional methods. Fluid samples and biopsies could be obtained at surveillance intervals deemed to be clinically relevant. The fluid and biopsy samples could then be evaluated for the presence of mRNA for perforin, granzyme B and FasL, using the quantitative competitive RT-PCR method. The degree of rejection in the biopsy samples could then be evaluated, using the ISHLT criteria. The degree of upregulation in the perforin, granzyme B and FasL molecules could then be evaluated and compared with the extent of rejection present in the correlated biopsy specimens. Upregulation of any two molecules would be indicative of incipient rejection, even in the absence of histological indicators.

EXAMPLE 7

Expression of Cytoprotective Genes in Human Renal Allograft Rejection

Materials and Methods

Tissue preparation. Thirty-one kidney transplant biopsies were investigated for gene expression of the protective genes (A20, BCl-$X_L$, HO-1), and the housekeeping gene glyceraldehyde-3-phosphate dehydrogenase (GAPDH). Thirty-one biopsies were obtained from 28 patients to clarify the cause of graft dysfunction. Biopsy cores were subdivided at the bed-side and immediately snap frozen in liquid nitrogen and stored at −80° C. for quantitative RT-PCR studies and imbeded in OCT (Sakura. Finetek USA, Torrance, Calif.) in pre-chilled isopentane and prepared for immunohistologic studies. The majority of each sample was used for routine histopathological diagnosis.

RNA isolation. Procedures for isolation of tissue RNA and reverse transcription into cDNA were performed as previous described in detail. In brief, total RNA was isolated by tissue homogenization in guanidine isothiocyanate/2-mercaptoethanol and ultracentrifagation in CsCl, using Qiagen RNeasy kit (QIAGEN Inc, Chatworth, Calif.). One microgram of RNA was reverse transcribed by Maloney murine leukemia virus transcriptase and diluted to a final volume of 50 µl.

Quantification of gene expression by competitive template RT-PCR. 2 µl cDNA was co-amplified with different concentrations of A20, HO-1, BCl-$X_L$ or GAPDH DNA competitor templates. The PCR products were detected by agarose gel electrophoresis, stained with 0.5% ethidium bromide, photographed in UV light and the negatives of the photograph were scanned by laser densitometry. The concentration of wild-type gene transcripts was quantified by measuring the ratio of cDNA band vs specific competitor band, using PC software from Bio-Rad's image analysis system (Bio-rad laboratories, Hercules, CA). Transcript levels were expressed in ferritogram. (fg) competitive template per fg of reversed transcribed cDNA.

Figure 7:
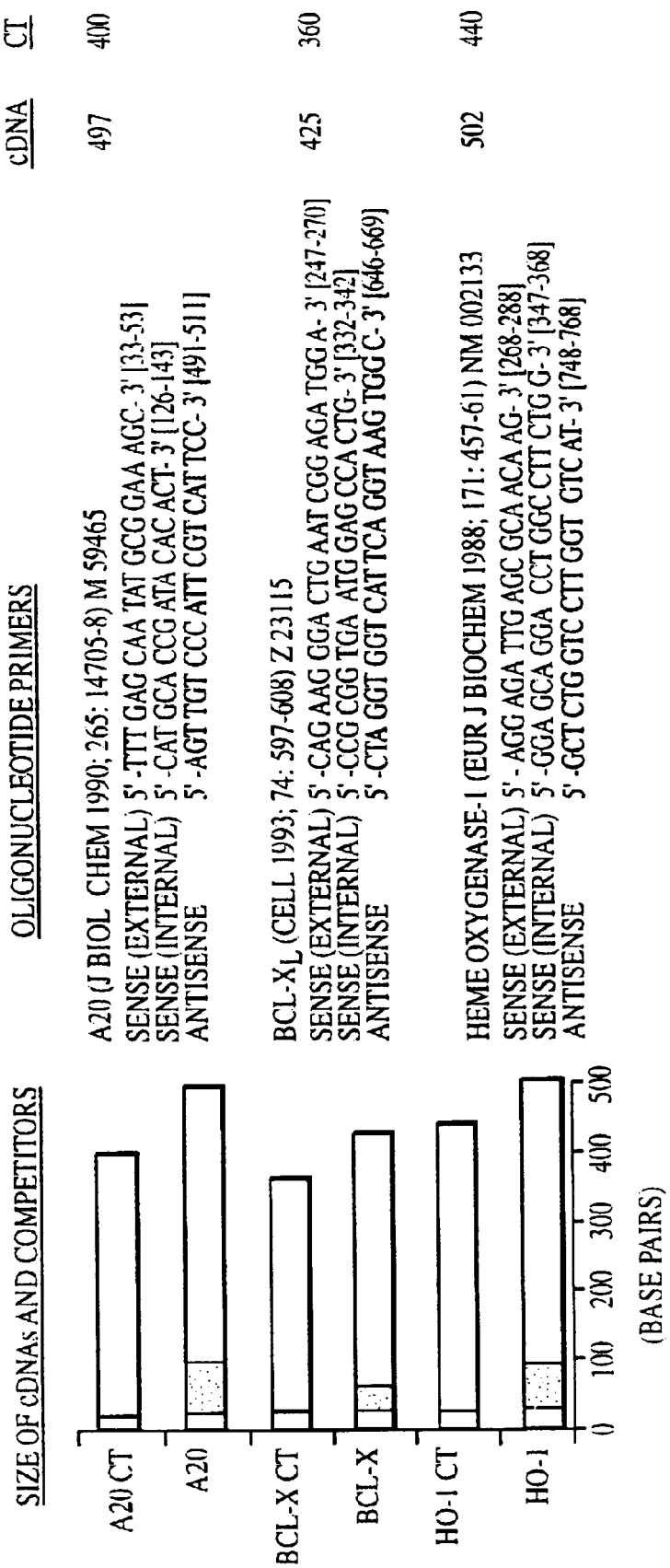
FIG. 7 illustrates the design and construction of competitor DNA constructs. The 400 bp A20 competitor, 366 bp BCl-$X_L$ competitor and 443 bp HO-1 competitor were amplified using modified sense primers that contain at their 5' ends the external sense primer and at their 3' ends sub-fragment internal sense primers SEQ ID NOs 31–41 corresponding to sequences within the wild type PCR product.

The 400 basepairs (bp) A20 specific DNA competitor, 366 bp BCI-XL Specific DNA competitor, and 443 bp HO-1 specific DNA competitor were constructed by one-step generation of a shortened DNA sequence by use of a specifically designed double-sense primer (FIG. 7). The sequences for the A20, Bcl-XL and HO-1 specific primers are as follows: A20: external sense primer, 5'-TTT GAG CAA TAT GCG GAA AGC-3' (SEQ ID NO: 33); internal sense primer, 5'-CAT GCA CCG ATA CAC ACT-3' (SEQ ID NO: 34); antisense primer, 5'-AGT TGT CCC ATT CGT CAT TCC-3' (SEQ ID NO: 35); BCI-$X_L$: external sense primer, 5'-CAG AAG GGA CTG AAT CGG AGA TGG A-3' (SEQ ID NO:36); internal sense primer 5'-CCG CGG TGA ATG GAG CCA CTG-3' (SEQ ID NO: 37); downstream primer, 5'-CTA GGT GGT CAT TCA GGT AAG TGG C-3' (SEQ ID NO:38). HO-1: external sense primer, 5'-AGG AGA TTG AGC GCA ACA AG-3' (SEQ ID NO: 39); internal sense primer, 5'-GGA GCA GGA CCT GGC CTT CTG G-3' (SEQ ID NO: 40); downstream primer, 5'-GCT CTG GTC CTT GGT GTC AT-3' (SEQ ID NO:41).

The magnitude of target gene expression is calculated as fg of target gene cDNA per ng of GAPDH cDNA in order to control for variation in each reverse-transcription reaction and PCR cycling.

Figure 8A:
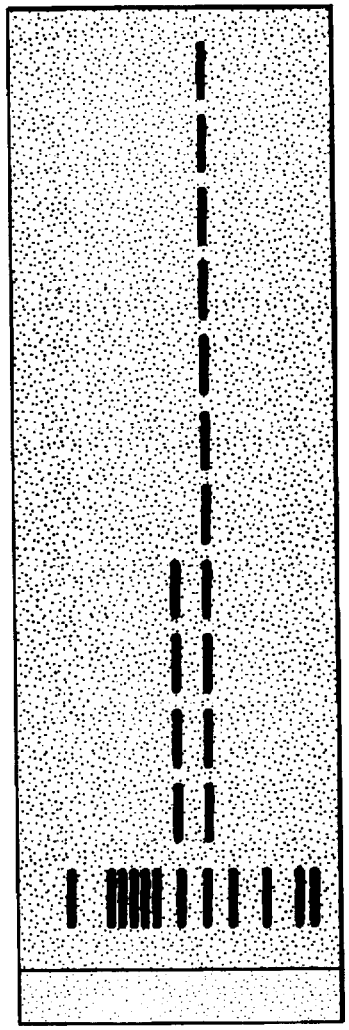
FIGS. 8A–B present (A) a gel and (B) a graph of standardization of ratios for differing concentrations of competitive template. A linear relationship is generated when plotting the concentrations of competitive template used against the ration of the densities of product from the wild-type and competitor cDNA PCR.
Figure 8B:
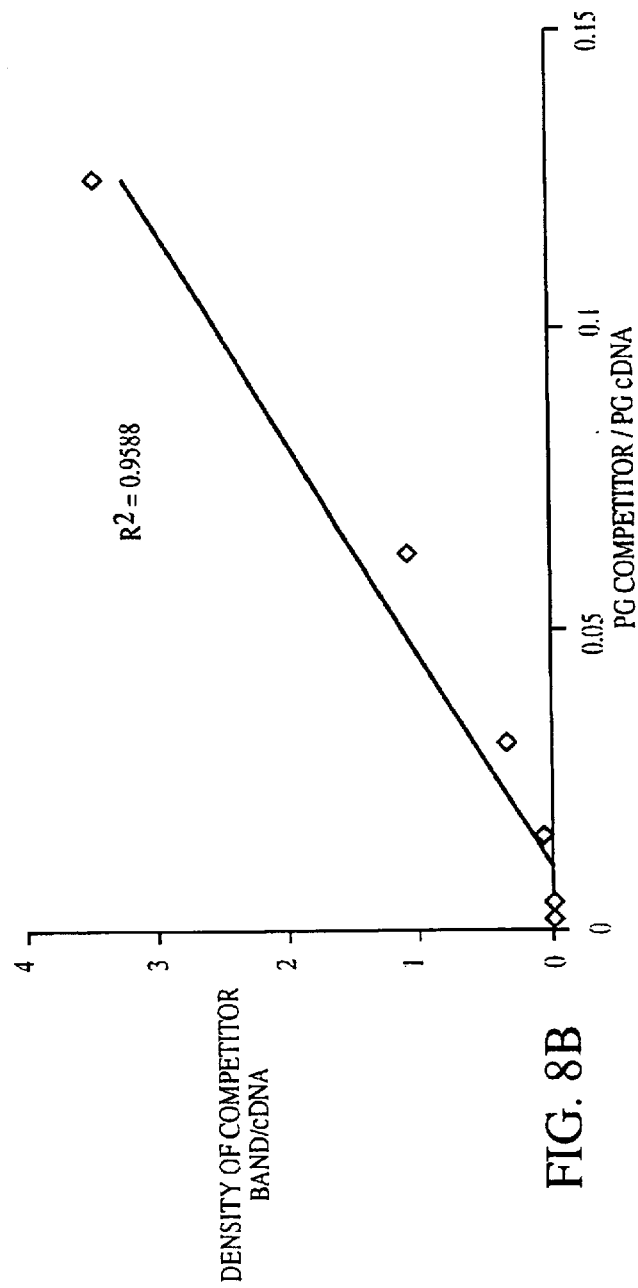

Standardization of quantification of gene expression. Known amount of cDNA per competitor ratio was used to make a standard curve of each gene expression (FIG. 8). Linear correlation between band density and amount of cDNA ratio was established. The amount of specific gene transcript present in the initial cDNA from each sample is calculated from the formula y=mx+b (generated from the standard curve).

Immunohistochemistry. The protective proteins expression were studied by immunohistochemistry staining as previous described. In brief, the frozen specimens (n=8) were cut into 5-$\mu$m sections in a cryostat at $-25°$ C. and air-dried. Intragraft protective protein products were stained with rabbit polyclonal anti-human A20 (V. Dixit, Ann Arbor, Minn.), Bcl-XL (C. Thompson, Chicago, Ill.) and goat polyclonal antibody against human HO-I (Santa Cruz Biotechnology, Santa Cruz, Calif.). The sections were counterstained with Hematoxylin and Eosin staining.

Statistics. SPSS (Statistical Analysis Software, version 7.5) was used for data analysis. The results are expressed as arithmetic means ($\pm$SEM). Statistical comparisons between groups were performed by non-parametric t-test. The difference was considered significant when P<0.05.

Results

Patients demographics. Thirty-one allograft tissue specimens were obtained from 28 patients. We divided the patients into 3 groups according to histopathology. There were nonrejection (n=13), acute rejection (n=9) and chronic rejection (n=9). The majority of patients (90%) had received triple immunosuppressive drugs. Only 3 patients had dual immunosuppressive drugs without steroids. As shown in table 7, there were no differences between patients with acute rejection and non rejection in terms of age, cadaveric transplant, serum creatinine at the biopsy time, or incidence of diabetes. The biopsy time after transplantation of the acute rejection group was shortest due to the immunologic activity. There were more diabetes patients in chronic rejection group. However, no evidence of diabetic nephropathy was present in the histopathology study.

Figure 9A:
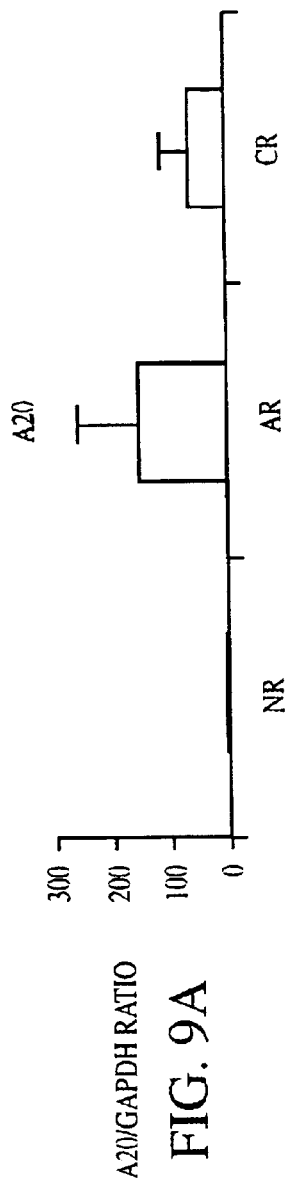
FIGS. 9A–C are graphs of the quantitative analysis of A20 (A), HO-1 (B) and Bcl-$X_L$ (C) mRNA transcripts. A) The mean+/–SEM of A20 mRNA transcript (fg/ng GAPDH) from allografts. B) The mean+/–SEM of HO-1 mRNA transcript (fg/ng GAPDH) from allografts. C) The mean+/–SEM of Bcl-$X_L$ mRNA transcript (fg/ng GAPDH) from allografts. AR: acute rejection, CR: chronic rejection, NR: nonrejection.

Heightened A20 gene expression in acute and chronic rejection. We tested the hypothesis whether A20 gene expression is changed during allograft rejection. By using the quantitative RT-PCR, we found that A20 gene was up-regulated in both acute rejection and chronic rejection compared to nonrejection The mean $\pm$SEM of A20 mRNA levels (fg/ng GAPDH) was 163$\pm$110 in AR group, was 67$\pm$25 in CR group, and was 5$\pm$3 in NR group (p=0.002) (FIG. 9A). All samples (100%) from acute rejection and 8 of 9 cases (89%) from chronic rejection expressed A20 whereas 4 of 13 cases (30%) from non rejection expressed the gene. There was no correlation between levels of A20 expression and severity or steroid-resistant rejection (data not shown).

Figure 9B:
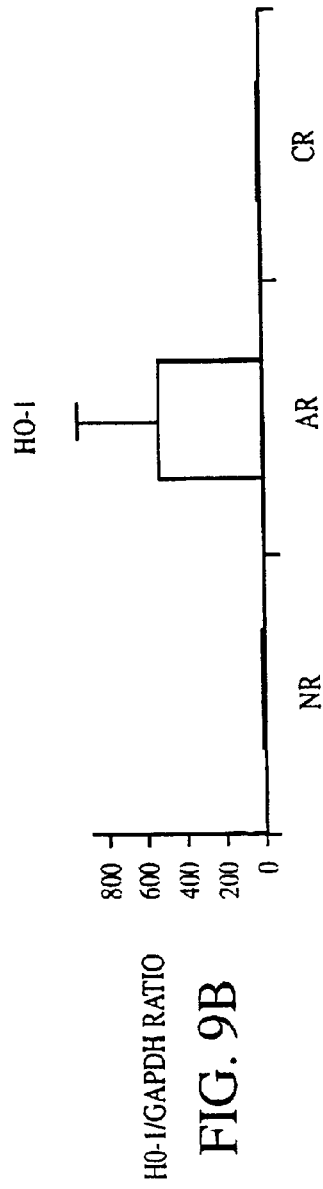

Heightened HO-1 gene expression in acute rejection but not in chronic rejection To test whether induction of HO-1 occurs in tissue inflammation from acute rejection, we compared HO-1 gene expression between rejection and nonrejection. We found an up-regulation of HO-1 gene in acute rejection, but not chronic rejection or nonrejection. The mean$\pm$SEM of mRNA levels (fg/ng GAPDH) was 538$\pm$436 in AR group, was 9$\pm$9 in CR group, and was 7$\pm$7 in NR group (p=0.002) (FIG. 9B). 6 of 8 cases (75%) from acute rejection expressed HO-1, only 3 of 9 (33%) and 2 of 13 (15%) from chronic rejection and non rejection expressed the gene respectively. There was no association between levels of HO-1 expression and severity of the rejection.

Figure 10D:
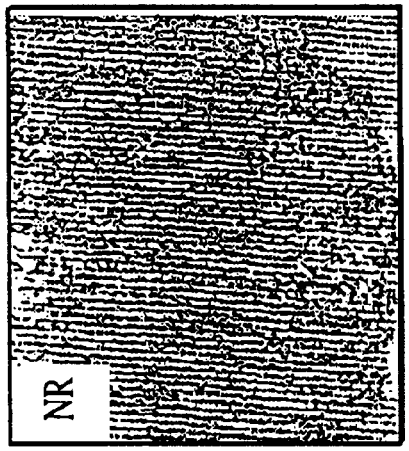
FIGS. 10A–C illustrates immunohistology of protective gene expression in allograft of acute rejection, chronic rejection and nonrejection. Endothelial cell expression of A20, as well as interstitial infiltrating cells, was observed in acute (A) and chronic (B) rejection, but not in nonrejection (C). HO-1 expression was observed in endothelial cells, glomeruli, tubular epithelial cells and interstitial infiltrating cells of acute rejection (D), but only was observed in glomeruli of chronic (E) or nonrejection (F). Bcl-$X_L$ expression was observed in endothelial cells of both rejection and nonrejection (G, H, I). Original magnification is ×200. These are representative field grafts from each group.
Figure 10E:
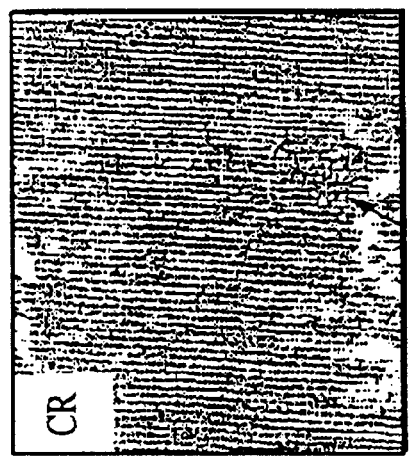
Figure 10F:
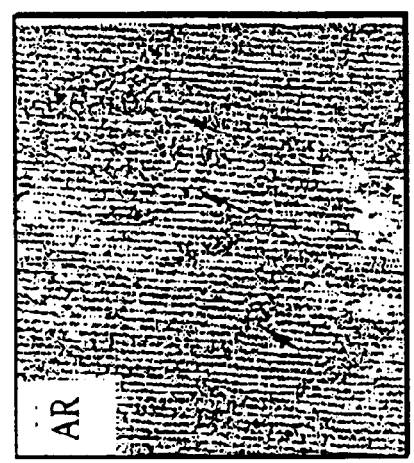

Expression of A20 protein in vascular endothelial cells and interstitial infiltrating cells. To examine the expression of A20 protein in the allograft, we used the same samples (n=8) which were subdivided from RT-PCR study. FIGS. 10(A, B, C) shows representative examples of immunohistochemical analysis of renal biopsy specimens for the presence of A20. In acute rejecting grafts, A20 was positive in both vascular endothelial cells and interstitial infiltrating cells. H&E counterstaining confirmed that A20 staining positive cells were lymphocytes. In chronic rejection, A20 was also present in both interstitial infiltrating cells and blood vessels. In contrast, the staining was negative in the sample of nonrejection.

Expression of HO-1 protein in vascular endothelial cells, interstitial infiltrating cells and renal tubular epithelial cells. FIGS. 10(D, E, F) shows representative examples of immunohistochemical analysis of renal biopsy specimens for the presence of HO-1. In acute rejecting grafts, HO-1 expressed in endothelial cells, glomeruli, tubular epithelial cells and interstitial infiltrating cells. HO-1 was negative or only positive on glomeruli alone in nonrejection samples. We also found that positive staining not only on infiltrating cells but also on tubular epithelial cells and endothelial cells. Even though, it has previously shown that HO-1 are only positive in macrophage in a murine model.

Figure 9C:
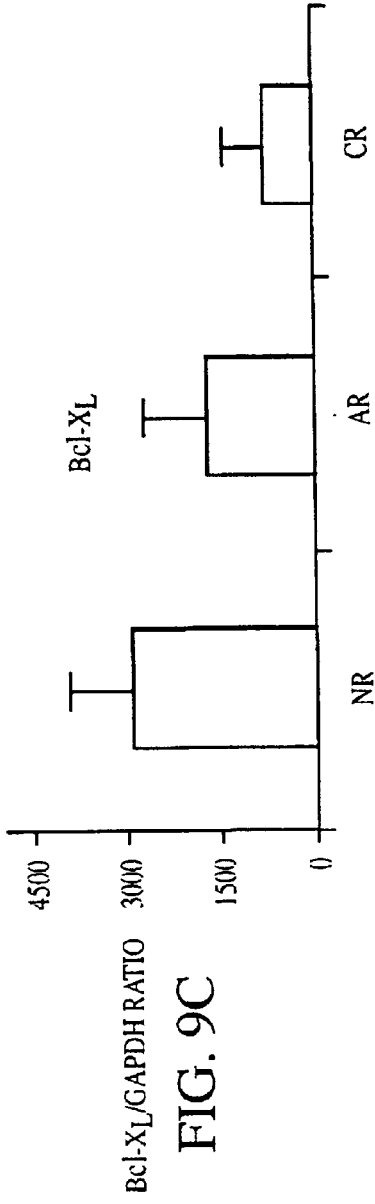

Bcl-$X_L$, constitutively expressed in intragraft during both rejection and nonreaction. We also studied Bcl-$X_L$ expression by using quantitative RT-PCR. There was no significant difference in the gene expression between rejection and nonrejection (FIG. 9C). The mean$\pm$SEM of mRNA levels (fg/ng GAPDH) was 1544$\pm$818 in AR group, was 818$\pm$410 in CR group, and was 2917$\pm$1072 in NR group. All samples (100%), including nonrejection, constitutively expressed Bcl-$X_L$ gene. hnmunohistochemistry confirmed that BCI-$X_L$ expressed in vascular endothelial cells of the renal allografts of all groups (FIGS. 10G, H, I). Some infiltrating cells are also positive staining. Our findings are consistent with the earlier report that Bcl-$X_L$ gene is constitutively expressed in vascular endothelium of renal allograft.

TABLE 7

Patient Demographics

|  | Non-rejection | Acute rejection | Chronic rejection |
|---|---|---|---|
| Number | 13 | 9 | 9 |
| Age (year) | 31 +/− 6 | 26 +/− 6 | 46 +/− 3 |
| Cadaveric donor | 6 | 4 | 4 |
| Diabetes mellitus | 1 | 1 | 5 |
| Serum creatinine | 3.1 +/− 0.8 | 3.2 +/− 1 | 3.9 +/− 0.9 |
| Post transplant (day) | 522 +/− 416 | 176 +/− 59 | 2280 +/− 614 |

DISCUSSION

Our data show dual up-regulation of A20 and HO-1 genes in acute rejection and also up-regulation of A20 in chronic rejection. Both are expressed mainly on vascular endothelial cells and interstitial infiltrating lymphocytes. To our knowledge, this is the first observation that demonstrates the up-regulation of so-called protective genes in human renal allograft rejection.

Our findings are consistent with the notion that A20 gene is up-regulated during endothelial cell activation state. We believe that EC does not express A20 during its resting state as in nonrejection while A20 is strikingly up-regulated during EC activation from rejection in order to turning off the proinflammatory signals. The balance of protective signals and inflammatory signals determines the fate of cell survival.

We believe that the dual expression of HO-1 and A20 in the acute rejecting graft might be a tissue adaptive response to minimize the extent of inflammation. Up-regulation of A20 is also found in chronic rejection, though few cases show up-regulation of HO-1. This finding suggests the different response mechanisms of HO-1 and A20 in some aspects. Up-regulation of A20 in chronic rejection might be explained by the tissue response to an injury. However, expression of A20 alone in the allograft tissue might not be enough to protect EC from development of arteriosclerosis. In addition, incidence of diabetes mellitus in the chronic rejection group is higher than the other groups. A20 might be related to the vascular protection from diabetes changes.

In summary, we observed an association between protective gene expression and allograft rejection. Up-regulation of A20 and HO-1 is strongly associated with occurrence of acute rejection. Moreover, up-regulation of A20 is also associated with chronic rejection. The intragraft expression of A20 and HO-1 genes supports experimental findings of the ant-apoptosis and anti-inflammation of the protective genes. HO-1 gene should be a candidate target for genetic or pharmacological therapy in order to reduce tissue pathology from rejection. Apart from the effort to modifying alloreactive T cell responses, we should also consider the enhancing of protective responses as a way to achieve long-term graft survival.

REFERENCES

Abraham N G, Lavrovsky Y, Schwartzman M L, et al. Transfection of the human heme oxygenase gene into rabbit coronary microvessel endothelial cells: Protective effect against heme and hemoglobin toxicity. Proc Nad Acad Sci USA 1995; 92: 6798.

Agarwal A, Balla J, Alam J, Croatt A J, Nath K A. Induction of heme oxygenase in toxic renal injury: A protective role in cisplatin nephrotoxicity in the rat. Kidney hit 1995; 48: 1298.

Agarwal A, Kim Y, Matas A J, Alam J, Nath K A. Gas-generating systems in acute renal allograft rejection in the rat: Co-induction of heme oxygenase and nitric oxide synthase. Transplantation 1996; 61:93.

Agarwal A, Nick H S. Renal response to tissue injury: lessons from heme oxygenase-1 GeneAblation and expression J Am Soc Nephrol 2000; 11: 965.

Agodoa L. Eknoyan G, Ingelfmger J, et al. Assessment of structure and function in progressive renal disease. Kidney Int 52 (Suppl 63): 1997, S-144-S-150

Aizawa T, Ishizaka N, Taguchi Ji, et al. Heme oxygenase-1 is upregulated in the kidney of angiotensin II-induced hypertensive rats: possible role in renoprotection. Hypertension 2000; 35: 800.

Almond P S, Matas A, Gillingham K J, et al. Risk factors for chronic rejection in renal allograft recipients. Transplantation 1993;55:752–756.

Alpert S, Lewis N P, Ross H, Fowler M, Valantine H A. The relationship of granzymne A and perforin expression to cardiac allograft rejection and dysfunction. Transplantation 1995;60:1478–1485.

Amersi F, Buelow F, Kato H, et al. Upregulation of heme oxygenase-1 protects genetically fat Zucker rat livers from ischemia/reperfusion injury. J Clin Invest 1999; 104: 163 1.

Atkinson E A, Barry M, Darmon A J, et al. Cytotoxic T lymphocyte-assisted suicide. Caspase 3 activation is primarily the result of the direct action of granzyme B. J Biol Chem 1998; 273:21261–21266

Bach F H, Ferran C, Hechenleitner P, et al. Accommodation of vascularized xenografts: expression of "protective genes" by donor endothelial cells in a host Th2 cytokine environment. Nat Med 1997; 3: 196.

Bach F H, Hancock W W, Ferran C. Protective genes expressed in endothelial cells: a regulatory response to injury. Immunol Today 1997; 18: 483.

Badrichani A Z, Stroka D K Bilbao G, Curiel D T, Bach F H, Ferran C. Bcl-2 and Bcl-$X_L$ serve an anti-inflammatory function in endothelial cells through inhibition of NF-KB. J Clin Invest 1999; 103: 543.

Beckingham I J, Nicholson M L, Bell P R. Analysis of factors associated with complications following renal transplant needle core biopsy. Br J Urol 1994; 73:13–15.

Benfield M R, Herrin J, Feld L, Rose S, Stablein D, Tejani A. Safety of kidney biopsy in pediatric transplantation: a report of the Controlled Clinical Trials in Pediatric Transplantation Trial of Induction Therapy Study Group. Transplantation 1999;67:544–547.

Berke G: Unlocking the secrets of CTL and NK cells. Immunology Today 1995;16:343–346

Boise L H, Gonzalez-Garcia M, Postema C E, Ding L, Lindsten T, Turka L A, Mao X, Nunez G, Thompson C B. Bcl-x, a bcl-2-related gene that functions as a dominant regulator of apoptotic cell death. Cell 1993 August 27;74(4):597–608.

Carraway M S, Ghio A J, Carter J D, Piantadosi C A. Expression of heme oxygenase-1 in the lung in chronic hypoxia. Am J Physiol Lung Cell Mol Physiol 2000; 278: L806.

Cecka J M. The UNOS Scientific Renal Transplant Registry, in Clinical Transplants 1999, Cecka and Terasaki, eds. UCLA Immunocenetics Center, Los Angeles Calif., p. 1–21

Cecka J M. The UNOS Scientific Renal Transplant Registry. Clinical Transplants 1998, Cecka and Terasaki, Eds. UCLA Tissue Typing Laboratory, Los Angeles, Calif., pp 1–16.

Clement M V, Legros-Maida S, Israel-Biet D, et al. Perforin and granzyme B expression is associated with severe acute rejection. Evidence for in situ localization in alveolar lymphocytes of lung-transplanted patients. Transplantation 1994;57:322–332

Choi A M, Alam J. Heme oxygenase-1: function, regulation, and implication of a novel stress-inducible protein in oxidant-induced lung injury. Am J Respir Cell Mol Biol 1996; 15: 9.

Colvin R B, Cohen A H, Saiontz C et al. Evaluation of pathologic criteria for acute renal allograft rejection: reproducibility, sensitivity, and clinical correlation. J Am Soc Nephrol 1997, 8:1930–1941.

Cooper J T, Stroka D M, Brostjan C, Palmetshofer A, Bach F H, Ferran C. A20 blocks endothelial cell activation through a NF-kappaB-dependent mechanism. J Biol Chem 1996; 271: 18068.

Cooper J T, Stroka D M, Brostjan C, Palmetshofer A, Bach F H, Ferran C. A20 expression inhibits endothelial cell activation. Transplant Proc 1997; 29: 881.

DeBruyne L A, Magee J C, Buelow P, Bromberg J S. Gene transfer of immunomodulatory peptides correlates with heme oxygenase-1 induction and enhanced allograft survival. Transplantation 2000; 69: 120.

Dong Z, Lavrovsky Y, Venkatachalam M A, Roy A K. Heme oxygenase-1 in tissue pathology the yin and yang. Am J Pathol 2000; 156: 1485.

Ferran C, Stroka D M, Badrichani A Z, et al. A20 inhibits NF-kappaB activation in endothelial cells without sensitizing to tumor necrosis factor-mediated apoptosis. Blood 1998; 91: 2249.

Gaber L W, Moore L W, Gaber O Tesi RJ, Meyer J, Schroeder T J. Correlation of histology to clinical rejection reversal: a thymoglobulin multicenter trial report. Kidney Int 1999;55:2415–2422.

Gulanikar A C, MacDonald A S, Sungurtekin U, Belitsky P. The incidence and impact of early rejection episodes on graft outcome in recipients of first cadaver kidney transplants. Transplantation 1992;53:323–328

Hancock W W, Buelow R, Sayegh M E, Turka L A. Antibody-induced transplant arteriosclerosis is prevented by graft expression of anti-oxidant and anti-apoptotic genes. Nat Med 1998; 4:1392.

Hariharan S, Johnson C P, Bresnahan B A, Taranto S E, McIntosh M J, Stablein D. Improved graft survival after renal transplantation in the United States, 1988 to 1996. N Engl J Med 2000, 342:605–612

Harper A M, McBride M A, and Ellison M D. The UNOS OPTN waiting list, 1988–1998. Clinical Transplants 1999, Cecka and Terasaki, Eds. UCLA Immunogenetics, Los Angeles, Calif., pp 71–82

Henkart P A: Lymphocyte-mediated cytotoxicity: two pathways and multiple effector molecules. Immunity 1994;1:343–346

Heusel J W, Wesselschmidt R L, Shresta S, Russell J H, Ley T J: Cytotoxic lymphocytes require granzyme B for the rapid induction of DNA fragmentation and apoptosis in allogeneic target cells. Cell 1994;76:977–987

Huraib S, Goldberg H, Katz A, et al. Percutaneous needle biopsy of the transplanted kidney: technique and complications. Am J Kidney Dis 1989; 14:13–17.

Kagi D, Ledermann B, Burki K, et al: Cytotoxicity mediated by T cells and natural killer cells is greatly impaired in perforin-deficient mice. Nature 1994;369:31–37

Kägi D, Ledermann B, Bürki K, Zinkemagel R M, Hengartner H. Molecular mechanisms of lymphocyte-mediated cytotoxicity and their role in immunological protection and pathogenesis in vivo. Annu Rev Immunol 1996; 14:207–232

Krams S M, Villanueva J C, Quinn M B, Martinez O M. Expression of the cytotoxic T cell mediator granzyme B during liver allograft rejection. Transpi Immunol (England) 1995;3:162–166

Lee P J, Alam J, Wiegand G W, Choi A M. Overexpression of heme oxygenase-1 in human pulmonary epithelial cells results in cell growth arrest and increased resistance to hyperoxia. Proc Natl Acad Sci USA. 1996; 93: 10393.

Legros-Maida S, Soulie A, Benvenuti C, et al. Granzyme B and perforin can be used as predictive markers of acute rejection in heart transplantation. Eur J Immunol 1994;24:229–233

Lin Y, Soares M P, Sato K, et al. Accommodated xenografts survive in the presence of anti-donor antibodies and complement that precipitate rejection of naive xenografts. J Irnmunol. 1999;163:2850.

Lindholm A, Ohlman S, Albrechtsen D, Tufveson G, Persson H, Persson N H. The impact of acute rejection episodes on long term graft function and outcome in 1347 primary renal transplants treated by 3 cyclosporine regimens. Transplantation 1993; 56:307–315

Lipman M L, Stevens A C, Strom T B: Heightened intragraft cytotoxic T lymphocyte gene expression in acutely rejecting renal allografts. J Immunol 1994;152: 5120–5127

Littel R C, Milliken G, Stroup W W, Wolfinger R D. *SAS System for Mixed Models.* Cary N.C.: SAS Institute Inc, 1996.

Liu C C, Walsh C M, Young J D. Perforin: structure and function. Immunology Today 1995; 16:194–201

Maine M D. The heme oxygenase system: a regulator of second messenger gases. Ann Rev Pharm Toxico 1997; 37: 517.

Nath K A, Balla G, Vercellotti G M, et al. Induction of heme oxygenase is a rapid protective response in rhabdomyolysis in the rat. J Clin Invest 1992; 90: 267.

Nath K A, Haggard J J, Croatt A J, Grande J P, Poss K D, Alam J. The indispensability of heme oxygenase-1 in protecting against acute heme protein-induced toxicity in vivo. Am J Pathol 2000;156:1527.

Nicholson M L, Wheatley T J, Doughman T M, et al. A prospective randomized trial of three different sizes of core-cutting needle for renal transplant biopsy. Kidney Int 2000, 58:390–395.

Ohta K, Yachie A, Fujimoto K, Kaneda H, Wada T, Toma T, Seno A, Kasahara Y, Yokoyama H, Seki H, Koizumi S. Tubular injury as a cardinal pathologic feature in human heme oxygenase-1 deficiency. Am J Kidney Dis. 2000 May;35(5):863–70.

Opipari A W, Jr., Boguski M S, Dixit V M. The A20 cDNA induced by tumor necrosis factor alpha encodes a novel type of zinc finger protein. J Biol Chem 1990; 265: 14705.

Opipari A W, Jr., Hu H M, Yabkowitz P, Dixit V M. The A20 zinc finger protein protects cells from tumor necrosis factor cytotoxicity. J Biol Chem 1992; 267: 12424.

Otterbein L E, Bach F H, Alam J, et al. Carbon monoxide has anti-inflammatory effects involving the mitogen-activated protein kinase pathway. Nat Med 2000; 6: 422.

Racusen L C, Solez K, Colvin R B et al. The Banff 97 working classification of renal allograft pathology. Kidney Int 1999;55:713–723

Rush D N, Henry S F, Jeffrey J R, Schroeder T J, Gough J. Histological findings in early routine biopsies of stable renal allograft recipients. Transplantation 1994;57:208–211.

Rush D, Nickerson P, Gough J et al. Beneficial effects of treatment of early subclinical rejection: a randomized study. J Am Soc Nephrol 1998;9:2129–2134.

Sarmna V, Lin Z, Clark L, et al. Activation of the B-cell surface receptor CD40 induces A20, a novel zinc finger protein that inhibits apoptosis. J Biol Chem 1995; 270: 12343.

Schultz M, Schuurman H J, Joergensen J, et al. Acute rejection of vascular heart allografts by perforin deficient mice. Eur J Immunol 1995;25:474–480.

Sharma V K, Bologa R M, Li B et al. Molecular executors of cell death—differential intrarenal expression of Fas ligand, Fas, granzyme B, and perforin during acute and/or chronic rejection of human renal allografts. Transplantation 1996; 62:1860–1866

Shoskes D A, Cecka J M. Deleterious effects of delayed graft function in cadaveric renal transplant recipients independent of acute rejection. Transplantation 1998;66:1697–1701

Smyth M J. Dual mechanisms of lymphocyte-mediated cytotoxicity serve to control and deliver the immune response. Bioessays 1995; 17:891–898

Smyth M J, Trapani J A. Granzymes: exogenous proteinases that induce target cell apoptosis. Immunology Today 1995; 16:202–206.

Soares M P, Brouard S, Smith R N, Otterbein L, Choi A M, Bach F H. Expression of heme oxygenase-1 by endothelial cells: a protective response to injury in transplantation. Emerging Therapeutic Targets 2000; 4: 11.

Soares M P, Lin Y, Anrather J, et al. Expression of heme oxygenase-1 can determine cardiac xenograft survival. Nat Med 1998; 4: 1073.

Sorof J M, Vartanian R K, Olson J L, Tomlanovich S J, Vincenti F G, Amend W J C. Histopathological concordance of paired renal allograft biopsy cores. Effect on the diagnosis and management of acute rejection. Transplantation 60:1215–1219, 1995.

Strehlau J, Pavlakis M, Lipman M et al. Quantitative detection of immune activation transcripts as a diagnostic tool in kidney transplantation. Proc Natl Acad Sci USA 1997; 94:695–700.

Strom T B, Tilney N L, Carpenter C B, Busch G J. Identity and cytotoxic capacity of cells infiltrating renal allografts. N Engl J Med 1975: 292: 1257–1263

Suthanthiran M, Haschemeyer R H, Riacrio R R, et al. Excellent outcome with a calcium channel blocker supplemented immunosuppressive regimen in cadaveric renal transplantation: A potential strategy to avoid antibody induction protocols. Transplantation 1993, 55:1008–1013

Suthanthiran M, Strom T B. Renal transplantation. N Engl J Med 1994; 331: 365.

Tewari M, Wolf F W, Seldin M F, O'Shea K S, Dixit V M, Turka L A. Lymphoid expression and regulation of A20, an inhibitor of programmed cell death. J Immunol 1995; 154: 1699.

Vogt B A, Shanley T P, Croatt A, Alam J, Johnson K J, Nath K A. Glomerular inflammation induces resistance to tubular injury in the rat. J Clin Invest 1996; 98: 2139.

Willis D, Moore A P, Frederick R, Willoughby D A. Heme oxygenase: A novel target for the modulation of the inflammatory response. Nat Med 1996; 2: 87.

Yachle A, Niida Y, Wada T, et al. Oxidative stress causes enhanced endothelial cell injury in human heme oxygenase-1 deficiency. J Clin Invest 1999; 103: 129.

Yoshida T, Biro P, Cohen T, Muller R M, Shibahara S. Human heme oxygenase cDNA and induction of its mRNA by hemin. Eur J Biochem 1988; 171: 457

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method for monitoring the status of a transplanted organ in a host, the method comprising:
   a) providing a post-transplantation sample from the host;
   b) determining the level of gene expression in the post-transplantation sample of at least one gene, wherein the at least one gene is heme oxygenase 1 (HO1) or A20;
   c) comparing the level of gene expression of the at least one gene in the post-transplantation sample to a baseline level of gene expression of the at least one gene or to a baseline level of gene expression of a constitutively expressed gene; and
   d) determining whether the at least one gene is upregulated relative to the baseline level of gene expression of the at least one gene or to the baseline level of gene expression of a constituitively expressed gene, wherein upregulation of the at least one gene indicates that the host is likely to experience transplant rejection; thereby monitoring the status of the transplanted organ.

2. The method of claim 1, wherein the post-transplantation sample is a graft biopsy.

3. The method of claim 1, wherein the post-transplantation sample is a fluid test sample.

4. The method of claim 3, wherein the fluid test sample is selected from the group consisting of: urine, peripheral blood, bile, bronchoalveolar lavage fluid, pericardial fluid, gastrointestinal juice, feces, and fluid gathered from an anatomic area in proximity to an allograft.

5. The method of claim 1, wherein determining the level of gene expression comprises determining the level of expression of HO1 and A20.

6. The method of claim 1, wherein the transplant rejection is an acute rejection.

7. The method of claim 6, wherein the acute rejection is an early acute rejection.

8. The method of claim 1, wherein the transplant rejection is chronic transplant rejection.

9. The method of claim 8, wherein the at least one gene is A20 and wherein upregulation of A20 indicates that the host is likely to experience chronic transplant rejection.

10. The method of claim 9, further comprising determining the level of gene expression of HO1, wherein a low expression level of HO1 indicates that the host is likely to experience chronic transplant rejection.

11. The method of claim 1, wherein the host is a human patient.

12. The method of claim 1, wherein the transplanted organ is a kidney.

13. The method of claim 1, wherein the sample is obtained during the non-rejection period.

14. The method of claim 1, wherein the constitutively expressed gene is glyceraldehyde-3-phosphate dehydrogenase.

15. The method of claim 1, wherein the constitutively expressed gene is cyclophilin B or actin.

16. The method of claim 1, wherein the at least one gene is HO1.

17. The method of claim 1, wherein the at least one gene is A20.

* * * * *

UNITED STATES PATENT AND TRADEMARK OFFICE
CERTIFICATE OF CORRECTION

PATENT NO. : 6,900,015 B2
APPLICATION NO. : 09/777732
DATED : May 31, 2005
INVENTOR(S) : Yingyos Avihigsanon et al.

It is certified that error appears in the above-identified patent and that said Letters Patent is hereby corrected as shown below:

Title Page, item [56], OTHER PUBLICATIONS, reference Almond, et al.:
   Delete "5(4):752-757" and replace with --55(4):752-757--

Title Page, item [56], OTHER PUBLICATIONS, reference Alpert, et al.:
   Delete "Relationahip" and replace with --Relationship--

Title Page, item [56], OTHER PUBLICATIONS, reference Atkinson, et al.:
   Delete "Lympocyte-assisted" and replace with --Lymphocyte-assisted--

Page 2, item [56], OTHER PUBLICATIONS, reference Schulz, et al.:
   Delete "mcie" and replace with --mice--

Page 2, item [56], OTHER PUBLICATIONS, reference Smyth, et al.:
   Delete "Toda" and replace with --Today--

Page 3, item [56], OTHER PUBLICATIONS, reference Wright, et al.:
   Delete "Pahtology" and replace with --Pathology--

Signed and Sealed this

Eighteenth Day of July, 2006

JON W. DUDAS
*Director of the United States Patent and Trademark Office*

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 1
ggtgaaggtc ggagtcaacg                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 2
caaagttgtc atggatgacc                                          20

<210> SEQ ID NO 3
<211> LENGTH: 20
<212> TYPE: DNA
<213> ORGANISM: Artificial Sequence

```
-continued

<220> FEATURE:
<223> OTHER INFORMATION: Synthetically generated primer

<400> SEQUENCE: 3
cctctggagg aagtgctaaa                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 4
atggttgctg tctcatcagc                                              20

<210> SEQ ID NO 5
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 5
ttctacagcc accatgagaa g                                            21

<210> SEQ ID NO 6
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 6
cagctcgaac actttgaata t                                            21

<210> SEQ ID NO 7
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 7
tttaggtata tctttggact tcctc                                        25

<210> SEQ ID NO 8
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 8
gtgttcttta gtgcccatca a                                            21

<210> SEQ ID NO 9
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 9
tctcttggca gccttcct                                                18
```

```
<210> SEQ ID NO 10
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 10
aattctcagc ctcttcaaaa actt                                          24

<210> SEQ ID NO 11
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 11
gccgtggagc aggtgaag                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 12
aagcccagag acaagata                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 13
ccgtggcttt gagtaatgag                                               20

<210> SEQ ID NO 14
<211> LENGTH: 19
<212> TYPE: DNA
<213> ORGANISM: Artificial Sequence
<220> FEATURE:
<223> OTHER INFORMATION: Synthetically generated primer

<400> SEQUENCE: 14
cagattctgt tacattccc                                                19

<210> SEQ ID NO 15
<211> LENGTH: 17
<212> TYPE: DNA
<213> ORGANISM: Artificial Sequence
<220> FEATURE:
<223> OTHER INFORMATION: Synthetically generated primer

<400> SEQUENCE: 15
ggaggccata gtgaagg                                                  17

<210> SEQ ID NO 16
<211> LENGTH: 17
<212> TYPE: DNA
<213> ORGANISM: Artificial Sequence
<220> FEATURE:
<223> OTHER INFORMATION: Synthetically generated primer
```

```
<400> SEQUENCE: 16
gggtcggctc tccatag                                          17

<210> SEQ ID NO 17
<211> LENGTH: 17
<212> TYPE: DNA
<213> ORGANISM: Artificial Sequence
<220> FEATURE:
<223> OTHER INFORMATION: Synthetically generated primer

<400> SEQUENCE: 17
cggctcacac tcacagg                                          17

<210> SEQ ID NO 18
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 18
ctgccgtgga tgcctatg                                         18

<210> SEQ ID NO 19
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 19
ggggaagctc cataaatgtc acct                                  24

<210> SEQ ID NO 20
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 20
tacacacaag agggcctcca gagt                                  24

<210> SEQ ID NO 21
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 21
gcctgtgtct ccttgtga                                         18

<210> SEQ ID NO 22
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 22
gccacccttc ttatactt                                         18

<210> SEQ ID NO 23
```

```
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 23
ctgcggatct ctgtgtcatt                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 24
ctcagagtgt tgctatggtg                                              20

<210> SEQ ID NO 25
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 25
ccagagcatc caaaagagtg tg                                           22

<210> SEQ ID NO 26
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 26
ctagttggcc cctgagataa ag                                           22

<210> SEQ ID NO 27
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 27
gcaatgcacg tggcccagcc                                              20

<210> SEQ ID NO 28
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 28
tttcacattc tggctctgtt gg                                           22

<210> SEQ ID NO 29
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 29
```
cggcacgcct cgctgtcatc                                          20

<210> SEQ ID NO 30
<211> LENGTH: 19
<212> TYPE: DNA
<213> ORGANISM: Artificial Sequence
<220> FEATURE:
<223> OTHER INFORMATION: Synthetically generated primer

<400> SEQUENCE: 30
tgtactcccg aacccattt                                           19

<210> SEQ ID NO 31
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 31
tccacgctgt tttgacctcc atag                                     24

<210> SEQ ID NO 32
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 32
gacatctttc tcgggttct cgtt                                      24

<210> SEQ ID NO 33
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 33
tttgagcaat atgcggaaag c                                        21

<210> SEQ ID NO 34
<211> LENGTH: 18
<212> TYPE: DNA
<213> ORGANISM: Artificial Sequence
<220> FEATURE:
<223> OTHER INFORMATION: Synthetically generated primer

<400> SEQUENCE: 34
catgcaccga tacacact                                            18

<210> SEQ ID NO 35
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 35
agttgtccca ttcgtcattc c                                        21

<210> SEQ ID NO 36
<211> LENGTH: 25
<212> TYPE: DNA

```
<213> ORGANISM: Artificial Sequence
<220> FEATURE:
<223> OTHER INFORMATION: Synthetically generated primer

<400> SEQUENCE: 36
cagaagggac tgaatcggag atgga                                        25

<210> SEQ ID NO 37
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 37
ccgcggtgaa tggagccact g                                            21

<210> SEQ ID NO 38
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 38
ctaggtggtc attcaggtaa gtggc                                        25

<210> SEQ ID NO 39
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 39
aggagattga gcgcaacaag                                              20

<210> SEQ ID NO 40
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 40
ggagcaggac ctggccttct gg                                           22

<210> SEQ ID NO 41
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 41
gctctggtcc ttggtgtcat                                              20

<210> SEQ ID NO 42
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 42
tgcaggaaga tcgaaagtgc g                                            21
```

<210> SEQ ID NO 43
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 43
gaggcatgcc attgtttcgt c                                      21

<210> SEQ ID NO 44
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 44
cagtacagct tcagcactga c                                      21

<210> SEQ ID NO 45
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 45
atgaagtggg tgccgtagtt g                                      21

<210> SEQ ID NO 46
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 46
cgggtgatct ttggtctctt c                                      21

<210> SEQ ID NO 47
<211> LENGTH: 16
<212> TYPE: DNA
<213> ORGANISM: Artificial Sequence
<220> FEATURE:
<223> OTHER INFORMATION: Synthetically generated primer

<400> SEQUENCE: 47
gagacttcac cagggg                                            16

<210> SEQ ID NO 48
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 48
ctgtctgtct tggtgctctc c                                      21